(12) United States Patent
Mikkola et al.

(10) Patent No.: US 11,845,959 B2
(45) Date of Patent: Dec. 19, 2023

(54) IDENTIFICATION OF FACTOR THAT PROMOTES HUMAN HSC SELF-RENEWAL

(71) Applicant: THE REGENTS OF THE UNIVERSITY OF CALIFORNIA, Oakland, CA (US)

(72) Inventors: Hanna Mikkola, Los Angeles, CA (US); Vincenzo Calvanese, Los Angeles, CA (US); Andrew T. Nguyen, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1006 days.

(21) Appl. No.: 16/310,206

(22) PCT Filed: Jun. 16, 2017

(86) PCT No.: PCT/IB2017/053607
§ 371 (c)(1),
(2) Date: Dec. 14, 2018

(87) PCT Pub. No.: WO2017/216775
PCT Pub. Date: Dec. 21, 2017

(65) Prior Publication Data
US 2019/0270967 A1 Sep. 5, 2019

Related U.S. Application Data

(60) Provisional application No. 62/350,824, filed on Jun. 16, 2016.

(51) Int. Cl.
| | | |
|---|---|---|
| C12N 5/0789 | (2010.01) | |
| A61K 35/28 | (2015.01) | |
| C12N 5/074 | (2010.01) | |
| C12N 15/85 | (2006.01) | |
| A01K 67/027 | (2006.01) | |
| C12N 15/861 | (2006.01) | |

(52) U.S. Cl.
CPC ........ *C12N 5/0647* (2013.01); *A01K 67/0271* (2013.01); *A61K 35/28* (2013.01); *C12N 5/0696* (2013.01); *C12N 15/85* (2013.01); *C12N 15/861* (2013.01); *A01K 2227/105* (2013.01); *A01K 2267/02* (2013.01); *C12N 2501/60* (2013.01); *C12N 2501/727* (2013.01); *C12N 2502/1171* (2013.01); *C12N 2502/1352* (2013.01); *C12N 2502/1394* (2013.01); *C12N 2510/00* (2013.01)

(58) Field of Classification Search
None
See application file for complete search history.

(56) References Cited

U.S. PATENT DOCUMENTS

2014/0037600 A1  2/2014  Yu et al.

FOREIGN PATENT DOCUMENTS

WO  WO 2013/086029  6/2013

OTHER PUBLICATIONS

Mulloy, et al., "Transforming Human Blood Stem and Progenitor Cells: A New Way Forward in Leukemia Modeling," Cell Cycle, 7(21): 3314-3319, 2008.
Partial Supplementary European Search Report issued in European Patent Application No. 17812872.4, dated Nov. 15, 2019.
Adelman et al., "Promoter-proximal pausing of RNA polymerase II: emerging roles in metazoans" *Nat Rev Genet*, 2012, 13:720-731.
Bitoun et al., "The mixed-lineage leukemia fusion partner AF4 stiumulates RNA polymerase II transcriptional elongation and mediates coordinated chromatin remodeling" *Human Mol Genet.*, 2007, 16:92-106.
Casero et al., "Long non-coding RNA profiling of human lymphoid progenitor cells reveals transcriptional divergence of B cell and T cell lineage," *Nat Immunol*, 2015, 16:1282-1291.
Chen et al., "PAF1, a Molecular Regulator of Promoter-Proximal Pausing by RNA Polymerase II" *Cell*, 2015, 162:1003-1015.
Core et al., "Defining the status of RNA polymerase at promoters" *Cell Reports*, 2012, 2:1025-1035.
Dou et al., "Medical HOXA genes demarcate haematopoietic stem cell fate during human development" *Nat Cell Biol.*, 2016, 18:595-606.
Fares et al., "Cord blood expansion. Pyrimidoindole derivatives are agonists of human hematopoietic stem cell self-renewal" *Science*, 2014, 345:1509-1512.
Gilchrist et al., "NELF-mediated stalling of Pol II can enhance gene expression by blocking promoter-proximal nucleosome assembly," *Genes dev.*, 22:1921-1933.
Gritz et al., "Specification and function of hemogenic endothelium during embryogenesis" *Cell Mol Life Sci*, 2016, 73:1547-1567.
He et al., "Human Polymerase-Associated Factor complex (PAFc) connects the Super Elongation Complex (SEC) to RNA polymerase II on chromatin" *Proceedings of the National Academy of Sciences of the United States of America*, 2011, 108(36):E636-645.
International Search Report and Written Opinion issued in International Patent Application No. PCT/IB2017/053607, dated Nov. 28, 2017.
Kim et al., "The human PAF1 complex acts in chromatin transcription elongation both independently and cooperatively with SII/TFIIS" *Cell*, 2010, 140:491-503.
Li et al., "AF9 YEATS domain links histone acetylation to DOT1L-mediated H3K79 methylation" *Cell*, 2014, 159:558-571.

(Continued)

*Primary Examiner* — Michail A Belyavskyi
(74) *Attorney, Agent, or Firm* — Norton Rose Fulbright US LLP

(57) ABSTRACT

Transient MLLT3 overexpression in culture may be used to expand human HSCs in vitro, and thereby improve the efficiency and safety of HSC transplantation.

20 Claims, 24 Drawing Sheets
Specification includes a Sequence Listing.

(56) References Cited

OTHER PUBLICATIONS

Lin et al., "AFF4, a component of the ELL/P-TEFb elongation complex and a shared subunit of MLL chimeras, can link transcription elongation to leukemia" *Mol Cell*, 2010, 37:429-437.

Lin et al., "Dynamic transcriptional events in embryonic stem cells mediated yb the super elongation complex (SEC)" *Genes & Development*, 2011, 25:1486-1498.

Luo et al., "The super elongation complex (SEC) family in transcriptional control," *Nat Rev Mol Cell Biol.*, 2012, 13:543-547.

Magnusson et al., "Expansion on Stromal Cells Preserves the Undifferentiated State of Human Hematopoietic Stem Cells Despite Compromised Reconstitution Ability" *PLoS ONE*, 2013, 8(1):e53912, 16 pages.

Mohan et al., "Linking H3K79 trimethylation to Wnt signaling through a novel Dot1-containing complex (DotCom)." *Genes Dev.*, 2010, 24:574-589.

Nagaike et al., "Transcriptional activators enhance polyadenylation of mRNA precursors" *Mol Cell*, 2011, 41:409-418.

Peterlin et al., "Controlling the elongation phase of transcription with P-TEFb" *Mol Cell*, 2006, 23:297-305.

Pina et al., "MLLT3 regulates early human erythroid and megakaryocytic cell fate" *Cell Stem Cell*, 2008, 2:264-273.

Prashad et al., "GPI-80 Defines Self-Renewal Ability in Hematopoietic Stem Cells During Human Development" *Cell Stem Cell*, 2014, 16(1):80-87.

Quinlan et al., "BEDTools: a flexible suite of utilities for comparing genomic features," *Bioinformatics*, 2010, 26:841-842.

Swiers et al., "A short history of hemogenic endothelium" *Blood cells, molecules & disease*, 2013, 51:206-212.

Trapnell et al., "TopHat: discovering splice junctions with RNA-Seq" *Bioinformatics*, 2009, 25:1105-1111.

Yang et al. "RNA polymerase II pausing modulates hematopoietic stem cell emergence in zebra fish" *Blood*, 2016, 128:1701-1710.

IDENTIFICATION OF FACTOR THAT PROMOTES HUMAN HSC SELF-RENEWAL

CROSS-REFERENCE TO RELATED APPLICATIONS

This application is a national phase application under 35 U.S.C. § 371 of International Application No. PCT/IB2017/053607, filed Jun. 16, 2017, which claims benefit to U.S. Provisional Patent Application No. 62/350,824, filed Jun. 16, 2016. The entire contents of the referenced applications are incorporated herein by reference.

The invention was made with government support under 1DK100959, awarded by the National Institutes of Health. The government has certain rights in the invention.

FIELD OF THE INVENTION

The present invention relates generally to the field of medicine More particularly, it concerns the expansion of human hematopoietic stem cells (HSCs) in vitro using MLLT3 and/or CDK9 kinase inhibitors.

BACKGROUND

Hematopoietic stem cell (HSC) self-renewal is a key property that endows the ability of HSCs to persist for life, continuously replenish the hematopoietic system, and to engraft in a recipient upon transplantation. Definitive HSCs in human embryo arise in the first trimester from hemogenic endothelium (HE)[1, 2], and undergo maturation and expansion in the fetal liver. However, the key machinery that governs the self-renewal and engraftment ability of human HSCs remains elusive. As a result, it remains a challenge to maintain and expand engraftable human HSCs in culture and to generate them from pluripotent stem cells (PSC).

SUMMARY OF THE INVENTION

Embodiments provide methods and compositions relating to differentiated hematopoietic cells created from hematopoietic stem cells (which themselves could be generated from pluripotent or multipotent cells such as embryonic stem cells and induced pluripotent stem cells) that contain a heterologous MLLT3 nucleic acid or are progeny of such cells. In any embodiment discussed herein, instead of introducing MLLT3 into cells, hematopoietic stem cells may be exposed to, contacted with, or incubated with a CDK9 kinase inhibitor.

In certain embodiments, there are methods for generating a blood cell, for producing or creating a hematopoietic cell, for differentiating a hematopoietic stem cell, for creating a differentiated hematopoietic cell, for producing a differentiated hematopoietic cell or a specific blood cell, for extending the amount of time a hematopoietic stem cell can be maintained in culture, for increasing the time or number of generations a hematopoietic stem cell can be maintained in culture, increasing the number of days, weeks, or cell cycles a hematopoietic stem cell can be maintained in culture, maintaining the number of hematopoietic stem cells in culture, increasing the viability percentage of hematopoietic stem cells in culture, expanding the number of hematopoietic stem cells in culture, increasing or improving the transplantation ability, increasing or improving the grafting ability, and extending the self-renewal capability of hematopoietic stem cells. Such methods may involve one or more steps discussed herein including, but not limited to, introducing MLLT3 into a cell, contacting or incubating cells with a CDK9 kinase inhibitor, culturing cells, exposing cells to one or more differentiation agents or factors, incubating cells under conditions for self-renewal, incubating cells under conditions for differentiating them, co-culturing the cells with other cells, co-culturing the cells with stromal cells, inducing expression of exogenous MLLT3 in a cell, infecting a cell with a viral vector encoding MLLT3, transfecting an expression construct encoding MLLT3 into a cell, transfecting into a cell a nucleic acid molecule comprising an MLLT3 nucleic acid sequence, transfecting an MLLT3 mRNA into cells, introducing cells containing or previously containing an exogenous MLLT3-encoding nucleic acid into an organism, transplanting cells containing or previously containing an exogenous MLLT3-encoding nucleic acid into an organism, inducing expression of exogenous MLLT3 in a cell, expressing exogenous MLLT3 in a cell, enriching for cells, culturing cells, isolating cells, purifying cells, or discarding all or part of a population of cells. Cells may be embryonic stem cells, hematopoietic stem cells, fetal liver stem cells, bone marrow stem cells, cord blood stem cells, hematopoietic stem and progenitor cells, induced pluripotent stem cells, a hematopoietic cell or any cell showing one or more signs of a hematopoietic cell along one or more of the following lineages: erythrocytes, megakaryocytes, monocytes, B cells, T cells, B lymphocyte progenitor, T lymphocyte progenitor, helper T cell, cytotoxic T cell, T memory cell, T helper differentiation cell, macrophages, neutrophils, dendritic cells, platelets, eosinophils, basophils, or natural killer cells. It is specifically contemplated that one or more cell types may be excluded in an embodiment. Cells may be cultured on a plate, in suspension, and/or in 3D tissue culture.

In some embodiments, there are methods for generating a blood cell comprising a) introducing MLLT3 into a hematopoietic stem cell; and b) differentiating the MLLT-3-introduced cell. In other embodiments, there are methods of producing hematopoietic cells comprising obtaining hematopoietic stems cells from a subject; b) introducing MLLT3 into of at least some of the hematopoietic stem cells; c) culturing MLLT3-introduced hematopoietic stem cells to enrich for the hematopoietic stem cells; and, d) exposing the hematopoietic stem cells to conditions that allow the hematopoietic stem cells to differentiate into one or more hematopoietic cells. The term "MLLT-3-introduced cells" refers to cells that have had an exogenous MLLT3 gene or protein introduced into it, as well as the progeny of such cells.

In further embodiments, there are methods of producing hematopoietic cells comprising: a) generating hematopoietic stems cells from embryonic stem cells; b) introducing MLLT3 into at least some of the hematopoietic stem cells; c) culturing MLLT3-introduced hematopoietic stem cells to enrich for the hematopoietic stem cells; and, d) exposing the hematopoietic stem cells to conditions that allow the hematopoietic stem cells to differentiate into one or more hematopoietic cells.

Some embodiments involve methods for providing hematopoietic cells to a subject comprising: a) obtaining hematopoietic stems cells from the subject; b) introducing MLLT3 into at least some of the hematopoietic stem cells; and, c) administering the cells in which MLLT3 had been introduced into the subject, wherein the cells may or may not be at least partially differentiated following introduction of MLLT3. The term "partially differentiated" means that a cell or cells may exhibit at least one trait of a differentiated cell, such as expression of a cell surface marker. A subject is an organism with a hematopoietic system. In certain embodiments, the subject is a mammal, including, but not limited to humans.

In additional embodiments, there are methods for providing hematopoietic cells to a subject comprising: a) generating induced pluripotent stems cells (iPSCs) from the subject; b) generating hematopoietic stems cells from the iPSCs; c) introducing MLLT3 into at least some of the hematopoietic stem cells; and, d) administering the cells in which MLLT3 has been introduced into the subject, wherein the cells may or may not be at least partially differentiated following introduction of MLLT3.

In some embodiments, MLLT3 is introduced into a cell to provide MLLT3 activity to the cell. Embodiments include providing human MLTT3 protein (all or part) to a human cell. Some methods involve introducing an MLLT3-encoding nucleic acid into a cell, while methods may include introducing an MLLT3 polypeptide to a cell. In particular embodiments, an MLLT3 polypeptide is alternatively referred to as protein AF-9. In certain aspects, protein AF-9 may refer to protein AF-9 isoform a (comprising the amino acid sequence associated with NCBI Accession number NP_004520.2) or protein AF-9 isoform b (comprising the amino acid sequence associated with NCBI Accession number NP_001273620.1). In other aspects, an MLLT3-encoding nucleic acid may refer to MLLT3 variant 1 (comprising the mRNA or cDNA coding region associated with NCBI Accession number NM_004529.3) or MLLT3 variant 2 (comprising the mRNA or cDNA coding region associated with NCBI Accession number NM_001286691.1). In further aspects, an MLLT3-encoding nucleic acid may refer to MLLT3 short isoform (comprising the mRNA or cDNA coding region associated with ENSEMBL Transcript ENST00000380321.5 and in UNIPROT as a protein B1APT5). The nucleic acid may be under the control of a promoter that is constitutive, inducible, repressible, transient, or regulatable. In certain embodiments, the promoter provides a high level of expression relative to the expression of endogenous MLLT3. In particular embodiments, the promoter is temporally- or developmentally-limited or specific. For instance, in some cases, the promoter is capable of or specific for driving expression in a hematopoietic cell or a hematopoietic stem cell. In other embodiments, there may be one or more enhancers as well.

In certain embodiments, an MLLT3-encoding nucleic acid comprises a portion or the entire sequence of MLLT3 variant 1, given by:

```
                                           (SEQ ID NO: 1)
ATGGCTAGCTCGTGTGCCGTGCAGGTGAAGCTGGAGCTGGGGCACCGCGC

CCAGGTGAGGAAAAAACCCACCGTGGAGGGCTTCACCCACGACTGGATGG

TGTTCGTACGCGGTCCGGAGCACAGTAACATACAGCACTTTGTGGAAAA

GTCGTCTTCCACTTGCACGAAAGCTTTCCTAGGCCAAAAAGAGTGTGCAA

AGATCCACCTTACAAAGTAGAAGAATCTGGGTATGCTGGTTTCATTTTGC

CAATTGAAGTTTATTTTAAAAACAAGGAAGAACCTAGGAAAGTCCGCTTT

GATTATGACTTATTCCTGCATCTTGAAGGCCATCCACCAGTGAATCACCT

CCGCTGTGAAAAGCTAACTTTCAACAACCCCACAGAGGACTTTAGGAGAA

AGTTGCTGAAGGCAGGAGGGGACCCTAATAGGAGTATTCATACCAGCAGC

AGCAGCAGCAGCAGCAGTAGCAGCAGCAGCAGCAGCAGCAGCAGCAGCAG

TAGCAGCAGCAGCAGCAGCAGCAGCAGCAGCAGTAGCAGCAGCAGTAGCA

GCAGCAGCAGCAGCAGTAGTACCAGTTTTTCAAAGCCTCACAAATTAATG

AAGGAGCACAAGGAAAAACCTTCTAAAGACTCCAGAGAACATAAAAGTGC

CTTCAAAGAACCTTCCAGGGATCACAACAAATCTTCCAAAGAATCCTCTA

AGAAACCCAAAGAAAATAAACCACTGAAAGAAGAGAAAATAGTTCCTAAG

ATGGCCTTCAAGGAACCTAAACCCATGTCAAAAGAGCCAAAACCAGATAG

TAACTTACTCACCATCACCAGTGGACAAGATAAGAAGGCTCCTAGTAAAA

GGCCGCCCATTTCAGATTCTGAAGAACTCTCAGCCAAAAAAGGAAAAAG

AGTAGCTCAGAGGCTTTATTTAAAAGTTTTTCTAGCGCACCACCACTGAT

ACTCACTTGTTCTGCTGACAAAAAACAGATAAAAGATAAATCTCATGTCA

AGATGGGAAAGGTCAAAATTGAAAGTGAGACATCAGAGAAGAAGAAATCA

ACGTTACCGCCATTTGATGATATTGTGGATCCCAATGATTCAGATGTGGA

GGAGAATATATCCTCTAAATCTGATTCTGAACAACCCAGTCCTGCCAGCT

CCAGCTCCAGCTCCAGCTCCAGCTTCACACCATCCCAGACCAGGCAACAA

GGTCCTTTGAGGTCTATAATGAAAGATCTGCATTCTGATGACAATGAGGA

GGAATCAGATGAAGTGGAGGATAACGACAATGACTCTGAAATGGAGAGGC

CTGTAAATAGAGGAGGCAGCCGAAGTCGCAGAGTTAGCTTAAGTGATGGC

AGCGATAGTGAAAGCAGTTCTGCTTCTTCACCCCTACATCACGAACCTCC

ACCACCCTTACTAAAAACCAACAACAACCAGATTCTTGAAGTGAAAAGTC

CAATAAAGCAAAGCAAATCAGATAAGCAAATAAAGAATGGTGAATGTGAC

AAGGCATACCTAGATGAACTGGTAGAGCTTCACAGAAGGTTAATGACATT

GAGAGAAAGACACATTCTGCAGCAGATCGTGAACCTTATAGAAGAAACTG

GACACTTTCATATCACAAACACAACATTTGATTTTGATCTTTGCTCGCTG

GACAAAACCACAGTCCGTAAACTACAGAGTTACCTGGAAACATCTGGAAC

ATCCTGA.
```

In other embodiments, an MLLT3-encoding nucleic acid comprises a portion or the entire sequence of MLLT3 variant 2, given by:

```
                                           (SEQ ID NO: 2)
ATGTGTGCCGTGCAGGTGAAGCTGGAGCTGGGGCACCGCGCCCAGGTGAG

GAAAAAACCCACCGTGGAGGGCTTCACCCACGACTGGATGGTGTTCGTAC

GCGGTCCGGAGCACAGTAACATACAGCACTTTGTGGAGAAAGTCGTCTTC

CACTTGCACGAAAGCTTTCCTAGGCCAAAAAGAGTGTGCAAAGATCCACC

TTACAAAGTAGAAGAATCTGGGTATGCTGGTTTCATTTTGCCAATTGAAG

TTTATTTTAAAAACAAGGAAGAACCTAGGAAAGTCCGCTTTGATTATGAC

TTATTCCTGCATCTTGAAGGCCATCCACCAGTGAATCACCTCCGCTGTGA

AAAGCTAACTTTCAACAACCCCACAGAGGACTTTAGGAGAAAGTTGCTGA

AGGCAGGAGGGGACCCTAATAGGAGTATTCATACCAGCAGCAGCAGCAGC

AGCAGCAGTAGCAGCAGCAGCAGCAGCAGCAGCAGCAGCAGTAGCAGCAG

CAGCAGCAGCAGCAGCAGCAGCAGTAGCAGCAGCAGTAGCAGCAGCAGCA

GCAGCAGTAGTACCAGTTTTTCAAAGCCTCACAAATTAATGAAGGAGCAC
```

-continued

```
AAGGAAAAACCTTCTAAAGACTCCAGAGAACATAAAAGTGCCTTCAAAGA

ACCTTCCAGGGATCACAACAAATCTTCCAAAGAATCCTCTAAGAAACCCA

AAGAAAATAAACCACTGAAAGAAGAGAAAATAGTTCCTAAGATGGCCTTC

AAGGAACCTAAACCCATGTCAAAAGAGCCAAAACCAGATAGTAACTTACT

CACCATCACCAGTGGACAAGATAAGAAGGCTCCTAGTAAAAGGCCGCCCA

TTTCAGATTCTGAAGAACTCTCAGCCAAAAAAGGAAAAAGAGTAGCTCA

GAGGCTTTATTTAAAAGTTTTTCTAGCGCACCACCACTGATACTCACTTG

TTCTGCTGACAAAAAACAGATAAAAGATAAATCTCATGTCAAGATGGGAA

AGGTCAAAATTGAAAGTGAGACATCAGAGAAGAAGAAATCAACGTTACCG

CCATTTGATGATATTGTGGATCCCAATGATTCAGATGTGGAGGAGAATAT

ATCCTCTAAATCTGATTCTGAACAACCCAGTCCTGCCAGCTCCAGCTCCA

GCTCCAGCTCCAGCTTCACACCATCCCAGACCAGGCAACAAGGTCCTTTG

AGGTCTATAATGAAAGATCTGCATTCTGATGACAATGAGGAGGAATCAGA

TGAAGTGGAGGATAACGACAATGACTCTGAAATGGAGAGGCCTGTAAATA

GAGGAGGCAGCCGAAGTCGCAGAGTTAGCTTAAGTGATGGCAGCGATAGT

GAAAGCAGTTCTGCTTCTTCACCCCTACATCACGAACCTCCACCACCCTT

ACTAAAAACCAACAACAACCAGATTCTTGAAGTGAAAAGTCCAATAAAGC

AAAGCAAATCAGATAAGCAAATAAAGAATGGTGAATGTGACAAGGCATAC

CTAGATGAACTGGTAGAGCTTCACAGAAGGTTAATGACATTGAGAGAAAG

ACACATTCTGCAGCAGATCGTGAACCTTATAGAAGAAACTGGACACTTTC

ATATCACAAACACAACATTTGATTTTGATCTTTGCTCGCTGGACAAAACC

ACAGTCCGTAAACTACAGAGTTACCTGGAAACATCTGGAACATCCTGA
```

In particular embodiments, an MLLT3 polypeptide or AF-9 protein comprises a portion or the entire sequence of protein AF-9 isoform a, given by:

```
                                        (SEQ ID NO: 3)
MASSCAVQVKLELGHRAQVRKKPTVEGFTHDWMVFVRGPEHSNIQHFVEK

VVFHLHESFPRPKRVCKDPPYKVEESGYAGFILPIEVYFKNKEEPRKVRF

DYDLFLHLEGHPPVNHLRCEKLTFNNPTEDFRRKLLKAGGDPNRSIHTSS

SSSSSSSSSSSSSSSSSSSSSSSSSSSSSSSSSSSSSTSFSKPHKLM

KEHKEKPSKDSREHKSAFKEPSRDHNKSSKESSKKPKENKPLKEEKIVPK

MAFKEPKPMSKEPKPDSNLLTITSGQDKKAPSKRPPISDSEELSAKKRKK

SSSEALFKSFSSAPPLILTCSADKKQIKDKSHVKMGKVKIESETSEKKKS

TLPPFDDIVDPNDSDVEENISSKSDSEQPSPASSSSSSSSSFTPSQTRQQ

GPLRSIMKDLHSDDNEEESDEVEDNDNDSEMERPVNRGGSRSRRVSLSDG

SDSESSSASSPLHHEPPPPLLKTNNNQILEVKSPIKQSKSDKQIKNGECD

KAYLDELVELHRRLMTLRERHILQQIVNLIEETGHFHITNTTFDFDLCSL

DKTTVRKLQSYLETSGTS
```

In some embodiments, an MLLT3 polypeptide or AF-9 protein comprises a portion or the entire sequence of protein AF-9 isoform b, given by:

```
                                        (SEQ ID NO: 4)
MCAVQVKLELGHRAQVRKKPTVEGFTHDWMVFVRGPEHSNIQHFVEKVVF

HLHESFPRPKRVCKDPPYKVEESGYAGFILPIEVYFKNKEEPRKVRFDYD

LFLHLEGHPPVNHLRCEKLTFNNPTEDFRRKLLKAGGDPNRSIHTSSSSS

SSSSSSSSSSSSSSSSSSSSSSSSSSSSSSSSSSSSTSFSKPHKLMKEH

KEKPSKDSREHKSAFKEPSRDHNKSSKESSKKPKENKPLKEEKIVPKMAF

KEPKPMSKEPKPDSNLLTITSGQDKKAPSKRPPISDSEELSAKKRKKSSS

EALFKSFSSAPPLILTCSADKKQIKDKSHVKMGKVKIESETSEKKKSTLP

PFDDIVDPNDSDVEENISSKSDSEQPSPASSSSSSSSSFTPSQTRQQGPL

RSIMKDLHSDDNEEESDEVEDNDNDSEMERPVNRGGSRSRRVSLSDGSDS

ESSSASSPLHHEPPPPLLKTNNNQILEVKSPIKQSKSDKQIKNGECDKAY

LDELVELHRRLMTLRERHILQQIVNLIEETGHFHITNTTFDFDLCSLDKT

TVRKLQSYLETSGTS
```

In other embodiments, an MLLT3-encoding nucleic acid comprises a portion or the entire sequence of MLLT3 short isotype, given by:

```
                                        (SEQ ID NO: 5)
ATGAAAGATCTGCATTCTGATGACAATGAGGAGGAATCAGATGAAGTGGA

GGATAACGACAATGACTCTGAAATGGAGAGGCCTGTAAATAGAGGAGGC

AGCCGAAGTCGCAGAGTTAGCTTAAGTGATGGCAGCGATAGTGAAAGCA

GTTCTGCTTCTTCACCCCTACATCACGAACCTCCACCACCCTTACTAAAA

ACCAACAACAACCAGATTCTTGAAGTGAAAAGTCCAATAAAGCAAAGCAA

ATCAGATAAGCAAATAAAGAATGGTGAATGTGACAAGGCATACCTAGAT

GAACTGGTAGAGCTTCACAGAAGGTTAATGACATTGAGAGAAAGACACAT

TCTGCAGCAGATCGTGAACCTTATAGAAGAAACTGGACACTTTCATATCA

CAAACACAACATTTGATTTTGATCTTTGCTCGCTGGACAAAACCACAGTC

CGTAAACTACAGAGTTACCTGGAAACATCTGGAACATCCTGA
```

In some embodiments, an MLLT3 polypeptide or AF-9 protein comprises a portion or the entire sequence of protein AF-9 short isoform, given by:

```
                                        (SEQ ID NO: 6)
MKDLHSDDNEEESDEVEDNDNDSEMERPVNRGGSRSRRVSLSDGSDSESS

SASSPLHHEPPPPLLKTNNNQILEVKSPIKQSKSDKQIKNGECDKAYLDE

LVELHRRLMTLRERHILQQIVNLIEETGHFHITNTTFDFDLCSLDKTTVR

KLQSYLETSGTS
```

The MLLT3 polypeptides or AF-9 proteins described herein, may comprise 1, 2, 3, 4, 5, 6, 7, 8, 9, 10, 11, 12, 13, 14, 15, or more variant amino acids (or any range derivable therein) and/or be at least 70%, 80%, 85%, 90%, 95%, 98%, 99% or 100% similar or identical (or any range derivable therein) within at least, and/or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO: 3 or 4 or 6.

The MLLT3 polypeptides or AF-9 proteins described herein, may comprise 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO: 3 or 4 or 6. An MLTT3 polypeptide may also be missing such contiguous number of amino acids (and any range derivable therein) from SEQ ID NO:3, 4, or 6. The protein may be truncated or it may be part of a fusion or chimeric protein. In some embodiments, more than one MLLT3 polypeptide type may be used, such as a combination of MLLT3 variant 1, MLLT3 variant 2, and/or MLLT3 short isoform and any combinations thereof. It is contemplated that the combination may be controlled, for example, transcriptionally, such that the ratio of any two polypeptide isoforms in the cell is approximately about 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1 or more, or any range derivable therein.

Nucleic acids encoding the MLLT3 polypeptides or AF-9 proteins described herein, may comprise 1, 2, 3, 4, 5, 6, 7, 8, 9, 10, 11, 12, 13, 14, 15, or more variant nucleotides and/or be at least 70%, 80%, 85%, 90%, 95%, 98%, 99% or 100% similar or identical within at least, and/or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous nucleic acids, or any range derivable therein, of SEQ ID NO: 1 or 2 or 5.

Nucleic acids encoding the MLLT3 polypeptides or AF-9 proteins described herein, may comprise 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous nucleic acids, or any range derivable therein, of SEQ ID NO: 1 or 2 or 5.

In some embodiments, methods involve culturing cells. This may be done at one or more times in the process. For instance, cell may be cultured before transfection/infection, after transfection/infection, before incubating with at least one, two, three, four, or five factor(s) that induces differentiation of cells, and/or using several different differentiation steps each involving a different subset of factors.

In some embodiments, methods involve culturing the hematopoietic stem cell, which may or may not involve co-culturing with mesenchymal stem cell stromal cells. In some instances, the stromal cells are OP9 cells. In particular instances, the stromal cells are OP9-M2 cells.

Some methods involve viral vectors, expression vectors or constructions, plasmids or agents that carry nucleic acids into a cell. In some embodiments, the MLLT3 integrates into the genome of the hematopoietic stem cell due to the vehicle used with the MLLT3. In other embodiments, the MLLT3 does not integrate into the hematopoietic stem cell. In certain embodiments exogenous MLLT3 is expressed by the hematopoietic stem cell. In specific embodiments, the expression is transient. Particular aspects may involve methods in which MLLT3 is introduced into the hematopoietic stem cell by infection with a viral vector. In some cases, the viral vector is a recombinant adeno-associated virus, a recombinant adenovirus, a recombinant lentivirus or a recombinant retrovirus. In other embodiments, MLLT3 is introduced into the hematopoietic stem cell by transfection with a nucleic acid, which may be an mRNA or an expression construct encoding MLLT3. Transfection can be accomplished chemically or by electroporation under certain embodiments. In additional embodiments, a viral vector or expression construct comprises a promoter, an enhancer or both. In some cases, the promoter is an inducible promoter. An inducible promoter may be a hybrid of CMV and Tet Operator as in the plasmid pNL-EGFP/TREPittdU3 (Addgene plasmid no.

18659), a constitutive UbiquitinC promoter as in the plasmid pFUGW (Addgene plasmid no. 14883) or a MNDU3 promoter to achieve higher transient expression. It is contemplated that the viral vector or expression construct comprises a reporter gene or a selectable marker in some embodiments.

In particular embodiments, an MLLT3-introduced cell is differentiated by introducing it into a subject. In specific cases, an MLLT3-introduced cell is differentiated by incubating the cell with at least one or more of the following: stem cell factor, thrombopoietin, a notch ligand, Wnt, bone morphogenic protein, transforming growth factor beta, a fibroblast growth factor, angiopoietin-1, insulin-like growth factor 2, an angiopoietin-like protein, IL-10, c-kit ligand, progesterone, AM580 UM171, UM729, StemRegenerin 1, granulocyte colony stimulating factor or macrophage colony stimulating factor. In some examples, the MLLT-3 hematopoietic stem cell that is administered to the subject was obtained from the subject prior to introducing MLLT3 such that the cells are autologous. In other situations, cells are not autologous and are obtained from a different subject than the one who is administered cells that contain MLLT3 or the progeny of such cells.

Methods may also involve generating the hematopoietic stem cell prior to step a) from an induced pluripotent stem cell or other pluripotent cells. In some instances, methods may include generating the hematopoietic stem cell prior to step a) from an embryonic stem cell.

In some embodiments, MLLT3-introduced hematopoietic stem cells express MLLT3 and are maintained in an ex vivo culture for at least or at most 1, 2, 3, 4, 5, 6,7, 8, 9, 10, 11, 12 or more days and/or weeks (or any range derivable therein). In particular embodiments, culturing is carried out before differentiation. In certain aspects, the cell culture is in vitro. In certain embodiments, the cultured MLLT3-introduced hematopoietic stem cells undergo cell division without differentiation (self-renewal). In particular instances, cultured MLLT3-introduced hematopoietic stem cells are CD34 positive and CD38 negative. In some embodiments, cultured MLLT3-introduced hematopoietic stem cells are CD90 positive.

It is specifically contemplated that exogenous MLLT3 expression declines or ceases after culturing the MLLT3-introduced hematopoietic stem cells. Exogenous MLLT3 expression refers to expression from an expression vector or viral vector that is introduced MLLT3.

In some instances, hematopoietic stem cells that express or previously expressed exogenous MLLT3 are introduced into a subject, such as one in need of hematopoietic cells or hematopoietic stem cells. It is certainly contemplated that cells introduced into the subject may have previously been hematopoietic stem cells when the MLLT3 was introduced but that they no longer are stem and/or progenitor cells at the time they are introduced into the subject. In certain embodiments, hematopoietic stem cells engraft into the subject's bone marrow. It is contemplated that prior to administration to the subject, cells are assayed for one or more properties or cell surface markers associated with differentiation into one or more hematopoietic cells.

In some embodiments, there are methods for generating a blood cell comprising a) contacting a hematopoietic stem cell with a CDK9 kinase inhibitor; and b) differentiating the CDK9 kinase inhibitor-contacted cell. In some embodiments the amount of the CDK9 kinase inhibitor may be qualified as an effective amount. An "effective amount of a CDK9 kinase inhibitor" means an amount that promotes and/or extends expansion of hematopoietic stem cells in vitro. CDK9 is the kinase present in pTEFb (positive transcription elongation factor b) that is the main regulator of RNApol2 elongation. MLLT3 is a super elongation complex component, thus also regulating elongation. In other embodiments, there are methods of producing hematopoietic cells comprising obtaining hematopoietic stems cells from a subject; b) contacting at least some of the hematopoietic stem cells with a CDK9 kinase inhibitor; c) culturing CDK9 kinase inhibitor-contacted hematopoietic stem cells to enrich for the hematopoietic stem cells; and, d) exposing the hematopoietic stem cells to conditions that allow the hematopoietic stem cells to differentiate into one or more hematopoietic cells. The term "CDK9 kinase inhibitor-contacted cells" refers to cells that have been contacted with CDK9, as well as the progeny of such cells.

In further embodiments, there are methods of producing hematopoietic cells comprising: a) generating hematopoietic stems cells from embryonic stem cells; b) contacting at least some of the hematopoietic stem cells with a CDK9 kinase inhibitor; c) culturing hematopoietic stem cells that were contacted with a CDK9 kinase inhibitor to enrich for the hematopoietic stem cells; and, d) exposing the hematopoietic stem cells to conditions that promote differentiation of the hematopoietic stem cells into one or more hematopoietic cells.

Some embodiments involve methods for providing hematopoietic cells to a subject comprising: a) obtaining hematopoietic stems cells from the subject; b) contacting at least some of the hematopoietic stem cells with a CDK9 kinase inhibitor; and, c) then introducing the cells into the subject, wherein the cells may or may not be at least partially differentiated following exposure to the CDK9 kinase inhibitor.

In additional embodiments, there are methods for providing hematopoietic cells to a subject comprising: a) generating induced pluripotent stems cells (iPSCs) from the subject; b) generating hematopoietic stems cells from the iPSCs; c) contacting at least some of the hematopoietic stem cells with a CDK9 kinase inhibitor; and, d) providing the cells to the subject, wherein the cells may or may not be at least partially differentiated following exposure of CDK9 kinase inhibitor.

CDK9 kinase inhibitors include, but are not limited to, flavopiridol, KM05283, 5,6-dichlorobenzimidazone-1-β-D-ribofuranoside (DRB), LDC000067, SNS-032 (BMS-387032), Dinaciclib (SCH727965), AT7519, P276-00, AZD5438, PHA-767491, PHA-793887, Purvalanol B, and LY2857785. In some embodiments, the CDK9 kinase inhibitor is flavopiridol.

In some embodiments, the concentration of the CDK9 kinase inhibitor is about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nM, μM, or mM (or any range derivable therein). In additional embodiments, the cell is incubated with the CDK9 kinase inhibitor for up to, not more than, or for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200 hours and/or days (or any range derivable therein).

In certain embodiments, a subject in need of hematopoietic cells or hematopoietic stem cells is diagnosed with, is suspected of having or is at risk for developing at least one of a non-nutritional (hemolytic, aplastic or other) anemias, a blood cancer (a lymphoma, leukemia or myeloma), a malignant immunoproliferative disease, a coagulation, purpura or other hemorrhagic condition, an infection-related blood disease, a bacterium-related blood disease, protozoan-related blood disease or an immune system regulation-related blood disease.

In certain aspects, a subject in need of hematopoietic cells or hematopoietic stem cells is diagnosed with, is suspected of having or is at risk for developing a non-nutritional anemia selected from acanthocytosis, acute posthemorrhagic anemia, alpha-thalassemia, anemia, anemia of chronic disease, anemia in kidney disease and dialysis, anemia of prematurity, aplastic anemia, autoimmune hemolytic anemia, beta-thalassemia, diamond-blackfan anemia, congenital dyserythropoietic anemia, drug-induced autoimmune hemolytic anemia, drug-induced nonautoimmune hemolytic anemia, glucose-6-phosphate dehydrogenase deficiency, hemoglobinopathy, hemolytic anemia, congenital hemolytic anemia, fanconi anemia, hereditary spherocytosis, hereditary elliptocytosis, hereditary pyropoikilocytosis, acquired hemolytic anemia, cold hemagglutinin disease, paroxysmal cold hemoglobinuria, hemolytic-uremic syndrome, hereditary persistence of fetal hemoglobin, hereditary stomatocytosis, hexokinase deficiency, hyperanaemia, hypochromic anemia, ineffective erythropoiesis, macrocytic anemia, megaloblastic anemia, microangiopathic hemolytic anemia, minkowski-chauffard syndrome, myelophthisic anemia, neuroacanthocytosis, chorea acanthocytosis, non sideropenic hypochromic anaemia, normocytic anemia, paroxysmal nocturnal hemoglobinuria, pyruvate kinase deficiency, rh deficiency syndrome, sickle-cell disease, sideroblastic anemia, southeast asian ovalocytosis, spur cell hemolytic anemia, thalassemia, triosephosphate isomerase deficiency and warm autoimmune hemolytic anemia.

In yet other embodiments, a subject in need of hematopoietic cells or hematopoietic stem cells is diagnosed with, is suspected of having or is at risk for developing a lymphoma selected from hodgkin lymphoma, non-hodgkin lymphoma, anaplastic large cell lymphoma, angioimmunoblastic t-cell lymphoma, hepatosplenic t-cell lymphoma, b-cell lymphoma, reticuloendotheliosis, reticulosis, microglioma, diffuse large b-cell lymphoma, follicular lymphoma, mucosa-associated lymphatic tissue lymphoma, b-cell chronic lymphocytic leukemia, mantle cell lymphoma, burkitt lymphoma, mediastinal large b cell lymphoma, waldenström's macroglobulinemia, nodal marginal zone b cell lymphoma, splenic marginal zone lymphoma, intravascular large b-cell lymphoma, primary effusion lymphoma, lymphomatoid granulomatosis and nodular lymphocyte predominant hodgkin's lymphoma.

In still other aspects, a subject in need of hematopoietic cells or hematopoietic stem cells is diagnosed with, is suspected of having or is at risk for developing a leukemia selected from plasma cell leukemia, acute erythraemia and erythroleukaemia, acute erythremic myelosis, acute erythroid leukemia, heilmeyer-schöner disease, acute megakaryoblastic leukemia, mast cell leukemia, panmyelosis, acute panmyelosis with myelofibrosis, lymphosarcoma cell leukemia, acute leukemia of unspecified cell type, blastic phase chronic myelogenous leukemia, stem cell leukemia, chronic leukemia of unspecified cell type, subacute leukemia of unspecified cell type, accelerated phase chronic myelogenous leukemia, acute myeloid leukemia, polycythemia vera, acute promyelocytic leukemia, acute basophilic leukemia, acute eosinophilic leukemia, acute lymphoblastic leukemia, acute monocytic leukemia, acute myeloblastic leukemia with maturation, acute myeloid dendritic cell leukemia, adult t-cell leukemia/lymphoma, aggressive nk-cell leukemia, b-cell prolymphocytic leukemia, b-cell chronic lymphocytic leukemia, b-cell leukemia, chronic myelogenous leukemia, chronic myelomonocytic leukemia, chronic neutrophilic leukemia, hairy cell leukemia and chronic idiopathic myelofibrosis.

In particular aspects, a subject in need of hematopoietic cells or hematopoietic stem cells is diagnosed with, is suspected of having or is at risk for developing a myeloma selected from multiple myeloma, kahler's disease, myelomatosis, solitary myeloma, plasma cell leukemia, plasmacytoma, extramedullary, malignant plasma cell tumour NOS and plasmacytoma NOS.

In particular embodiments, a subject in need of hematopoietic cells or hematopoietic stem cells is diagnosed with, is suspected of having or is at risk for developing a malignant immunoproliferative disease selected from monoclonal gammopathy, angiocentric immunoproliferative lesion, lymphoid granulomatosis, angioimmunoblastic lymphadenopathy, t-gamma lymphoproliferative disease, waldenström's macroglobulinaemia, alpha heavy chain disease, gamma heavy chain disease, franklin's disease, immunoproliferative small intestinal disease, mediterranean disease and malignant immunoproliferative disease.

In still other embodiments, a subject in need of hematopoietic cells or hematopoietic stem cells is diagnosed with, is suspected of having or is at risk for developing a coagulation, purpura, or other hemorrhagic conditions selected from disseminated intravascular coagulation (DIC, defibrination syndrome), protein c deficiency, protein s deficiency, thrombocytosis, idiopathic thrombocytopenic purpura, recurrent thrombosis, hemophilia, hemophilia a, hemophilia b, hemophilia c, von willebrand disease, antiphospholipid syndrome, thrombocytopenia, glanzmann's thrombasthenia, wiskott-aldrich syndrome and thrombotic thrombocytopenic purpura.

In further aspects, a subject in need of hematopoietic cells or hematopoietic stem cells is diagnosed with, is suspected of having or is at risk for developing a clostridium infection, cholera infection, *E. coli* 0157:h7 infection or typhoid fever. In other aspects, a subject in need of hematopoietic cells or hematopoietic stem cells is diagnosed with, is suspected of having or is at risk for developing a leishmania infection, malaria infection (plasmodium infection) or toxoplasmosis. In additional embodiments, a subject in need of hematopoietic cells or hematopoietic stem cells is diagnosed with, is suspected of having or is at risk for developing a immune system regulation-related disease selected from hereditary hypogammaglobulinemia, nonfamilial hypogammaglobulinemia, selective deficiency of immunoglobulin A [IgA], selective deficiency of immunoglobulin G [IgG] subclasses, selective deficiency of immunoglobulin m [IgM], immunodeficiency with increased immunoglobulin M [IgM], antibody deficiency with near-normal immunoglobulins or with hyperimmunoglobulinemia, and transient hypogammaglobulinemia of infancy.

In some embodiments, at least or at most 20, 25, 30, 35, 40, 45, 50, 55, 60, 65, 70, 75, 80, 85, 90, 95,996, 97, 98, 99, 100 percent (or any range derivable therein) of the cells are viable either post-introduction of MLLT3, pre- and/or post-culturing, pre- and/or post self-renewing, and/or pre- and/or post differentiation. In some cases, introduction of MLLT3 provides this viability after 1, 2, 3, 4, 5, 6, 7, 8, 9, 10, 11, 12, 13, 14, 15, 16, 17. 18. 19, 20 or more rounds or generations in culture (or any range derivable therein).

In some embodiments, MLLT3 or a CDK kinase inhibitor increases the viability or the number of hematopoietic stem cell by about or at least about 5%, 10%, 15%, 20%, 25%, 30%, 35%, 40%, 45%, 50%, 55%, 60%, 65%, 70%, 75%, 80%, 85%, 90%, 100%, 110%, 120%, 130%, 140%, 150%, 160%, 170%, 180%, 190%, 200%, 250%, 300%, 350%, 400%, 500%, (and any range derivable therein) and or by about or at least about 2×, 3×, 4×, 5×, 10×, 20×, 30×, 40×, 50×, 60×, 70×, 80×, 90×, 100×, 110×, 120×, 130×, 140×, 150×, 160×, 170×, 180×, 190×, 200×, 210×, 220×, 230×, 240×, 250×, 260×, 270×, 280×, 290×, 300×, 310×, 320×, 330×, 340×, 350×, 360×, 370×, 380×, 390×, 400×, 410×, 420×, 430×, 440×, 450×, 460×, 470×, 480×, 490×, 500×, 600×, 700×, 800×, 900×, 1000×, 1100×, 1200×, 1300×, 1400×, 1500×, 1600×, 1700×, 1800×, 1900×, 2000×, 3000×, 4000×, 5000×, 6000×, 7000×, 8000×, 9000×, 10,000× or more, or any range derivable therein. The comparison point is with respect to the absence of MLLT3 or CDK9 kinase inhibitor.

In some embodiments, MLLT3-introduced hematopoietic stem cells are differentiated to adult beta-globin expressing erythroid cells.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Compositions and Methods

Figure 1:
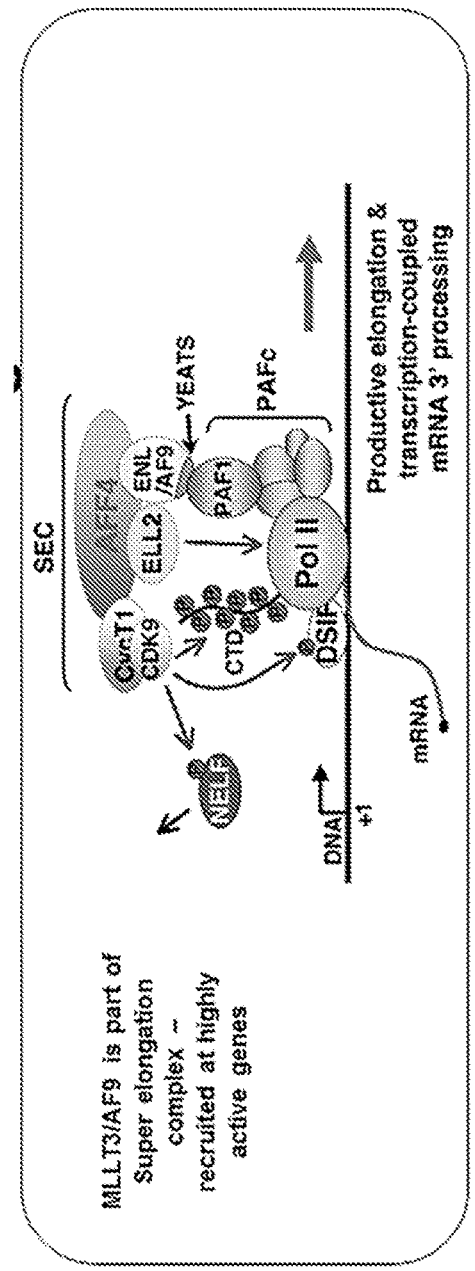
FIG. 1. MLLT3 (AF9) is part of the Super Elongation complex.

Transient MLLT3 overexpression in culture may be used to expand human HSCs in vitro, and thereby improve the efficiency and safety of HSC transplantation. In addition, we showed that MLLT3 overexpression in human PSC-differentiation cultures helps prolong the maintenance of immunophenotypic HSPCs and clonogenic progenitors in culture. Thus restoring proper levels of MLLT3 expression in PSC-derived hematopoietic stem/progenitor cells (HSPCs) may help create better in vitro models for PSC (pluripotent stem cells) derived hematopoiesis, and enable "disease-in-a-dish" studies for hematological diseases using patient specific iPSCs or other pluripotent cells.

II. Nucleic Acids

In certain embodiments, there are recombinant nucleic acids encoding the proteins, polypeptides, or peptides described herein. Polynucleotides contemplated for use in methods and compositions include those encoding MLLT3.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or fewer in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above).

In particular embodiments, there are isolated nucleic acid segments and recombinant vectors incorporating nucleic acid sequences that encode a polypeptides (e.g., MLLT3 and AF-9, including variants 1 and 2 and isoforms and b, respectively) that allow the maintenance and expansion of HSCs, HSPCs, iPSC-HSPCs and human embryonic stem cell (hESC)-HSPCs in culture. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide can comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Expression vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used to target hematopoietic cells and hematopoietic stem cells to allow the maintenance and expansion of HSCs, HSPCs, iPSC-HSPCs and hESC-HSPCs in culture.

In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

Viral Vectors

Adenoviral Infection

One method for delivery of the recombinant DNA involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a recombinant gene construct that has been cloned therein.

The adenovirus vector may be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the some starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells.

Retroviral Infection

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants.

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

AAV Infection

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin et al., 1984; Laughlin et al., 1986; Lebkowski et al., 1988; McLaughlin et al., 1988), which means it is applicable for use with the present methods and compositions. Details concerning the generation and use of rAAV vectors are described in U.S. Pat. Nos. 5,139,941 and 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Shelling and Smith, 1994; Yoder et al., 1994; Zhou et al., 1994; Hermonat and Muzyczka, 1984; Tratschin et al., 1985; McLaughlin et al., 1988) and genes involved in human diseases (Flotte et al., 1992; Ohi et al., 1990; Walsh et al., 1994; Wei et al., 1994). Recently, an AAV vector has been approved for phase I human trials for the treatment of cystic fibrosis.

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994a; Clark et al., 1995). Cell lines carrying the rAAV DNA as an integrated provirus can also be used (Flotte et al., 1995).

Protamine

Protamine may also be used to form a complex with an expression construct. Such complexes may then be formulated with the lipid compositions described above for administration to a cell. Protamines are small highly basic nucleoproteins associated with DNA. Their use in the delivery of nucleic acids is described in U.S. Pat. No. 5,187,260, which is incorporated by reference. U.S. patent application Ser. No. 10/391,068 (filed Mar. 24, 2003), which pertains to methods and compositions for increasing transduction efficiency of a viral vector by complexing the viral vector with a protamine molecule, is specifically incorporated by reference herein.

Non-Viral Delivery

In addition to viral delivery of the expression vectors encoding transcription factors, the following are additional methods of recombinant gene delivery to a given host cell and are thus considered in the present invention.

Lipid Mediated Transformation

In a further embodiment of the invention, an expression vector may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Advances in lipid formulations have improved the efficiency of gene transfer in vivo (Smyth-Templeton et al., 1997; WO 98/07408). A novel lipid formulation composed of an equimolar ratio of 1,2-bis(oleoyloxy)-3-(trimethyl ammonio)propane (DOTAP) and cholesterol significantly enhances systemic in vivo gene transfer, approximately 150-fold. The DOTAP:cholesterol lipid formulation is said to form a unique structure termed a "sandwich liposome". This formulation is reported to "sandwich" DNA between an invaginated bi-layer or 'vase' structure. Beneficial characteristics of these lipid structures include a positive colloidal stabilization by cholesterol, two dimensional DNA packing and increased serum stability.

In further embodiments, the liposome is further defined as a nanoparticle. A "nanoparticle" is defined herein to refer to a submicron particle. The submicron particle can be of any size. For example, the nanoparticle may have a diameter of from about 0.1, 1, 10, 100, 300, 500, 700, 1000 nanometers or greater. The nanoparticles that are administered to a subject may be of more than one size.

Any method known to those of ordinary skill in the art can be used to produce nanoparticles. In some embodiments, the nanoparticles are extruded during the production process. Exemplary information pertaining to the production of nanoparticles can be found in U.S. Patent App. Pub. No. 20050143336, U.S. Patent App. Pub. No. 20030223938, U.S. Patent App. Pub. No. 20030147966, and U.S. Ser. No. 60/661,680, each of which is herein specifically incorporated by reference into this section.

In certain embodiments, an anti-inflammatory agent is administered with the lipid to prevent or reduce inflammation secondary to administration of a lipid:nucleic acid complex. For example, the anti-inflammatory agent may be a non-steroidal anti-inflammatory agent, a salicylate, an anti-rheumatic agent, a steroid, or an immunosuppressive agent. Information pertaining to administration of anti-inflammatory agents in conjunction with lipid-nucleic acid complexes can be found in U.S. Patent App. Pub. No. 20050143336, which is herein specifically incorporated by reference.

Synthesis of DOTAP:Chol nanoparticles is by any method known to those of ordinary skill in the art. For example, the method can be in accordance with that set forth in Chada et al., 2003, or Templeton et al., 1997, both of which are herein specifically incorporated by reference. DOTAP:Chol-DNA complexes were prepared fresh two to three hours prior to injection in mice.

One of ordinary skill in the art would be familiar with use of liposomes or lipid formulation to entrap nucleic acid sequences. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use subcutaneous, intradermal, intratumoral, or intracranial injection to avoid the toxicity and stability problems associated with cationic lipids in the circulation. The interaction of liposomes and plasma proteins is responsible for the disparity between the efficiency of in vitro (Felgner et al., 1987) and in vivo gene transfer (Zhu et al., 1993; Solodin et al., 1995; Liu et al., 1995; Thierry et al., 1995; Tsukamoto et al., 1995; Aksentijevich et al., 1996).

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Liposomal encapsulation has resulted in a lower toxicity and a longer serum half-life for such compounds (Gabizon et al., 1990). Numerous disease treatments are using lipid based gene transfer strategies to enhance conventional or establish novel therapies.

The liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

In some embodiments, instead of introducing MLLT3 into a hematopoietic stem cell, cells are exposed to or incubated with a CDK9 kinase inhibitor. Flavipirold, (Alvocidib) is a flavonoid alkaloid CDK9 kinase inhibitor under clinical development for the treatment of acute myeloid leukemia, arthritis and atherosclerotic plaque formation. The target of Flavopiridol is CDK9, a component of the positive transcription elongation factor P-TEFb. MLLT3 is a member of the super-elongation complex that recruits and modulates p-TEFb. Other possible and more or less selective CDK9 inhibitors that potentially could be used to modulate HSPC expansion in culture are KM05283 and 5,6-dichlorobenz-imidazone-1β-D-ribofuranoside (DRB), LDC000067, SNS-032 (BMS-387032), Dinaciclib (SCH727965), AT7519, P276-00, AZD5438, PHA-767491, PHA-793887, Purvalanol B, and LY2857785. Any combination of these CDK9 kinase inhibitors may be used. Moreover, it is contemplated in some embodiments that MLLT3 may be introduced into a cell that is or was also exposed to a CDK9 kinase inhibitor. In some embodiments, one or more of these CDK9 kinase inhibitors may be excluded.

Host and Target Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" or target cells refers to a prokaryotic or eukaryotic cell, and it includes any transformable organism that is capable of replicating a vector or expressing a heterologous gene encoded by a vector. A host or target cell can, and has been, used as a recipient for vectors or viruses. A host or target cell may be "transfected" or "transformed," which refers to a process by which exogenous nucleic acid, such as a recombinant protein-encoding sequence, is transferred or introduced into the host or target cell. A transformed cell includes the primary subject cell and its progeny. In some aspects a target cell is a liver cell, a hepatocyte or a liver sinusoidal endothelial cell.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with an embodiment to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

III. Proteinaceous Compositions

In some embodiments, a nucleic acid encoding an MLLT3 polypeptide or AF-9 protein that allows the maintenance and expansion of HSCs, HSPCs, iPSC-HSPCs and hESC-HSPCs in culture may be isolated. The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids (see Table, below).

| Codon Table | | |
|---|---|---|
| Amino Acids | | Codons |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent. For example, certain amino acids may be substituted for other amino acids in a protein structure without appreciable loss of interactive binding capacity or ability of a transcription factor to drive transcription. Structures such as, for example, MLLT3 polypeptide or AF-9 protein may have amino acid substituted to maintain its function. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

Polypeptides and Polypeptide Production

Embodiments involve an MLLT3 polypeptide or AF-9 protein that allows the maintenance and expansion of HSCs, HSPCs, iPSC-HSPCs and hESC-HSPCs in culture. In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate expression vector followed by culture of the expression vector under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

In a certain aspects an MLLT3 polypeptide or AF-9 protein that allows the maintenance and expansion of HSCs, HSPCs, iPSC-HSPCs and hESC-HSPCs in culture which has at least 85% identity, at least 90% identity, at least 95% identity, or at least 97-99% identity, including all values and ranges there between, to a sequence selected over the length of the fragment sequence is included in the disclosed methods. In yet other aspects, an MLLT3 polypeptide or AF-9 protein that allows the maintenance and expansion of HSCs, HSPCs, iPSC-HSPCs and hESC-HSPCs in culture comprises substantially some or all of the active portion a protein which has at least 85% identity, at least 90% identity, at least 95% identity, or at least 97-99% identity, including all values and ranges there between, to a sequence selected over the length of the fragment sequence.

Other Polypeptides: Differentiation Agents and Cell Surface Markers

In the Examples, certain cell surface markers are used to sort cells that can be used in embodiments discussed herein. 1, 2, 3, 4, 5, 6, 7, 8, 9, 10 or more of these markers (or any range derivable therein) may be used to isolate, enrich, or purify cells that can be used in embodiments described herein.

Also, a number of differentiation agents are described herein. 1, 2, 3, 4, 5, 6, 7, 8, 9, 10 or more of these differentiation agents (or any range derivable therein) may be used alone or in combination with other differentiation agents.

Moreover, the amount of a CDK9 kinase inhibitor that cells can be exposed to can be about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 or more, or any range derivable therein, nM, µM, mM, or ng or µg.

Cells may be contacted with a CDK kinase inhibitor for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, and/or 1, 2, 3, 4, 5 weeks. Cells may be contacted with a CDK9 kinase inhibitor and then cultured without the CDK9 kinase inhibitor, but then subsequently exposed again or multiple times to the CDK9 kinase inhibitor IV. Methods of Treatment As discussed above, the compositions and methods of using these compositions of cells can treat an blood disease or disorder in a subject or prevent a blood disease in a subject having, suspected of having, or at risk of developing an blood disease or disorder. In certain embodiments, a subject is treated with autologous cells.

The therapeutic compositions are administered in a manner compatible with the dosage formulation, and in such amount as will be therapeutically effective. The quantity to be administered depends on the subject to be treated. Precise amounts of active ingredient required to be administered depend on the judgment of the practitioner. Suitable regimes for initial administration and boosters are also variable, but are typified by an initial administration followed by subsequent administrations.

Compositions of the current methods may be administered to patients via any route used to introduce cells to patients. Such routes include, but are not limited to, infusion of the cells or transplantation of the cells. In some embodiments, the cells are providing intravenously to the patient.

The manner of application may be varied widely. Any of the conventional methods for administration of a polypeptide therapeutic are applicable. These are believed to include oral application on a solid physiologically acceptable base or in a physiologically acceptable infusion, transfusion, dispersion, parenterally, by injection and the like. The dosage of the composition will depend on the route of administration and will vary according to the size and health of the subject. In one treatment scheme, the patient receives a dose of the composition comprising hematopoietic cells in a dose or composition or separately in multiple formulations or compositions, every week for three weeks and then every first week for an additional 1, 2, 3, 4, 5, 6, 7, 8, 9, 10, 11, or 12 months. In other aspects the patient or subject receives two injections spaced a minimum or 7 days apart within 1-2 months and then every week for an additional 1, 2, 3, 4, 5, 6, 7, 8, 9, 10, 11, or 12 months or every first week of the month for an additional 1, 2, 3, 4, 5, 6, 7, 8, 9, 10, 11, or 12 months.

In certain instances, it will be desirable to have multiple administrations of the composition, e.g., 2, 3, 4, 5, 6 or more administrations. The administrations can be at 1, 2, 3, 4, 5, 6, 7, 8, 9, 10, 11, 12 or more week intervals, including all ranges there between.

Combination Therapy

The compositions and related methods, may also be used in combination with the administration of antibacterial, antiviral, antifungal, antibiotic, antineoplastic or chemotherapeutic agent effective strategies or traditional immunomodulatory therapies.

In one aspect, it is contemplated that an MLLT3 polypeptide or AF-9 protein expanded HSC is used in conjunction with immunosuppressants. Similarly, cells exposed to a CDK9 kinase inhibitor may be similarly used in a combination therapy. In other aspects, a therapy is used in conjunction with disease-modifying agents, symptom controlling agents, or agents to improve compromised function. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations of therapy may be employed, for example, an MLLT3 polypeptide or AF-9 protein expanded HSC, immunosuppressant therapy, disease-modifying agents, symptom controlling agents, or agents to improve compromised function is "A" and a conventional or standard autoimmune disorder treatment is "B":

| | | | | |
|---|---|---|---|---|
| A/B/A | B/A/B | B/B/A | A/A/B | A/B/B |
| B/A/A | A/B/B/B | B/A/B/B | B/B/B/A | B/B/A/B |
| A/A/B/B | A/B/A/B | A/B/B/A | B/B/A/A | B/A/B/A |
| B/A/A/B | A/A/A/B | B/A/A/A | A/B/A/A | A/A/B/A |

Administration of any cell compositions to a patient/subject will follow general protocols for the administration of such compounds, taking into account the toxicity, if any, of the composition. It is expected that the treatment cycles would be repeated as necessary. It is also contemplated that various standard therapies, such as hydration, may be applied in combination with the described therapy.

General Pharmaceutical Compositions

In some embodiments, pharmaceutical compositions are administered to a subject. Different aspects may involve administering an effective amount of a composition to a subject. In some embodiments, an effective amount or quantity or number of an MLLT3 polypeptide or AF-9 protein expanded HSC is administered to a subject. Alternatively, an effective amount or quantity or number of an MLLT3 polypeptide or AF-9 protein expanded HSC may be given to a patient as a preventative treatment. Additionally, such compositions can be administered in combination with an adjuvant or if immune tolerance is desired, an immunosuppressant. Such compositions will generally be dissolved or dispersed in a pharmaceutically acceptable carrier or aqueous medium. All of these embodiments may be similarly used with cells exposed to a CDK9 kinase inhibitor.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents, immunosuppressants and immunotherapeutics, can also be incorporated into the compositions.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to infusion, oral, nasal, or buccal administration. Alternatively, administration may be by orthotopic, intradermal, subcutaneous, intramuscular, intraperitoneal, intranasal, or intravenous injection. In certain embodiments, a immunotherapeutic composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired. At least or at most 1, 2, 3, 4, 5, 6, 7, 8, 9, or 10 unit doses (or any range derivable therein) may be administered to patients.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 2:
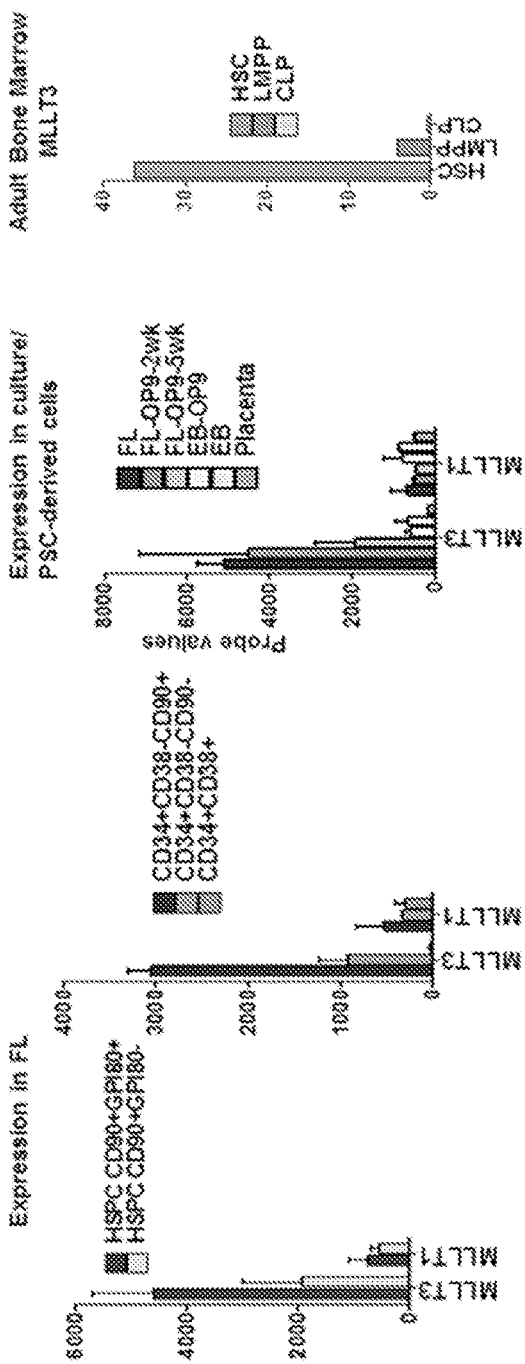
FIG. 2. Transcription elongation factor MLLT3 is highly enriched in self-renewing HSCs.

MLLT3 (AF9) is part of the Super Elongation complex. (FIG. 1) Microarray analysis shows that the gene MLLT3 was highly expressed in the most HSC enriched fraction of the fetal liver (FL) HSPC population, the CD45+CD38-/loCD90+GPI80+ cells. MLLT3 expression rapidly drops with cell differentiation to committed progenitors, in parallel with potential of FL-HSPC for long term engraftment. The inventors also collected data from HSPC populations at different developmental stages. MLLT3 expression is detected at low levels in first trimester hemogenic endothelium placenta, where a population of immature pre-HSC first emerges but, with limited engrafted potential, and is first detected at robust levels in FL HSPC. MLLT3 is also detected in adult bone marrow HSPC, and its expression decreases with cell differentiation, as assessed by RNA-seq. High MLLT3 expression in the human HSPC population is confined to the most self-renewal and long-term engrafting fraction at all developmental stages. (FIG. 2)

Figure 3:
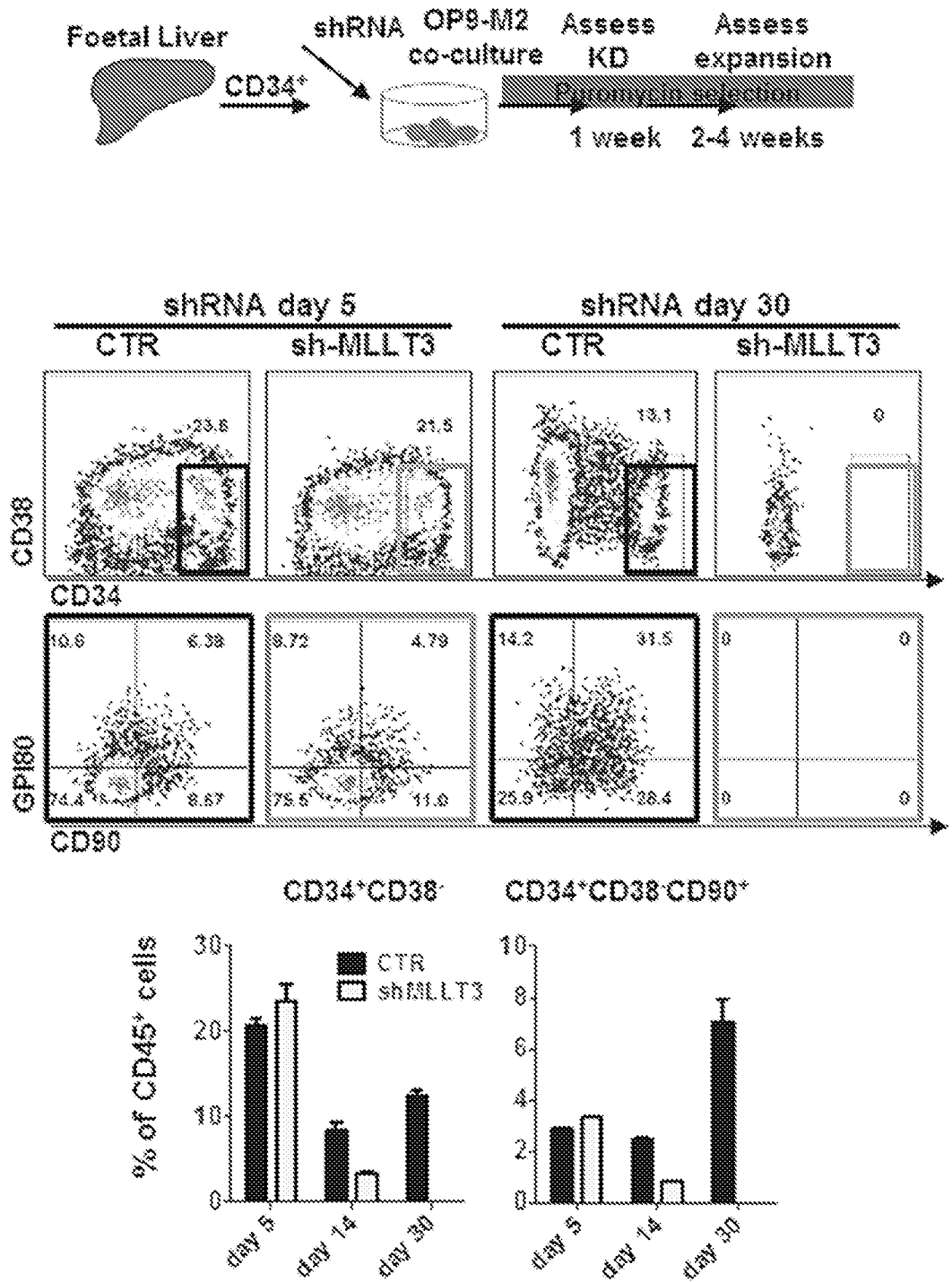
FIG. 3. Loss of MLLT3 disrupts HSPC maintenance in vitro.

Using a lentiviral shRNA vector, the inventors knocked down MLLT3 expression into FL GPI80+HSPC and assayed their self renewal by measuring the ability of those cells to maintain a population of HSPC on bone marrow stroma (OP9-M2). HSPC in which MLLT3 expression was reduced were unable to sustain long term HSPC proliferation. (FIG. 3)

Figure 4:
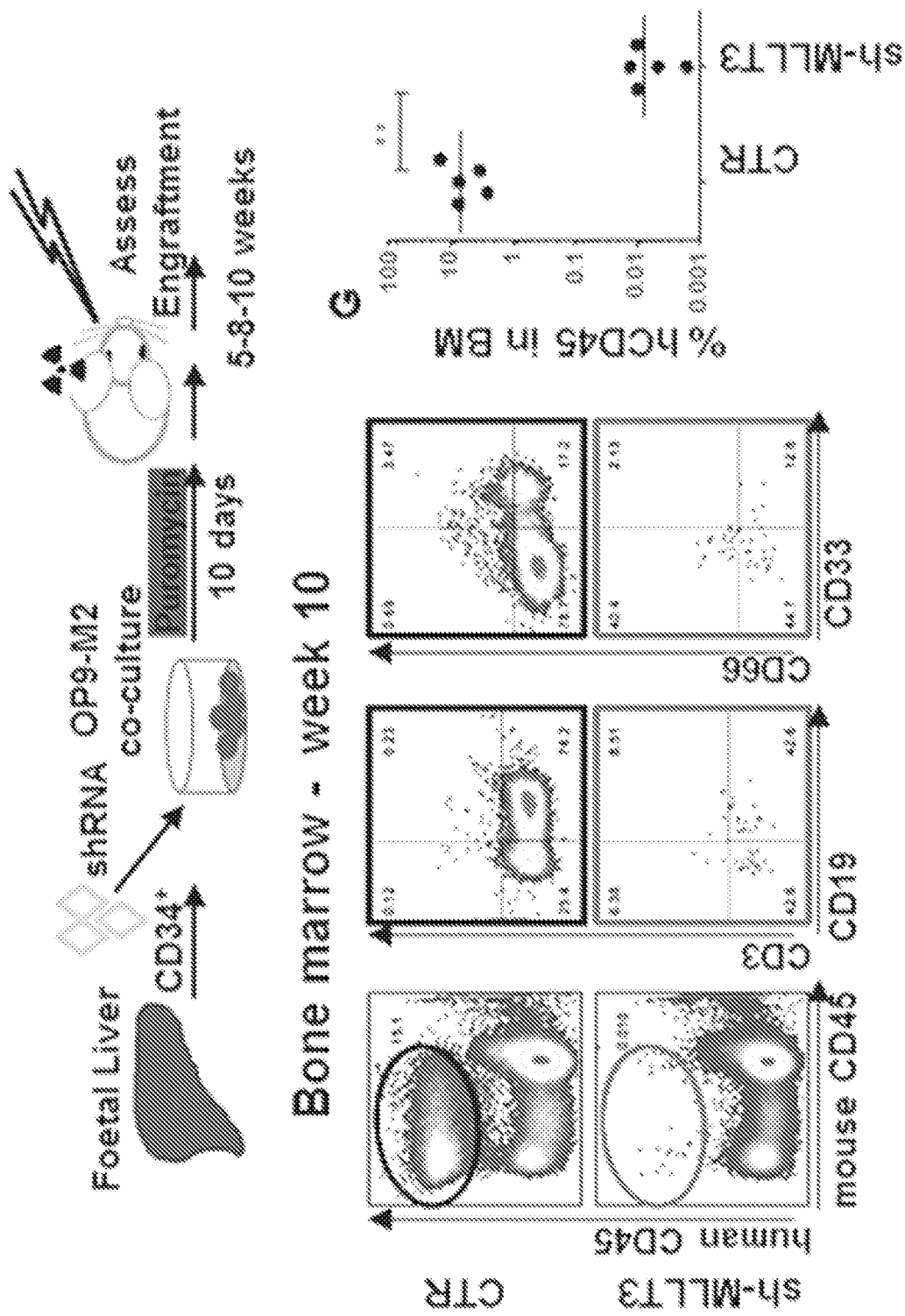
FIG. 4. Loss of MLLT3 disrupts HSPC engraftment in vivo.

The inventors also tested whether the engraftment potential of cells with reduced MLLT3 expression is affected. The inventors transplanted sub-lethally irradiated NSG mice with FL-HSPC after MLLT3 or control lentiviral shRNA infection. MLLT3 knockdown showed severely curtailed ability to engraft mouse bone marrow. High MLLT3 expression in FL-HSPC is therefore necessary for the cells to self-renew in vitro and to engraft a host. (FIG. 4)

Figure 5:
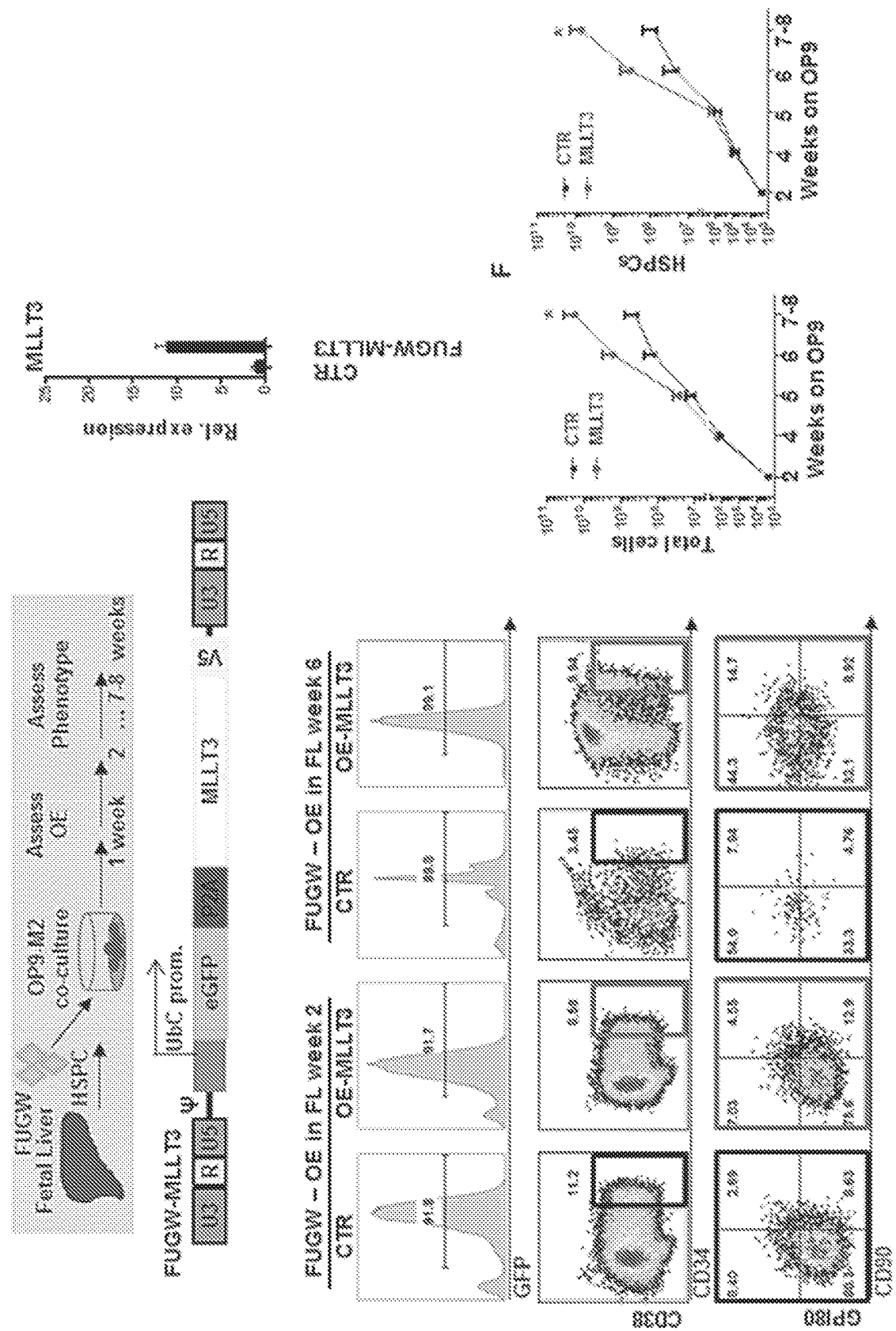
FIG. 5. MLLT3 overexpression promotes HSPC maintenance in culture.

Although HSPC can be expanded in vitro for several weeks on OP9-M2 stroma, the engraftment ability of these cells can only be maintained shortly, and is ultimately lost, despite the presence of phenotypic HSPC in the expanded populations. The inventors observed that MLLT3 expression within the phenotypic FL-HSPC population is also reduced over time in culture. The inventors assayed whether sustained MLLT3 expression could sustain the ability of cultured FL-HSPC to maintain or expand, and retain engraftment ability. The inventors designed a MLLT3 expression vector driven by a cellular promoter (UbC), mildly active in FL-HSPC. The overexpression in FL-HSPC achieved a MLLT3 expression comparable with the levels found in uncultured GPI-80+FL-HSPC. Enforced MLLT3 expression led to a robust expansion of FL-HSPC in culture as compared to the control. (FIG. 5)

Figure 6:
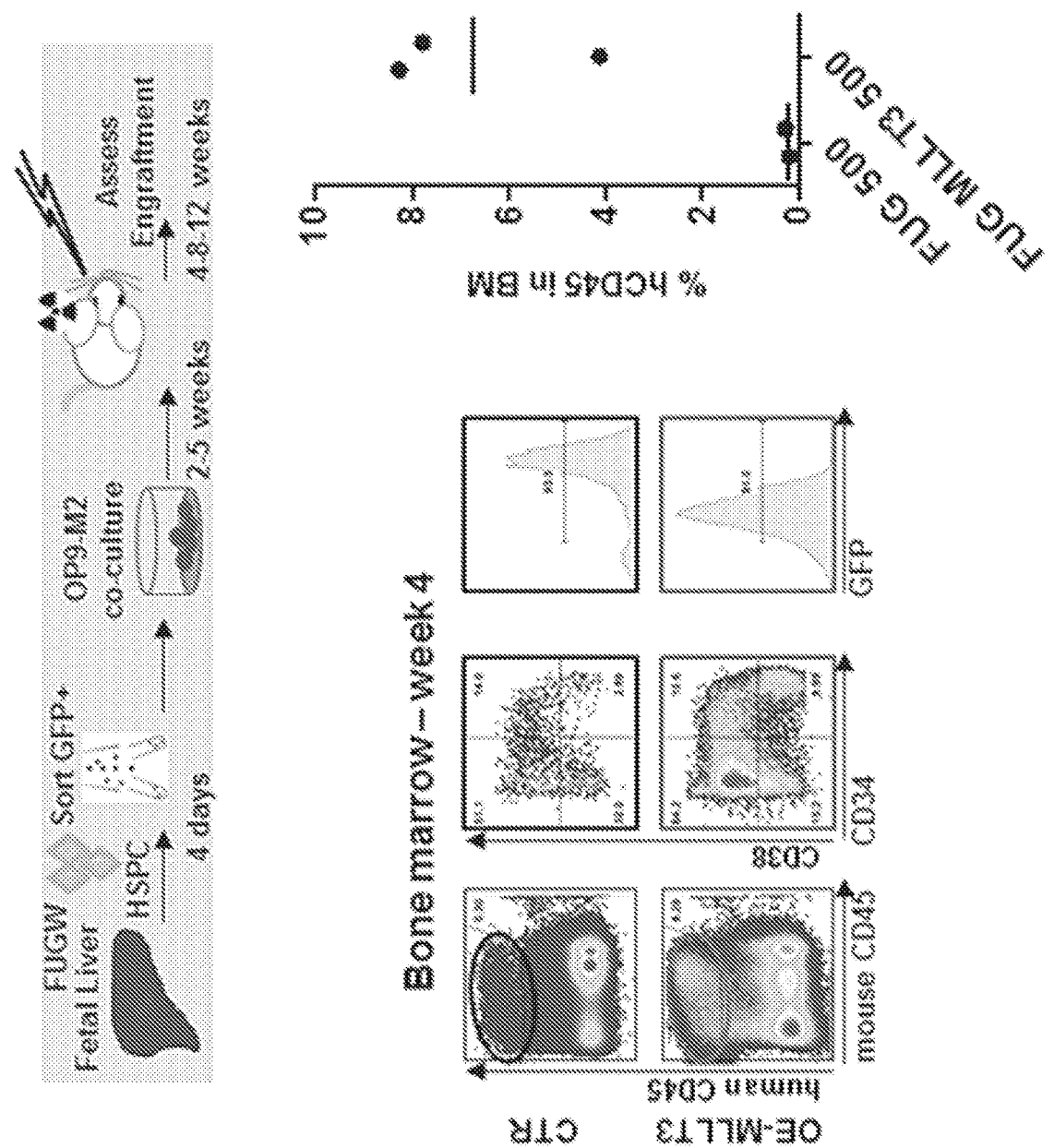
FIG. 6. Restoring MLLT3 expression in culture may improve engraftment and self-renewal ability in vivo.

The inventors also tested whether the MLLT3-overexpressing cells would maintain engraftment ability. The inventors transplanted sub-lethally irradiated NSG mice with FL-HSPC after MLLT3 or control lentiviral overexpression vector. MLLT3 overexpression seems to sustain engraftment ability of the expanded cells in the short term. (FIG. 6)

Figure 7:
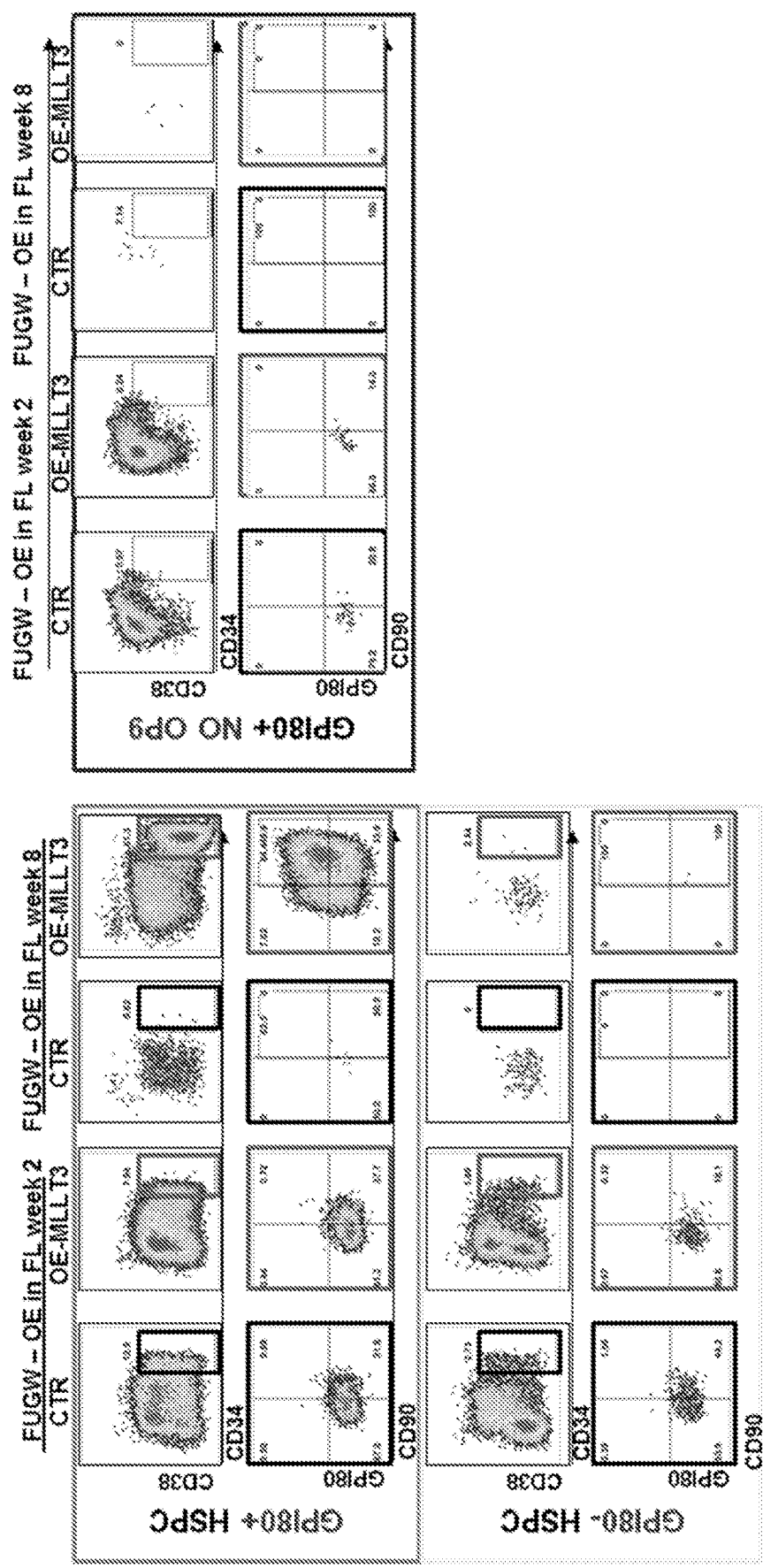
FIG. 7. MLLT3 overexpression does not convert progenitors to HSCs, or make HSCs niche independent.

Conversely, MLLT3 overexpression in GPI80–FL-HSPC, a population with poor and time-limited expansion potential in vitro and unable to long term engraftment, did not improve in vitro expansion ability of these cells, confirming that MLLT3-mediated effect is limited to the context of undifferentiated self-renewing HSPC. To exclude the possibility that MLLT3 overexpression alone would confer niche-independent expansion features to the cells, thereby carrying potential for leukemic transformation, the inventors cultured MLLT3 overexpressing in GPI80+FL-HSPC in absence of OP9 stroma, and observed the expected inability to maintain HSPC even in the short term. These results altogether show that MLLT3 sustained expression within the context of a self-renewing HSPC can maintain and expand for longer FL-HSPC without the appearance of un-controlled proliferation. (FIG. 7)

Figure 8:
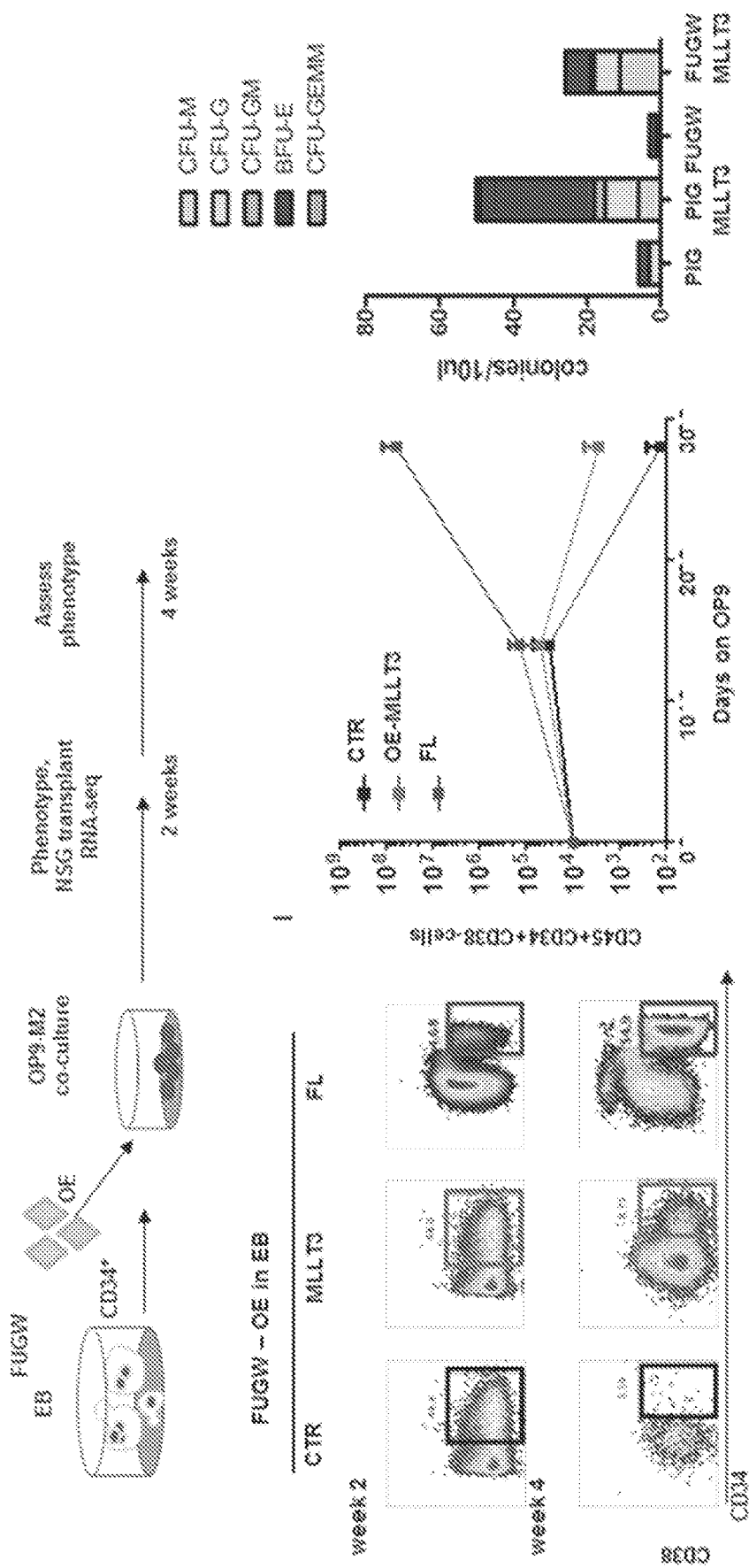
FIG. 8. MLLT3 overexpression in hESC-HSPCs enhances HSPC expansion and maintains CFU potential.

Pluripotent stem cell (PSC)-derived hematopoietic cell generation represents a promising avenue, as a cell source for therapy. Currently phenotypical HSPC can be generated in vitro from embryonic stem cells, but those cells do not possess sustained in vitro expansion ability of in vivo engraftment ability. MLLT3 was found to be at low expression in PSC-derived HSPC, therefore the inventors tested whether the enforced MLLT3 expression in PSC-HSPC could ameliorate their expansion behavior. The inventors found that PSC-HSPC expressing MLLT3 were able to sustain for longer in vitro expansion and maintain the hematopoietic precursor clonogenic ability in culture. (FIG. 8)

Figure 9:
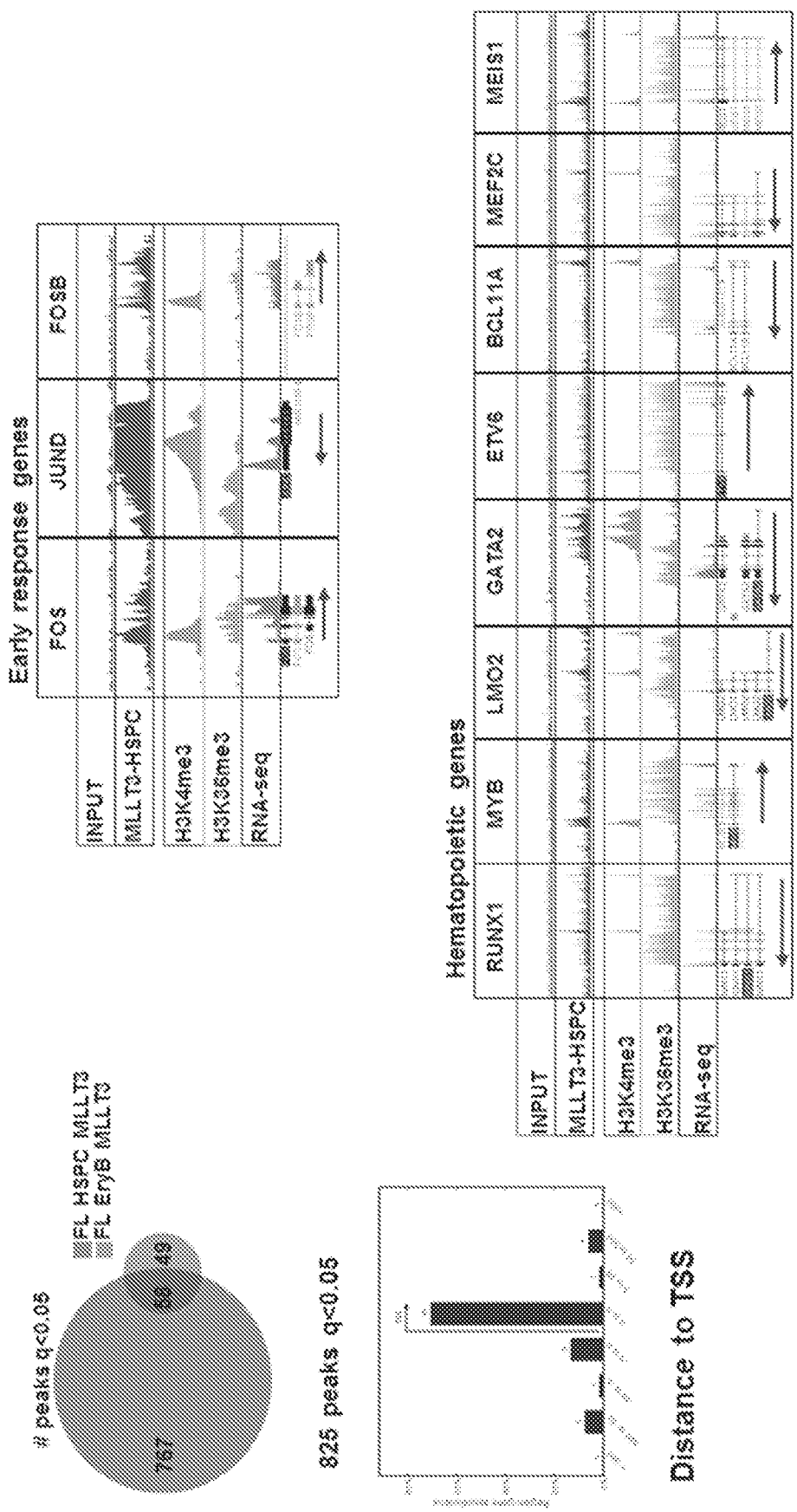
FIG. 9. MLLT3 binds to the TSS/gene body of HSC regulators in human fetal liver HSPCs.

By using chromatin immunoprecipitation of sorted FL-HSPC, the inventors observe binding of MLLT3 at 825 genomic sites. The large majority of the binding occurs in regions of transcriptional initiation and within the first 5 kb downstream of it, consistent with the loading of the MLLT3 at actively expressed genes. MLLT3 binding is enriched at highly transcribed genes, although not directly correlated to expression levels overall; only a subset of highly transcribed genes display MLLT3 binding. (FIG. 9)

To address the possibility that MLLT3 would be needed to sustain HSC self-renewal transcriptional network, the inventors analyzed which genes were specifically bound by MLLT3. The inventors observed high MLLT3 binding genes were enriched in genes with a function in chromatin organization (e.g. histone genes), general transcription factors (e.g. JUND, FOS) and hematopoietic transcription factors (e.g. BCL11A, MEIS1) as well as other housekeeping genes (e.g. HNRNPs, snoRNAs, HSP90, UBC). These genes are globally highly expressed in FL-HSPC. Also a moderate but significant binding was observed at transcription factors that are essential for the generation and function of self-renewing HSC, such as RUNX1, MYB, MYC, LMO2, GATA2, ETV6, FLI1 LYL1, HOXA9 and MEF2C. The inventors therefore hypothesized that MLLT3 controls HSC self-renewal by sustaining the expression at proper levels of key hematopoietic transcription factors. (FIG. 9)

Figure 10:
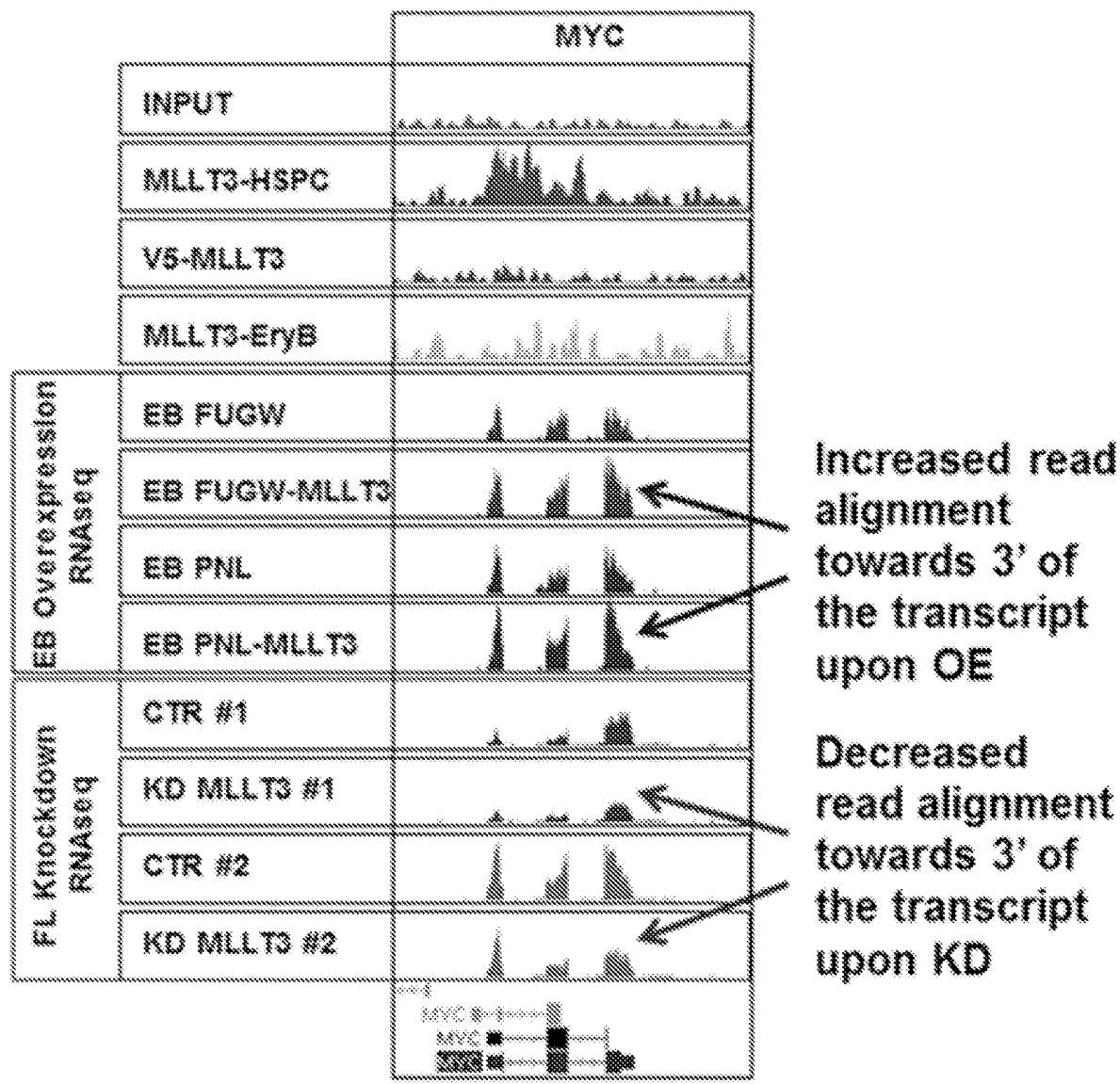
FIG. 10. MLLT3 may regulate transcription elongation in human HSPCs.
Figure 11:
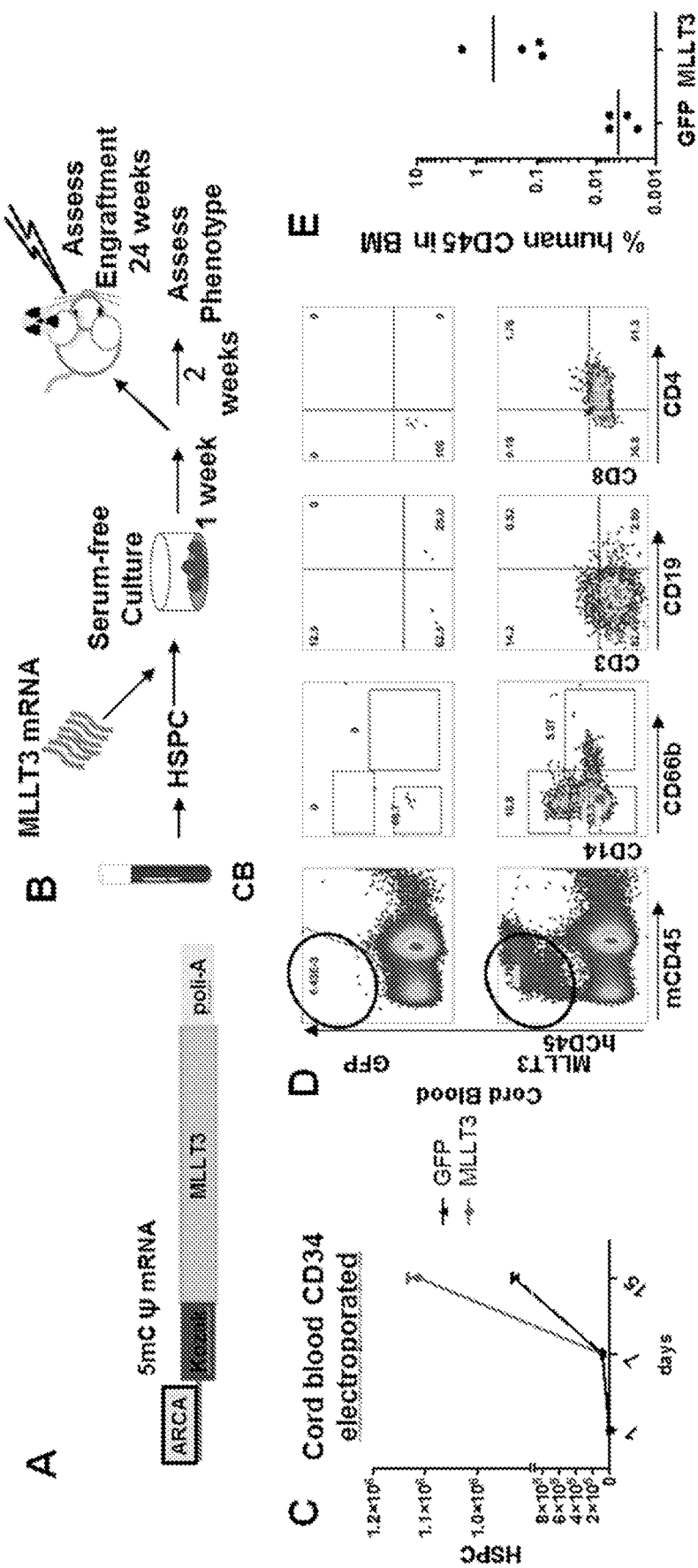
FIG. 11A-E. Introduction of MLLT3 mRNA into cord blood HSC transiently by electroporation of modified mRNA improves HSPC expansion and engraftment. A-B. Transient, non-genotoxic overexpression of MLLT3 is achieved by electroporation of in vitro synthesized mRNA modified with pseudouridine (Ψ) and/or 5-methylcytidine (m5C) in place of the corresponding U or C nucleosides. RNA is capped at the 5' with the anti-reverse cap analog (ARCA) m27,3'-OG[5']ppp[5'] for efficient ribosomal recognition. Modification are aimed at avoiding innate cellular immune responses mediated by external RNA sensors and improving translation efficiency. GFP mRNA-induced fluorescence can be detected up to 5 days after electroporation (data not shown). C. CB HSPC also showed sustained HSPC expansion in culture and D-E. engraftment ability, when transplanted in sublethally irradiated NSG mice 7 days after the electroporation. Improved engraftment is shown by the presence of cell expression human CD45 that can differentiate to myeloid (CD14 and CD66B) or lymphoid (CD3, CD19, CD4/8) lineages.

MLLT3 as a component of the super elongation complex may be regulating the ability of the RNA polymerase II to elongate the engaged transcript. RNAseq data show as the transcription factor cMYC, bound by MLLT3 seem to be regulated in the amount of transcript that efficiently completes the transcription process. In this example the inventors show how the amount of reads that align with the end of the MLLT3 gene is increased in the instance of enforced MLLT3 expression in PSC-HSPC, and is diminished by MLLT3 knockdown in FL-HSPC. MLLT3 may regulate efficient elongation at its bound genes. (FIG. 10).

Example 2

Figure 14:
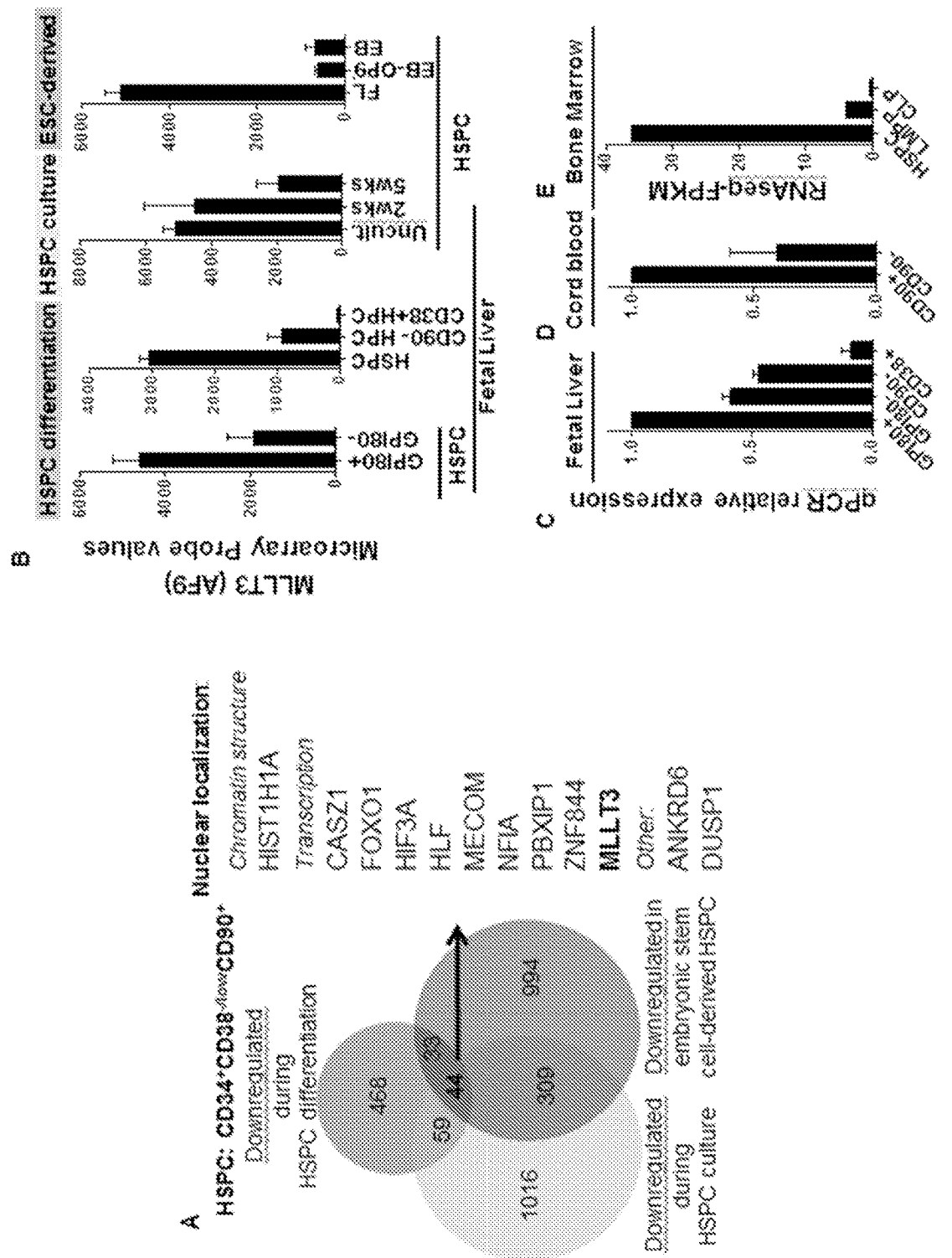
FIG. 14A-E. MLLT3 is highly expressed in self-renewing human HSPC from multiple sources. (A) Venn diagram representing the intersection of microarray-generated gene expression data obtained from previous studies identifying genes that are enriched in self-renewing human HSC (see main text). Hematopoietic stem and progenitor cells (HSPC) are hereby defined phenotypically as CD45/43+CD34+CD38−/lowCD90+ cells. We selected genes that were downregulated upon differentiation of FL GPI80+HSC to non-self-renewing progenitors (Prashad et al.) (pink), genes downregulated during HSPC culture on OP9M2 stroma for 5 weeks (Magnusson et al.) (green), and genes that were poorly induced in phenotypic HSPC derived from (described in Dou et al.) (purple). From the 44 common genes and 12 genes encoding proteins that are localized in the nucleus, MLLT3 was chosen as a candidate for further studies. (B) Histograms plotting the MLLT3 probe values for the above mentioned microarray datasets. HPC, hematopoietic progenitor cells. EB, embryoid bodies-derived HSPC. EB-OP9 embryoid bodies-derived HSPC cultured for 2 weeks on OP9. q-RT PCR validation of the microarray data in fetal liver (C) and cord blood (D) HSPC populations. Expression relative to GAPDH, normalized for the first sample of each plot. (E) RNAseq analysis of MLLT3 expression in adult bone marrow HSC (lin−CD45+CD34+CD38-CD90+ CD45RA−) versus lymphoid-primed multipotent progenitor (LMPP; lin−CD34+CD38+CD10−CD45RA+CD123int CD115−CD62Lhi) and common lymphoid progenitors (CLP; lin−CD34+CD38+CD10+CD45RA+), data from Casero et al.

We tested whether introduction of MLLT3 mRNA into cord blood HSC transiently by electroporation of modified mRNA improved HSPC expansion and engraftment. In FIG. 14, we show it did. Transient, non-genotoxic overexpression of MLLT3 was achieved by electroporation of in vitro synthesized mRNA modified with pseudouridine ($\Psi$) and/or 5-methylcytidine (m5C) in place of the corresponding U or C nucleosides (FIG. 14A-B). RNA is capped at the 5' with the anti-reverse cap analog (ARCA) m27,3'-OG[5']ppp[5'] for efficient ribosomal recognition. Modification are aimed at avoiding innate cellular immune responses mediated by external RNA sensors and improving translation efficiency. GFP mRNA-induced fluorescence can be detected up to 5 days after electroporation (data not shown). CB HSPC also showed sustained HSPC expansion in culture and D-E. engraftment ability, when transplanted in sublethally irradiated NSG mice 7 days after the electroporation (FIG. 14C). Improved engraftment was shown by the presence of cell expression human CD45 that can differentiate to myeloid (CD14 and CD66B) or lymphoid (CD3, CD19, CD4/8) lineages.

Example 3

Figure 12:
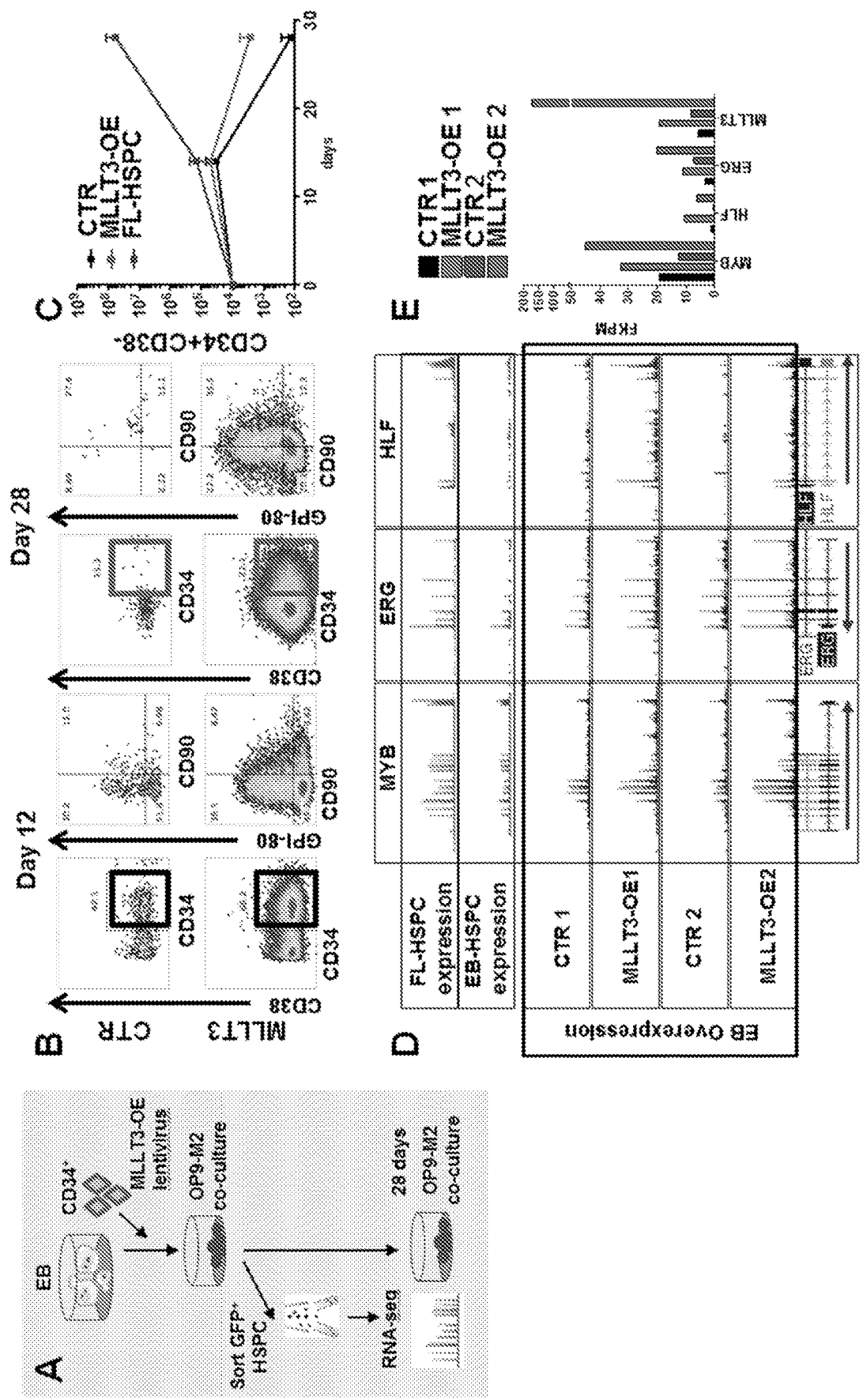
FIG. 12A-E. MLLT3 overexpression expands hESC derived HSPC. A. CD34+ cells are generated in vitro from HESC using embryoid body differentiation and infected with MLLT3-OE lentivirus or CTR lentivirus. B-C. MLLT3 overexpression causes improved maintenance of the population containing phenotypic HSPC (CD34+CD38−) in OP9M2 co-culture. D-E. RNAseq analysis of HSPC population after 2 weeks on OP9M2 co-culture shows MLLT3-bound hematopoietic genes (MYB ERG and HLF), whose expression is defective in EB-HSPC, that are significantly upregulated by MLLT3 overexpression.

We evaluated whether MLLT3 overexpression expands hESC derived HSPC. In FIG. 12, we show this can be achieved. CD34+ cells are generated in vitro from HESC using embryoid body differentiation and infected with MLLT3-OE lentivirus or CTR lentivirus (FIG. 12A). MLLT3 overexpression caused improved maintenance of the population containing phenotypic HSPC (CD34+ CD38–) in OP9M2 co-culture (FIG. 12B-C). DRNAseq analysis of HSPC population after 2 weeks on OP9M2 co-culture showed MLLT3-bound hematopoietic genes (MYB ERG and HLF), whose expression was defective in EB-HSPC, that were significantly upregulated by MLLT3 overexpression (FIG. 12D-E).

Example 4

Figure 13:
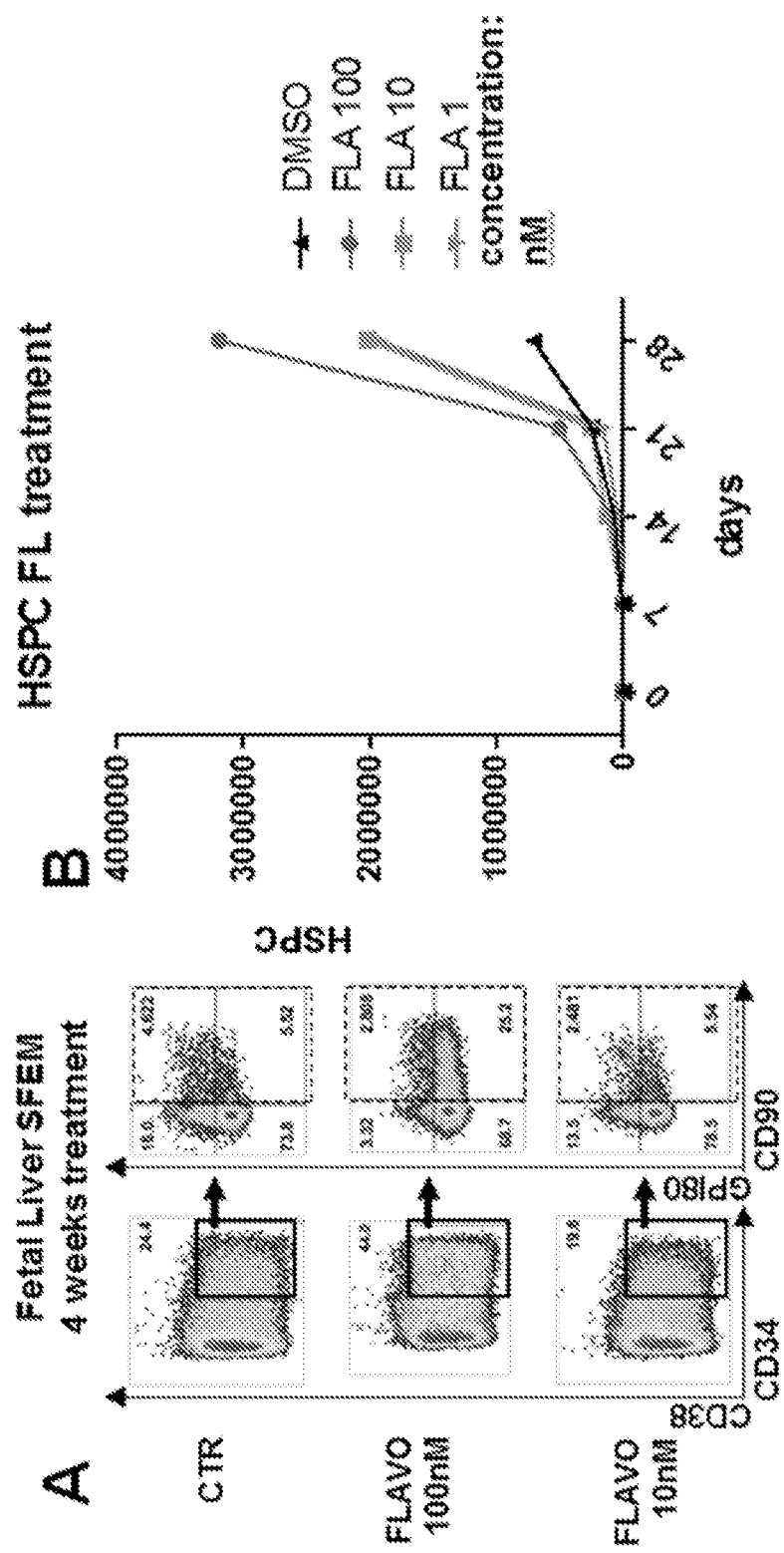
FIG. 13A-B. MLLT3 overexpression expands hESC derived HSPC. A. CD34+ cells are generated in vitro from HESC using embryoid body differentiation and infected with MLLT3-OE lentivirus or CTR lentivirus. B. MLLT3 overexpression causes improved maintenance of the population containing phenotypic HSPC (CD34+CD38−) in OP9M2 co-culture. D-E. RNAseq analysis of HSPC population after 2 weeks on OP9M2 co-culture shows MLLT3-bound hematopoietic genes (MYB ERG and HLF), whose expression is defective in EB-HSPC, that are significantly upregulated by MLLT3 overexpression.

We investigated whether an effect on transcription elongation by a different factor might change the effect. We determined that Treatment of human HSPC with Flavopiridol, a regulator of transcription elongation machinery, expands HSPC in culture. A. Flavopiridol treatment of human HSPC at 100 nM sustained HSPC expansion in culture, similarly to MLLT3 overexpression, as shown by FIG. 13A. FACS analysis of HSPC population, and calculating total HSPC expansion over time in culture is shown in FIG. 13B.

Example 5

We set out to identify the unique gene regulatory mechanisms in human HSCs that underlie their self-renewal ability, in order to overcome current limitations in the expansion of true human HSCs in culture. We identified MLLT3 as a novel HSC self-renewal regulator that governs transcription elongation process in genes that are central for human HSC function.

To define the regulatory mechanisms that sustain human HSC self-renewal and engraftment ability we intersected transcriptional data from previous studies comparing a highly self-renewing, engraftable population of human fetal liver HSCs with their immediate daughter cells, and immunophenotypically similar but functionally impaired HSPC generated in culture or expanded in culture. This analysis included 1) genes enriched in the GPI80+FL-HSPC (CD34+ CD38$^{-/lo}$CD90+GPI80+) that were downregulated in the GPI80− progeny that lack self-renewal/engraftment ability[3]; 2) genes expressed in FL-HSPC whose expression is dysregulated upon extended culture (5 weeks), when immunophenotypic HSPC have lost engraftment ability[4]; and 3) HSPC genes whose expression is defective in hematopoietic progenitors generated in vitro from human embryonic stem cells (hESC)[5] (FIGS. 14 A and B). After intersecting dysregulated genes shared between these non-self-renewing populations (44 genes) and selecting genes encoding nuclear factors, a list of 12 candidates was obtained. Among those, MLLT3 arose as a promising candidate as an upstream regulator of HSC self-renewal network. MLLT3 gene encodes a protein AF9, which has been described as a component of the super elongation complex (SEC)[6, 7] and/or the Dot1 complex (DotCom)[8-10], potentially affecting a broad transcriptional program through RNApol2 function.

We further validated MLLT3 expression in human hematopoietic tissues from different sources (FIG. 14C). We confirmed by q-RT-PCR that MLLT3 was highly expressed in the HSC enriched fraction of the fetal liver (FL), (CD45+ CD38$^{-/lo}$CD90+GPI80+ cells), and that MLLT3 expression drops upon differentiation to committed progenitors. Similarly, MLLT3 was also detected at high levels in cord blood (CD45+CD38$^{-/lo}$CD90+) HSPC and its expression decreased with differentiation (FIG. 14D). Analysis of RNA-seq data confirmed that also in adult bone marrow, the HSC fraction expresses high levels of MLLT3 as compared to differentiated progeny (FIG. 14E).

Figure 15:
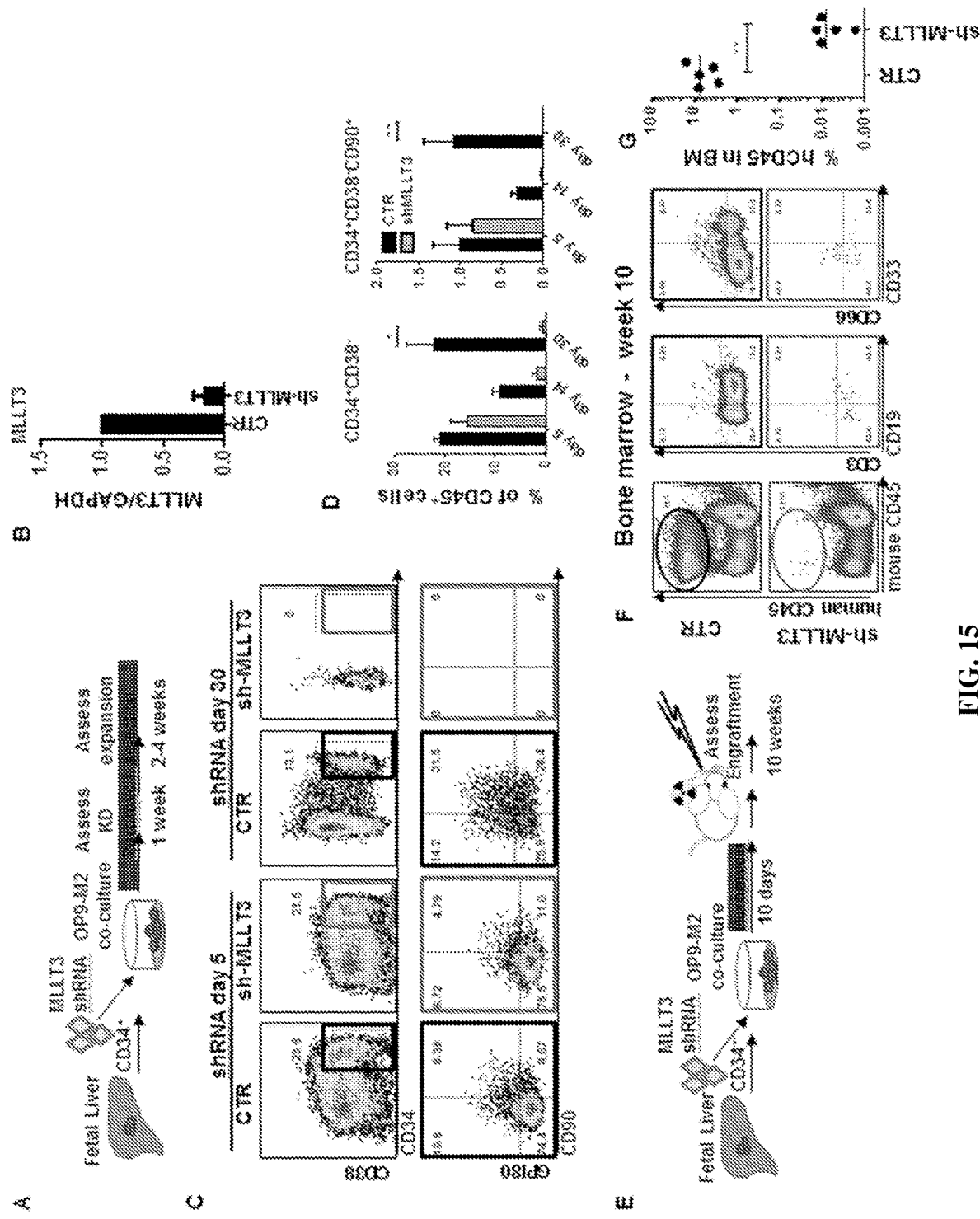
FIG. 15A-G. Expression is necessary for HSPC self-renewal and engraftment (A) Schematic showing the strategy for lentiviral shRNA knockdown of MLLT3 in FL-HSPC. (B) Knockdown is confirmed using q-RT-PCR 1 week post-infection (mean+/−SD shown from n=2 different FL samples). (E) Representative FACS plots 5 and 30 days after MLLT3 knockdown. (D) Quantification of HSPC subsets in empty-vector (CTR) and MLLT3 shRNA infected cells after 5, 14 and 30 days in culture (mean and SEM, n=3). Statistical significance was assessed using Student's t-test (*p<0.05, p<0.01). (E) Schematic showing the transplantation strategy with MLLT3 knockdown FL-HSPC. (F) Representative FACS plots from mouse BM 10 weeks post-transplantation assessing human CD45+ cells and multi-lineage engraftment (CD19 and CD3 for B- and T-lymphoid, and CD66 and CD33 for myeloid). (G) Quantification of human engraftment as evidenced by the presence of human CD45 positive cells, 5 mice per condition from 2 independent experiments. Individual values and mean are shown and statistical significance was assessed using Student's t-test (p<0.01).
Figure 16:
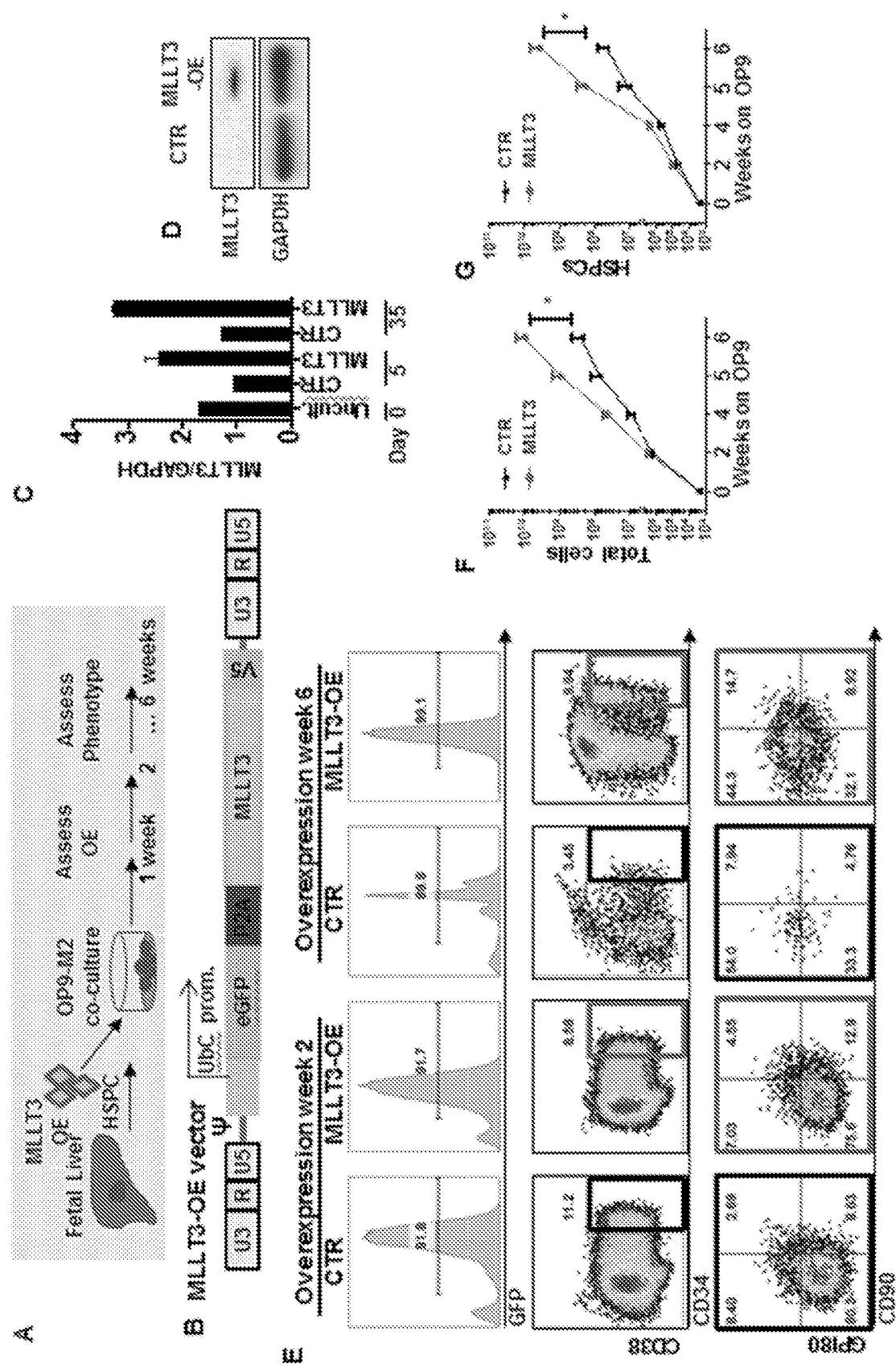
FIG. 16A-G. Overexpression of MLLT3 enhances proliferative potential in FL-HSPC. (A) Schematic showing the strategy for constitutive lentiviral overexpression of MLLT3 in FL-HSPC. (B) Diagram showing the FUGW lentiviral overexpression construct encoding MLLT3 (UbC=Ubiquitin C. P2A=cleavage sequence. V5=V5 peptide tag). (C) q-RT-PCR confirming modest overexpression in transduced HSPC sorted 5 days and 35 days post-infection (2 donors). (D) Western blot showing MLLT3 overexpression in HSPC expanded for 4 weeks in culture. (E) Representative FACS plots of FUGW empty vector (CTR), MLLT3-overexpressing FL-HSPC. Expansion of total live cells (F) or HSPC (G) transduced with MLLT3-overexpression vectors or empty vector control (CTR). Mean and SEM values from n=6 independent experiments; statistical significance was assessed using the Student's t-test (*p<0.05).
Figure 20:
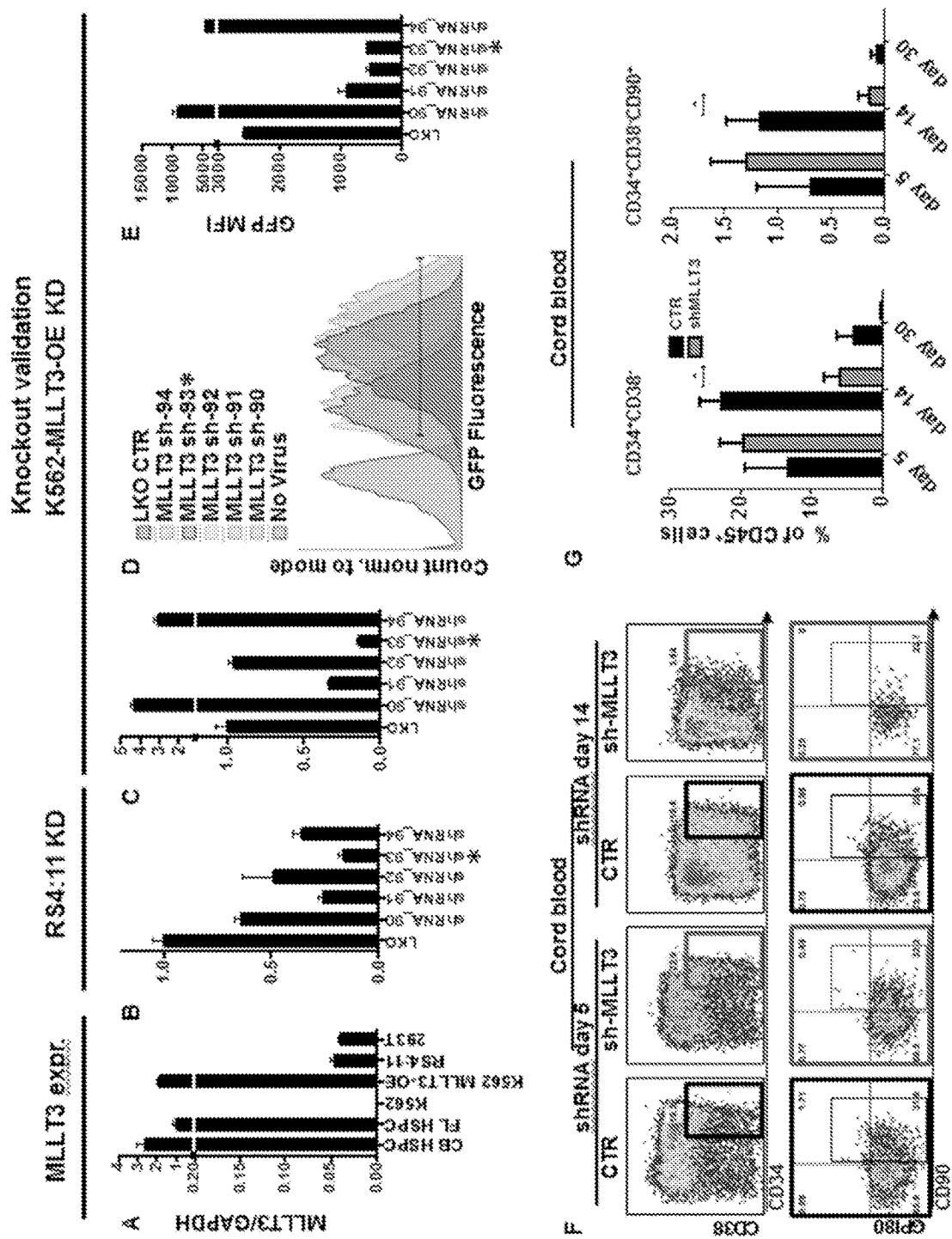
FIG. 20A-G. Validation of MLLT3 knockdown in cell lines and cord blood HSPC. (A) MLLT3 expression by q-RT-PCR in the indicated samples shows the highest expression in cord blood (CB) and fetal liver (FL) HSPC. Among the cell lines RS4:11 and 293T have low but detectable expression and K562 expression is undetectable. K562 stably infected with FUGW-MLLT3 vector (see FIG. 16B) and sorted for GFP (K562 MLLT3-OE) is also assessed, showing similar levels as FL and CB HSPC. Knockdown by 5 different clones (TRCN0000005790, TRCN0000005791, TRCN0000005792, TRCN0000005793, TRCN0000005794) from the The RNAi Consortium (TRC) was tested using q-RT-PCR 5 days post infection on RS4:11 (B) and K562 MLLT3-OE (C) (mean+/−SD shown from n=2 infections). Representative FACS plots (D) and quantification (E) of the median fluorescence intensity (MFI) of GFP after MLLT3 knockdown on K562 MLLT3-OE, after background cell fluorescence of non-infected cell is subtracted. * in B-E indicates the clone chosen for functional assessment in this study. (F) Representative FACS plots 5 and 14 days after MLLT3 knockdown in cord blood HSPC. (G) Quantification of HSPC subsets in empty-vector (CTR) and MLLT3 shRNA infected cells after 5, 14 and 30 days in culture (mean and SEM, n=3). Statistical significance was assessed using t-test (*p<0.05).

Based on the HSC enriched expression pattern, we asked whether MLLT3 has a specific function in regulating HSC properties. We used a lentiviral shRNA vector (FIG. 15A) that we had tested for efficiency and specificity by knocking down MLLT3 in MLLT3 expressing cell lines (RS4:11), and in K562 cells infected with a GFP-coupled recombinant MLLT3 (FIG. 20A-D, see methods in Example 3 and FIG. 16B). MLLT3 shRNA number 93 was selected for further functional assays. MLLT3 expression was knocked down in FL GPI80+HSPC and their function was assayed by quantifying the expansion of immunophenotypic HSPC on mouse bone marrow mesenchymal stroma niche (OP9M2), which can provide an exponential expansion of multipotent human HSPC over time[4]. HSPC in which MLLT3 expression was reduced (FIG. 15B) could not be maintained in long-term culture, whilst the control shRNA vector-infected HSPC continued to expand for several weeks (FIG. 15C-D). Similarly, knockdown of MLLT3 in cord blood HSPC also severely impaired their expansion ability in culture (FIG. 20F-G). We also tested whether MLLT3 knockdown affects engraftment potential by transplanting sub-lethally irradiated NSG mice with FL-HSPC transduced with MLLT3 or control lentiviral shRNA and expanded for 10 days in OP9M2 co-culture (FIG. 15E). MLLT3 knockdown resulted in loss of human hematopoietic engraftment in NSG mouse bone marrow (FIG. 15F-G). Thus we concluded that MLLT3 expression is necessary for human HSPC self-renewal in vitro and to engraftment in vivo.

Although immunophenotypic HSPC that retain relatively stable HSC transcriptome can be numerically expanded on stroma co-culture over several weeks, our data show that MLLT3 expression within the HSPC population is reduced over time in culture (FIGS. 14A and B) during which time the cultured HSPC lose engraftment ability[4]. We therefore asked whether sustaining adequate levels of MLLT3 expression in culture using lentiviral overexpression vectors could retain HSC functional properties. MLLT3 overexpression vector driven by a Ubiquitin C promoter was used to achieve stable, physiological level of MLLT3 expression (FIG. 16A-C), comparable with the levels found in uncultured GPI-80+ FL-HSPC. Strikingly, lentiviral overexpression of MLLT3 led to a robust expansion of both FL-HSPC (FIG. 16D-F and FIG. 21E-G) and CB-HSPC (FIG. 21H-M) in culture as compared to the controls, as assessed by cell counts and flow cytometry. These data suggest that maintaining adequate MLLT3 levels in cultured HSPC sustains their self-renewal in culture.

Figure 21:
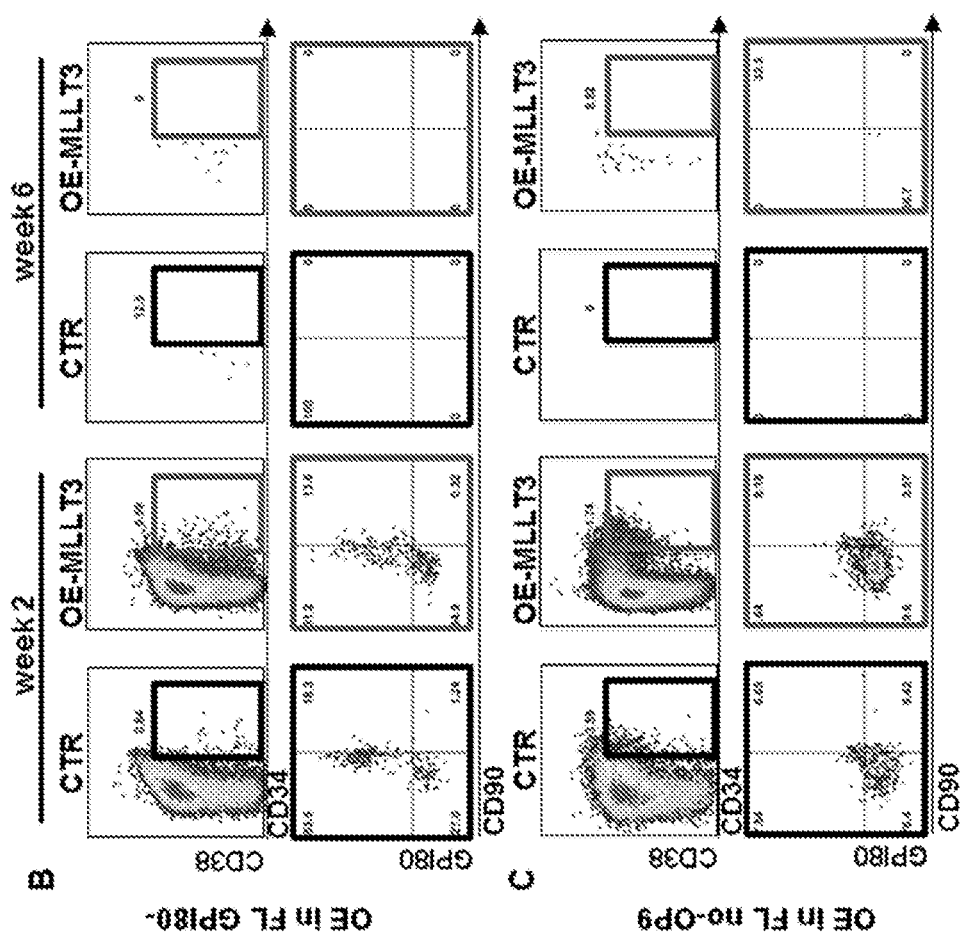
FIG. 21A-G. Overexpression of MLLT3 sustains culture expansion exclusively in HSPC regardless of tissue or culture conditions. (A) Schematic showing the strategy for lentiviral overexpression of MLLT3 in FL-derived GPI80+ HSPC or committed GPI80− progenitors. These populations were sorted apart from the HSPC compartment and infected with CTR or MLLT3-OE vectors. GPI80+HSPC were also seeded in non-supportive HSPC conditions (in stroma-adapted conditions but in absence of OP9M2) to test for stroma dependence of the MLLT3-OE HSPC. Representative FACS plots of FUGW empty vector (CTR), MLLT3-overexpressing FL-HSPC from GPI80-HSPC (B) and GPI80+HSPC in absence of OP9M2. (D) Expansion of HSPC is quantified in all the conditions mentioned above as compared to the GPI80+HSPC transduced with MLLT3-OE or empty vector control (CTR). Results show that the expansion and maintenance of self-renewing population is limited to the context of a self-renewing HSC in supportive culture condition and that MLLT3 does not reprogram or transform HSC or precursors. MLLT3-OE expansion in FL-HSPC is also effective in serum-free media (SS2=Stemspan2) in presence of supportive cytokines as shown by FACS (E), Total cell (F) and HSPC (G) expansion. Similarly MLLT3-OE-results in Cord Blood (CB)-HSPC expansion both on OP9M2 (H-J) and in serum-free medium (K-M) as shown by FACS and cell expansion. Mean and SEM values; statistical significance was assessed using the Student's t-test.
Figure 21:
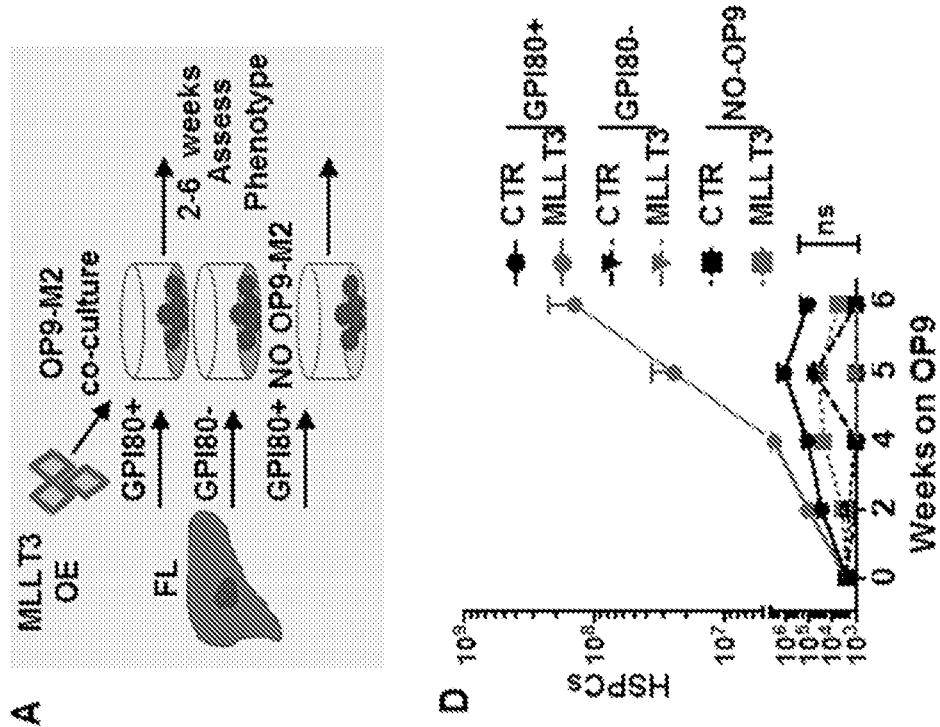
Figure 21:
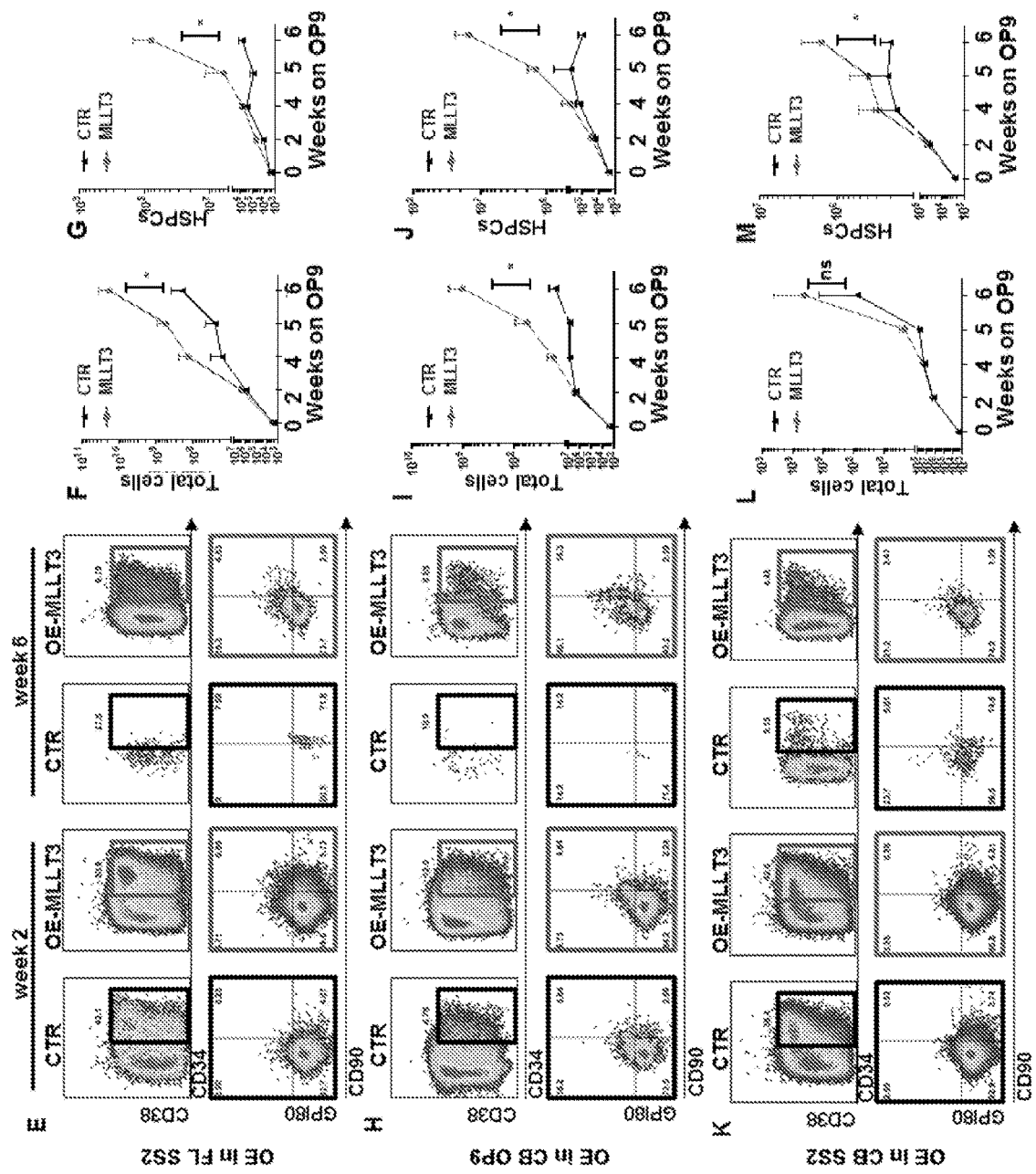

Importantly, MLLT3 overexpression in the immediate progeny of GPI80+HSPC (GPI80−HPC), a population with minimal ex vivo expansion potential and defective long-term engraftment, did not improve their expansion ability. These data imply that MLLT3 does not reprogram progenitors to HSCs, but its effect is limited to the context of undifferentiated, self-renewing HSC (FIGS. 21A-B and D). Moreover, to exclude the possibility that MLLT3 overexpression would confer niche-independent expansion ability to HSPC, carrying potential for leukemic transformation, MLLT3 overexpressing in GPI80+FL-HSPC were cultured in absence of OP9M2 stroma. However, MLLT3 overexpressing HSPC could not be expanded in culture without the OP9 stroma niche, implying that they retain dependence to microenvironmental signals (Figure S3A,C and D).

We also tested the ability of the MLLT3-expanded HSPC to differentiate into all major hematopoietic lineages in vitro. MLLT3-expanded HSPC sorted after 4 weeks expansion could efficiently generate differentiated precursors of erythroid (GlyA+CD71+/−), T-lymphoid (CD4+CD8+), B-lymphoid (CD19+) granulocyte (CD66b+) and monocyte (CD14+) lineages (Figure S4 A-C). The differentiated cell output from MLLT3-OE cultured cells was comparable to freshly isolated FL-HSPC output in each assay. We can thus conclude that FL-HSPC generated by MLLT3-OE preserved the original multilineage hematopoietic differentiation potential. These results altogether show that sustained MLLT3 expression in HSPC can maintain and expand multipotent FL-HSPC longer without the appearance of uncontrolled proliferation or altered differentiation potential.

In recent years additional protocols to culture HSC in xeno-free conditions have been developed, that are more suitable for translation to clinical application. We thus tested whether the MLLT3-mediated HSPC expansion would hold effective in the context of the most refined serum-free, stroma-free conditions, using small molecules SR1 (Stem-Regenerin1) and UM171, adapting the protocol published by Fares et al.[11]. We cultured FL-HSPC in serum free expansion media (SFEM) (StemSpan2 supplemented with human low density lipoprotein, hSCF, hFLT3-1 and hTpo, SR1 and UM171 see Methods) and observed a comparable MLLT3-induced expansion of FL HSPC (Figure S3 E-G). Given the potential for clinical use of these finding we also tested whether cord blood (CB) HSPC would be equally responsive to MLLT3-mediated in vitro expansion. CB-HSPC also showed a net increase in phenotypic HSPC when cultured with MLLT3-OE on OP9M2 (Figure S3 H-J) and in SFEM (FIG. 21K-M) compared to control infected cells. These data demonstrate that MLLT3 can expand human HSPC from different sources (FL and CB) that are cultured using different established human HSPC culture conditions. Based on the potential clinical utility, we chose cord blood, and the SFEM culture conditions for, in vivo transplantation studies.

Figure 17:
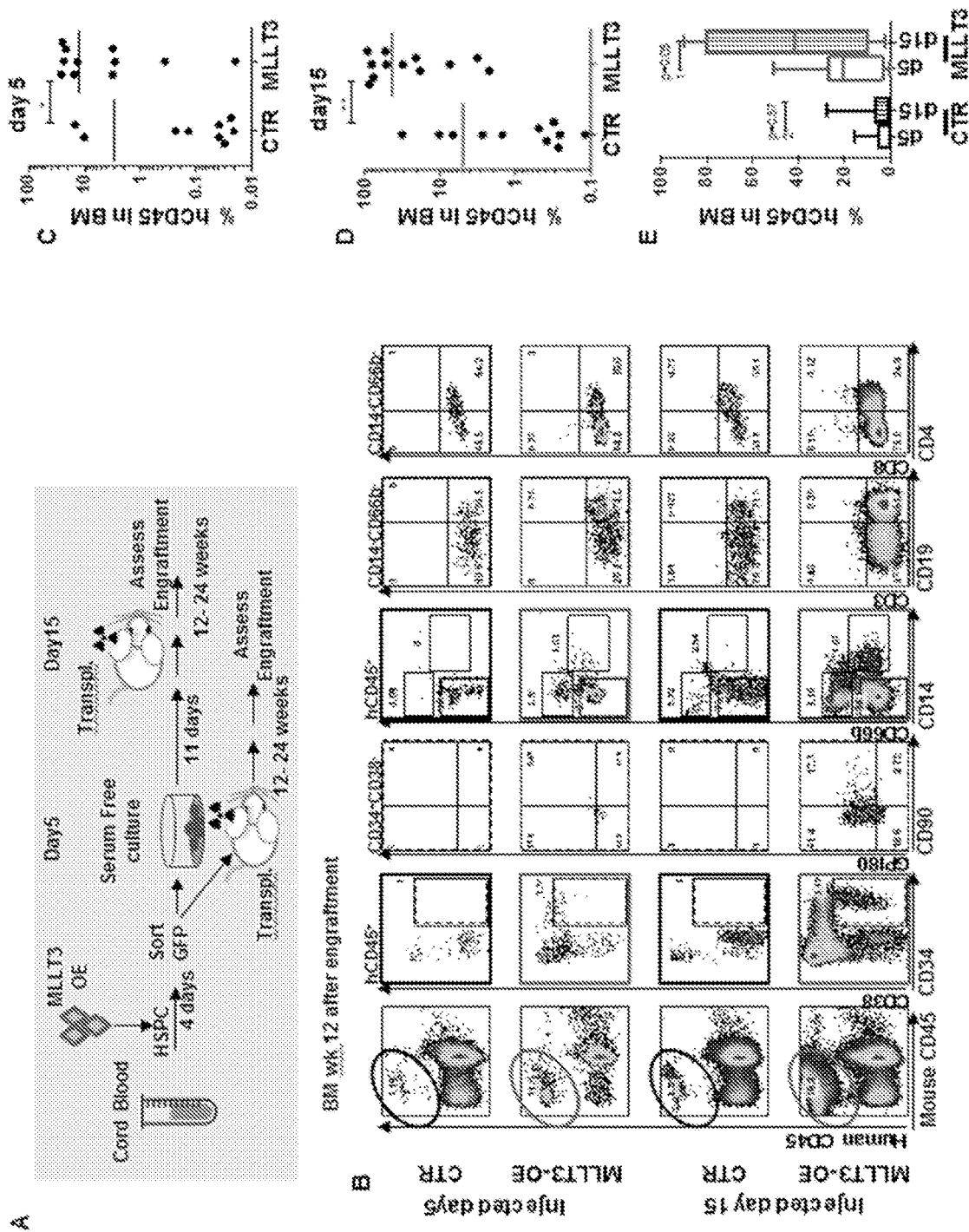
FIG. 17A-G. Overexpression of MLLT3 maintains and expands engraftment potential in CB-HSPC. (A) Schematic showing the transplantation strategy with MLLT3 overexpression CB-HSPC. CB-HSPC were pre-stimulated 24 hours in serum-free expansion culture (SFEM, StemSpan2 supplemented with hLDL, SCF, FLT3-1, Tpo, UM171 and SR1, see methods), then infected on day 1 and 2 with FUGW empty vector (CTR) or FUGW-MLLT3 (MLLT3-OE). On day 5, GFP+ cells were sorted and 5000 cells per mouse were either injected in sublethally irradiated NSG mice or further expanded in SFEM2 for 10 days. At day 15 the total progeny of the 500 cells sorted at day 5 was injected in sublethally irradiated NSG mice. (F) Representative FACS plots from mouse BM aspirations 12 weeks post-transplantation assessing human CD45+ cells and multi-lineage engraftment (CD66 and CD33 for myeloid, CD19 for B-lymphoid and CD3 CD4 and CD8 for T-lymphoid). (G) Quantification of human engraftment (n=9-12 mice per condition from 3 independent experiments Individual values and mean are shown.) Statistical significance was assessed using Student's t-test (*p<0.05, **p<0.01). (E) Percent human engraftment is compared across time-points (day 5 and day 15) within treatment groups to show a MLLT3-specific expansion of engraftment potential over time in culture.
Figure 22:
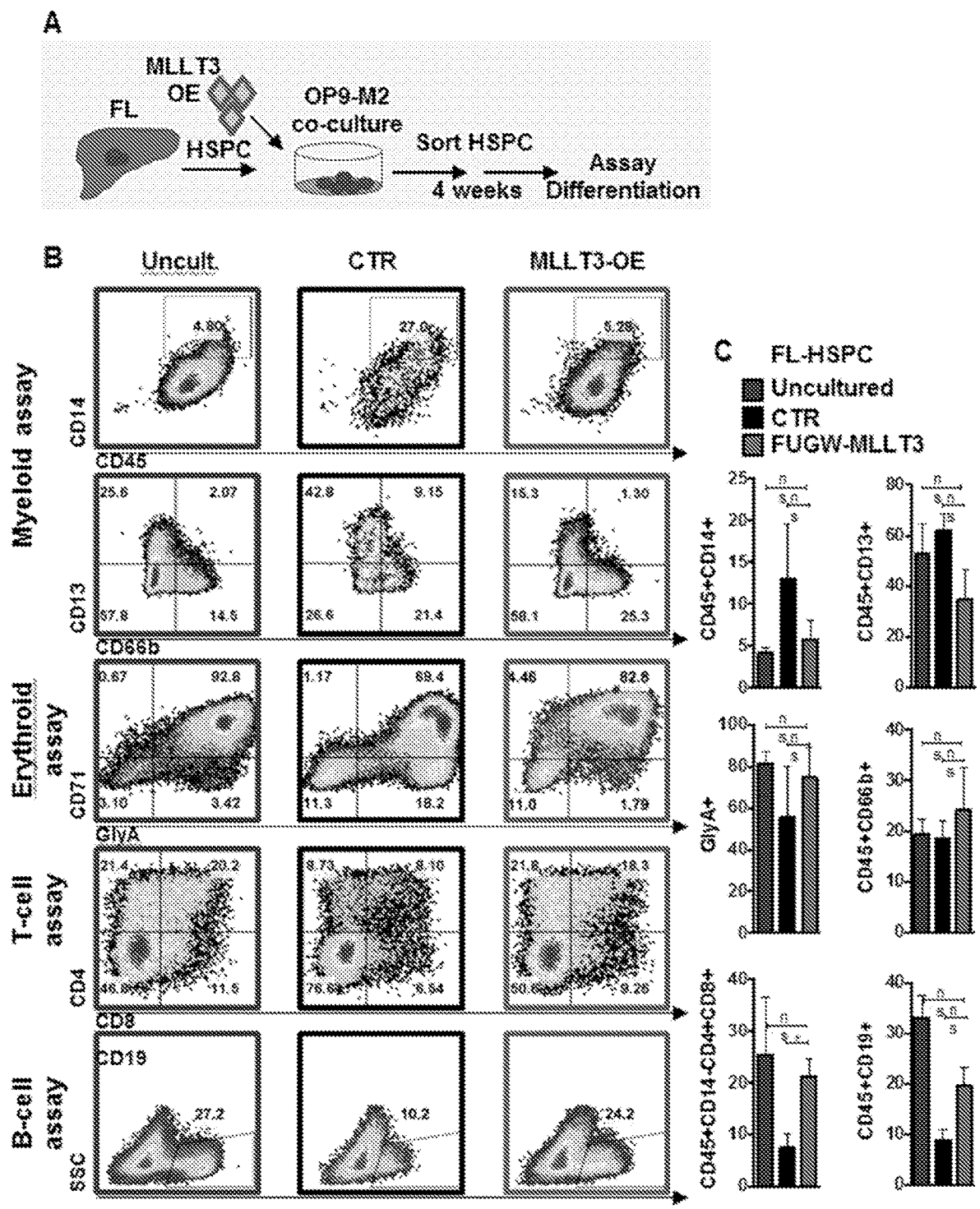
FIG. 22A-C. Overexpression of MLLT3 sustains HSPC ability to differentiate into all hematopoietic lineages. (A) Schematic showing the strategy for MLLT3-OE in FL-derived HSPC. HSPC infected with CTR or MLLT3-OE vectors were expanded 4 weeks on OP9M2 stroma, then sorted GFP+HSPC were assessed for in vitro differentiation (see Methods). Differentiation of 4 week expanded HSPC populations were compared to the differentiation potential of uncultured HSPC in parallel assays. Results show that the expansion in presence of MLLT3 does not alter the ability of the HSPC to differentiate into four major lineages shown by FACS analysis (B), and quantification of the percentage of the indicated populations in each assay (C). Mean and SEM values; statistical significance was assessed using the Student's t-test.
Figure 23:
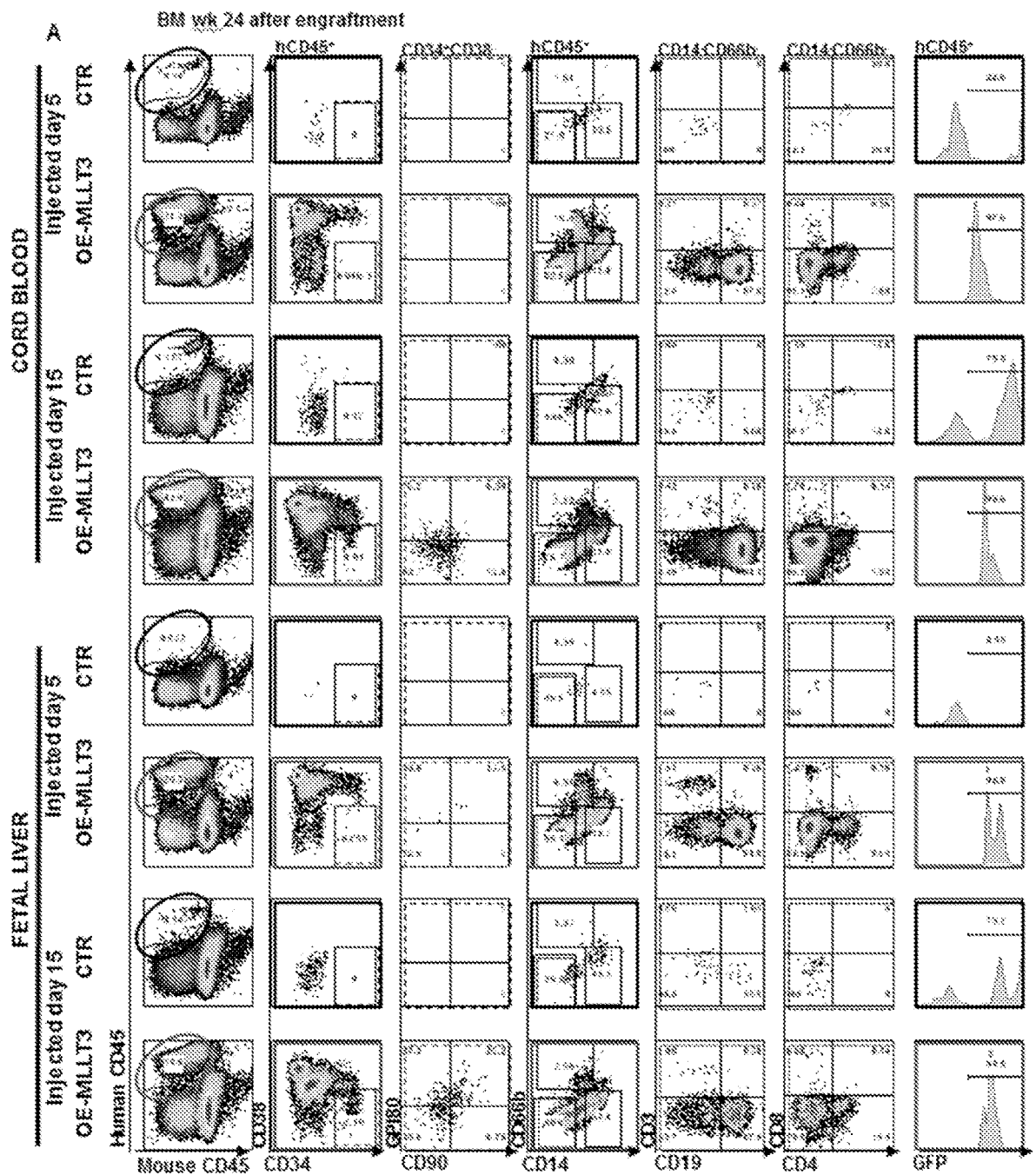
FIG. 23A-E. Overexpression of MLLT3 sustains long-term engraftment ability in CB and FL-HSPCs. (A) NSG mice engrafted with 5000 GFP+HSPC or their progeny (see FIG. 17 and methods) were sacrificed after 24 weeks and tested for human engraftment and differentiation potential by FACS analysis of the bone marrow. Quantification of human engraftment (from 2 independent experiments) from cord blood HSPC injected at day 5 (B) and day 15 (C) as well as fetal liver HSPC injected at day 5 (D) and day 15 (E). Individual values from each engrafted mouse and mean are shown. Statistical significance was assessed using Student's t-test (*p<0.05). (E) percent human engraftment is compared across time-points (day 5 and day 15) within treatment groups to show a MLLT3-specific expansion of engraftment potential over time in culture.
Figure 23:
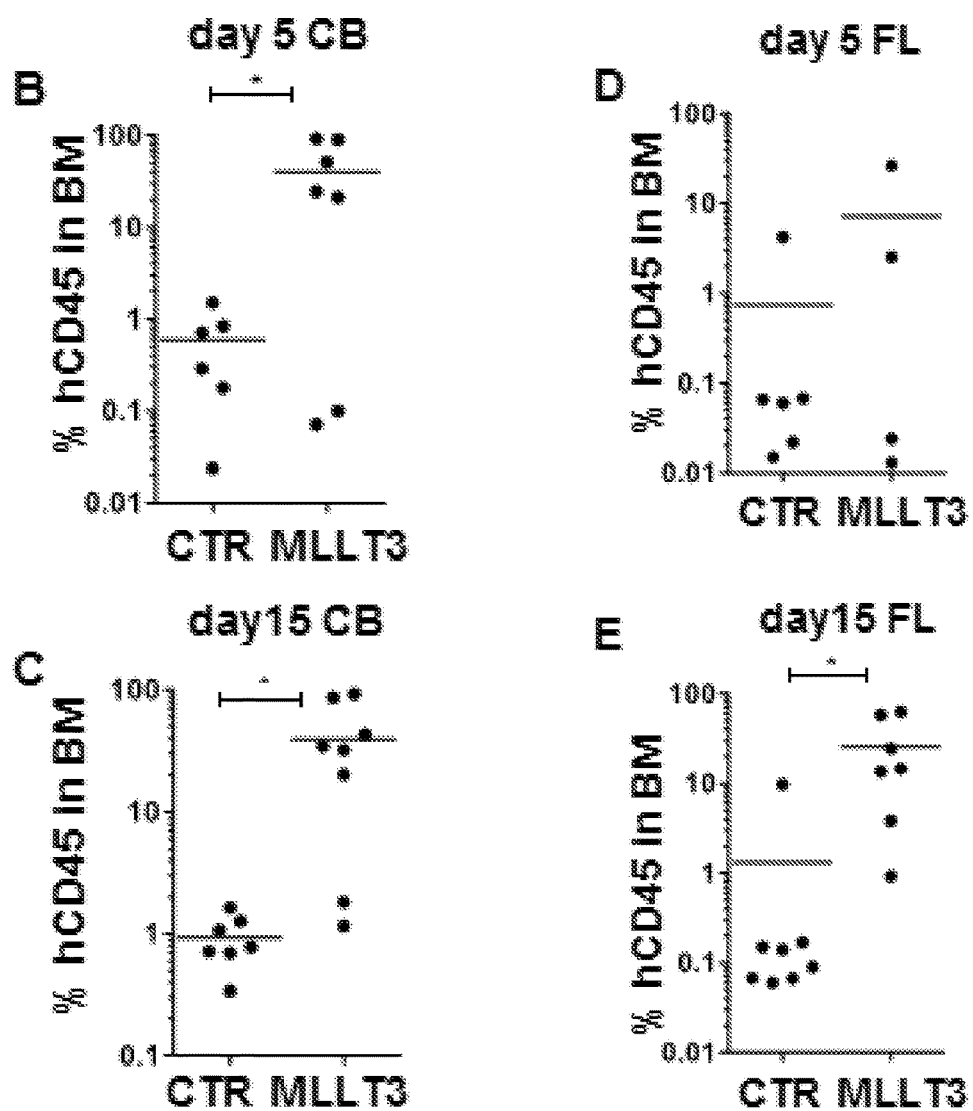

We tested the ability of MLLT3 to maintain or expand transplantable human HSCs during culture expansion (FIG. 17A). GFP+ cells were sorted early after transduction of CB-HSPC with the MLLT3-OE or control vector (day 5) and transplanted in a limiting number (5000) in sublethally irradiated NSG mice. The same number of cells was also expanded in SFEM in presence of SR1 and UM171 for further 10 days (day 15), and transplanted another set of NSG mice with the expanded progeny of 5000 GFP cells. MLLT3-OE transduced cells showed a more robust human HSC engraftment in mouse BM compared to GFP control in both day 5 and day 15 culture transplantations, as assessed at 12 weeks by bone marrow aspiration (FIG. 17B-D) and at 24 weeks by bone marrow, peripheral blood and spleen cellular composition analysis (FIG. 23A). The engrafted MLLT3-expressing human cells harbored a robust population of HSPC (CD34+CD38−), and also displayed differentiation to all major blood lineages including myeloid (CD14+ or CD66b+) and lymphoid (CD19+ B-cells and CD4+ and/or CD8+ T-cells) (FIG. 17, 23A-C). This is further evidence that MLLT3 enforced expression in cultured HSPC preserves their multipotency and ability to differentiate, in accordance with the in vitro results in FIG. 22. Similar results were obtained with transplanting MLLT3 overexpressing FL-HSPC (FIGS. 23A, D and E). Furthermore, comparison of the engraftment levels of human cells among the two culture time-points chosen for engraftment (day 5 and day 15) showed that MLLT3 overexpressing cells expanded the engraftable units during culture, whilst the control-vector transduced HSPC were unable to engraft robustly after the culture expansion (FIG. 17E). No mice in this study developed signs of leukemia, lymphoma or other neoplasias within the 24 weeks of transplantation, further excluding any cell-transformation effect of the MLLT3 at the levels achieved in our overexpression. These results demonstrate that sustaining MLLT3 expression during culture helps maintain and expand multipotent, engraftable human HSCs.

Figure 18:
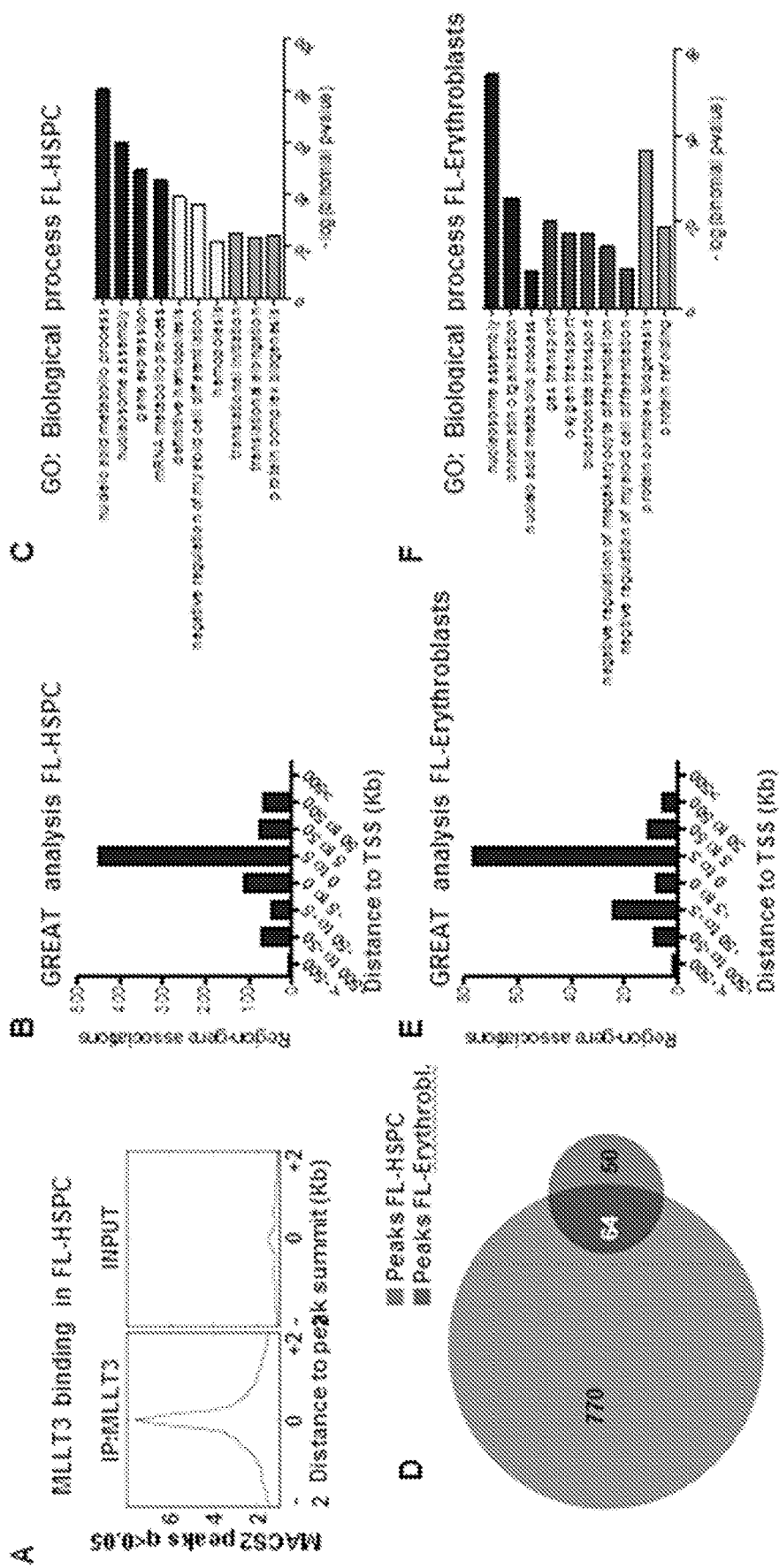
FIG. 18A-F. MLLT3 binds to genes at transcriptional start sites in a cell-specific manner. (A) MLLT3 ChIP-seq in HSPC reveals a discrete number of peaks of enrichment above the input signal (834 q<0.05). (B) GREAT analysis showing that the majority of the peaks reside between the transcriptional start site (TSS) and the first 5 kilobases of a gene, indicating a possible role in direct transcriptional control of the binding targets. (C) GO-analysis of the MLLT3 associated genes reveals strong enrichment for specific biological process categories. (D) Comparison of peak calling and binding regions of MLLT3 in FL-erythroblasts (CD34−GlyA+CD71+) from fetal livers from the same sources where HSPC were extracted. A smaller number of peaks are detected, showing partial overlap in peak regions. (E) GREAT analysis shows similar TSS proximity for those peaks, and (F) GO-analysis of the MLLT3 associated genes in FL-erythroblasts reveals common and cell type specific biological process categories when compared with the peaks detected in FL-HSPC.

To define the molecular mechanism underlying the ability of MLLT3 to sustain the HSC function, the genomic localization of MLLT3 binding on FL-HSPC DNA was analyzed using chromatin immunoprecipitation and high throughput sequencing (ChIP-seq). We observed statistically significant binding of MLLT3 in FL-HSPC at several genomic sites (825, q<0.05; 1659, p<0.01) (FIG. 18A). The majority of the binding occurred around transcriptional start sites (TSS) and within the first 5 kb downstream of TSS, consistent with the expected loading of MLLT3 at transcribed genes and its reporter function with the superelongation complex in other cell types (FIG. 18B). GO analysis of the genes found within 5 kb from an MLLT3 peak shows high enrichment for specific biological processes: genes involved in transcriptional regulation and chromatin organization functions (e.g. binding to histone genes HIST2H2BE, HIS T1H3D, HIST1H4E); general transcription factors (e.g. FOS, JUND, NFKBIA); definitive hematopoiesis and regulation of hematopoiesis (e.g. MEIS1, BCL11A, RUNX1, MYB, LMO2, GATA2, ETV6); regulation of translation (e.g. EEF1A1, EIF4A1, EIF5A) and ribosomal proteins (e.g. RPL18A, RPL10). This analysis shows that MLLT3 binds to highly expressed genes including both genes involved in basic cellular functions (e. g. chromatin organization, transcription, translation) as well as specific HSC regulators. We compared this binding pattern to MLLT3 binding in CD34−GlyA+CD71+ human fetal liver erythroblasts, as erythroid progenitors have also been shown to independently express MLLT3[12]. ChIPseq analysis of FL erythroblasts showed fewer MLLT3 peaks (114, q<0.05), which partially overlap with the FL-HSPC peaks (62, 54.4%). GREAT analysis showed a similar distribution of the MLLT3 erythroid cell peaks around the TSS. The GO categories representing MLLT3 erythroid bindings sites overlap partially with the FL-HSPC binding analysis (e.g. chromatin organization, gene expression and translation) and are in part unique to functions related to red blood cell development (e.g. oxygen transport). This analysis implied that MLLT3 can both regulate key cellular function that are shared with many cell types, and as well as cell type specific functions. The high level of MLLT3 expression in human HSCs that correlates with binding to key HSC regulators suggests that MLLT3 promotes HSC self-renewal by governing proper expression of the hematopoietic stem cell transcriptional network.

Figure 19:
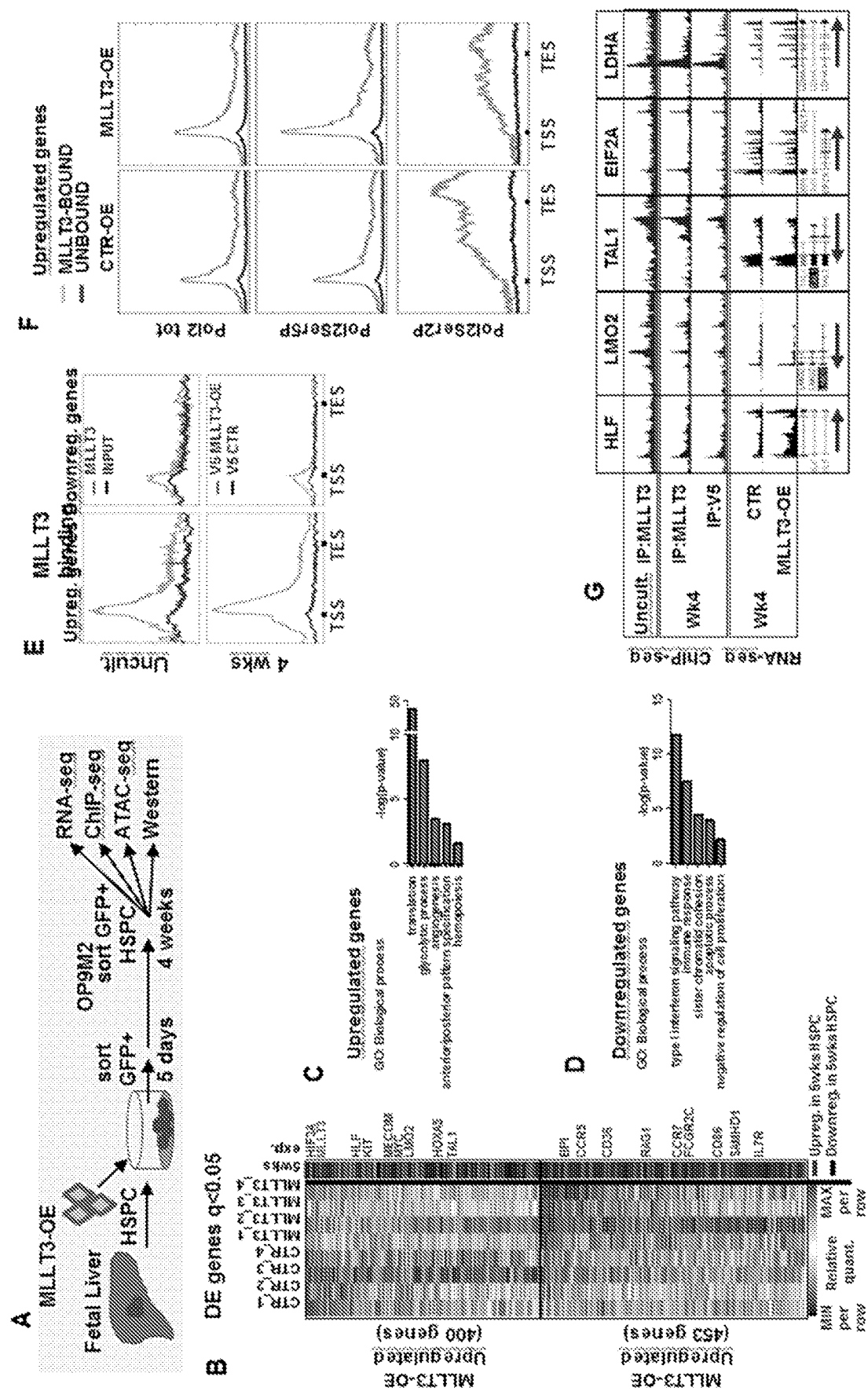
FIG. 19A-G. MLLT3 overexpression sustains the expression of HSC gene network by modulating RNA-pol2 state. (A) Schematic showing the strategy for MLLT3-overexpressing FL-HSPC expansion for molecular studies. CB-HSPC were pre-stimulated 24 hours in serum-free expansion culture (see methods), then infected with FUGW empty vector (CTR) or FUGW-MLLT3 (MLLT3-OE). On day 5, GFP+ cells were sorted, reseeded on OP9M2 stroma and cultured for additional 24 days. (B) Heatmap showing differentially expressed genes (p<0.05 from 4 independent experiments) from total RNA-seq of sorted GFP+HSPC after expansion with MLLT3-OE or CTR vectors. Each line represents one gene for which the relative RPKM is quantified as indicated in the scale below the plot. On the far right column a summarized quantification of the upregulation (red) or downregulation (blue) of the same genes in the comparison between uncultured, and 5 weeks expanded FL HSPC on OP9, derived from Magnusson et al. is represented. On the right some important HSC regulators are highlighted within the MLLT3 upregulated section, and some immune and inflammation mediated genes, aberrantly upregulated in culture, are listed in the downregulated section. (D) GO analysis of genes upregulated upon MLLT3 overexpression reveals enrichment for processes overlapping with the GO-categories of MLLT3 bound genes in uncultured cells (transcription, hemopoiesis). (E) GO analysis of genes downregulated upon MLLT3 overexpression reveals enrichment for processes aberrantly induced during HSPC culture (immune response, apoptosis). (E) Distribution of MLLT3 in up vs downregulated genes shows significantly more enrichment for MLLT3 binding to the MLLT3 upregulated gene group, as assessed by binding of endogenous MLLT3 in uncultured HSPC (top panels) and by V5 tag ChIP in the 4 week expanded HSPC overexpressing MLLT3 (bottom panels). (F) ChIP-seq analysis of the total RNA-polymerase 2 (Pol2 tot) and its C-terminal domain phosphorylated forms (Ser5P=Ser5 phosphorylated, and Ser2P=Ser2 phosphorylated) within the genes upregulated by MLLT3 that show direct binding (green) or no binding (black). Results show a relative increase of the RNApol2 loaded at the promoter, (Pol2Ser5P), indicating a higher loading and occupancy of engaged RNApol2 at these promoters. (G) Screenshots of the UCSC genome browser data showing example genes directly bound and upregulated by MLLT3 in this analysis.

To test the hypothesis that MLLT3 sustain HSC self-renewal by governing HSC specific gene expression programs, we assessed gene expression levels in cultured HSPC after modulating MLLT3 levels. Given that the HSPC population becomes rapidly depleted after complete MLLT3 loss (FIG. 15), it was not feasible to study HSPC successfully knocked-down for MLLT3. Leveraging on the knowledge that MLLT3 expression is diminished upon HSPC culture[4], we performed total RNAseq in HSPC expanded for 4 weeks in presence or absence of MLLT3 overexpression. Even a modest lentiviral overexpression of MLLT3 (2.35 fold at transcript level) in cultured HSPC resulted in differential expression of a group of 853 genes (400 upregulated, 453 downregulated) (FIG. 19A). Gene ontology analysis showed that genes involved in global cellular regulation (e.g. translation, glycolysis) as well as several known HSPC regulators (MEIS1, RORA, c-MYC, LMO2, TAL1, GFI1, HHEX, HOXA3, 4, 5, 6, 11) and HSC surface receptors (c-KIT, CXCR4, ROBO4, EPHA1, PROM1, CD34) were induced by MLLT3 overexpression while other programs (immune response, inflammatory response, apoptosis) were downregulated (FIG. 19B). Comparison to previous microarray analysis of programs that were dysregulated during 5 weeks of human HSPC culture on OP9M2 showed that sustaining MLLT3 expression in culture can rescue at least part of the culture-associated defect in HSPC gene expression[4] (FIG. 19A, right column). Moreover, some of the genes whose expression in culture was sustained by MLLT3 were identified in our initial analysis (FIG. 14) of genes that associate with self-renewing HSCs in all comparisons (e.g. HIF3A, HLF, MECOM). This result shows that maintaining MLLT3 expression in cultured cells can help sustain HSC self-renewal network and at least partially prevent the aberrant gene expression in HSPC associated with prolonged culture.

To identify the differentially regulated genes that are directly regulated by MLLT3, gene expression data was intersected with MLLT3 binding data in cultured cells. MLLT3 binding was observed in a subset of the genes that were upregulated by MLLT3 in culture, while minimal binding was observed in downregulated genes, implying that MLLT3 is primarily a positive regulator of transcription in human HSCs (FIG. 19E).

MLLT3 has been described in human cell lines as a component of the SEC[7], a machinery responsible for regulating RNA polymerase 2 elongation at active genes. SEC recruits pTEF-b[13] and the PAF1C machinery that are necessary for efficient elongation[14] and coupling of transcription with mRNA processing[15]. SEC is known to regulate many highly expressed and rapidly induced genes that require coordinated expression based on environmental stimuli (e.g. early response genes[16, 17]), and it has recently been unveiled that its component PAF1 positively regulates polymerase pausing[18], a process that in many instances has been associated with positive regulation of gene expression[19]. We thus asked if MLLT3 could modulate the RNApol2 activity at genes that it binds to.

To examine if MLLT3 overexpression regulated Pol2 function, ChIP-seq was performed for total Pol2 and the two major modifications of the RNApol2 C-terminal domain: Pol2-Ser5P, associated with an engaged Pol2 state at the promoter, and Pol2-Ser2P, associated with an elongating polymerase after pausing-release by pTEF-b. The binding profiles of these modifications reveal that although MLLT3 did not affect total Pol2 binding, MLLT3 overexpression specifically induces the maintenance of paused polymerase by increasing the amount of Pol2-Ser5P at the promoter of the target genes (FIG. 19F). These results show that the increase in Ser5-phosphorylated RNA-pol2 is particularly pronounced at the direct target genes of MLLT3, nominating MLLT3 as a modulator of engaged polymerase.

The presence of engaged RNApol2 paused at the promoter has been described as a key determinant of gene regulation[19]. It has been demonstrated that disrupting RNApol2 pausing through knockdown of the negative elongation factor NELF, the major determinant of the polymerase arrest in the promoter, leads to gene silencing rather at a large subset of targets in Drosophila[20], resulting in overall RNApol2 reduction at promoters and chromatin closure[21]. Similarly PAF1 knockdown in mouse ES cells leads to an increase in RNApol2-Ser2P in the gene bodies[18]. Finally Pol2 pausing has been linked to the specification of definitive hematopoietic cells in zebrafish whereby disruption of spn5 (a DSIF subunit) obliterates definitive blood formation[22]. The present work suggests that the SEC component MLLT3 facilitates the pausing of RNApol2 at a subset of HSC genes, including factors regulating chromatin structure, transcription and translation, which is essential for maintaining human HSC self-renewal. Moreover, this work implies that MLLT3 mediated pausing of RNApol2 must be sustained over time in culture for successful expansion of functional human HSC. It will be of great interest to establish what external signals that are missing in culture, maintain proper MLLT3 levels during adult HSC homeostasis.

Example 6

Materials and Methods for Example 5

Human Hematopoietic Tissue Collection

Second trimesters fetal livers were de-identified, discarded material obtained from elective termination of pregnancies following informed consent. As these tissues are discarded material with no personal identifiers, this research does not constitute research on Human Subjects. This protocol was reviewed by the UCLA IRB committee, who determined that such studies can be performed without further IRB review. Specimen age for this study is denoted as developmental age, two weeks less than gestational age, and was determined by ultrasound or estimated by the date of the last menstrual period. Tissues were harvested into PBS 5% FBS (Hyclone), Ciprofloxacin HCl (10 ng/mL, Sigma), amphotericin B (2.50 µg/mL, Invitrogen), 1% penicillin/streptomycin, transported on ice and processed the same day.

Human Hematopoietic Tissue Processing

Single cell suspensions were prepared from FL at 14-17 weeks of developmental age or cord blood collected at term. FL tissues were mechanically dissociated using scalpels and syringes. From single cell suspension of FL and CB, mononuclear cells were enriched on a Ficoll layer according to manufacturer's protocol (GE Healthcare Biosciences AB) and strained through a 70 µm mesh. Single cell suspensions obtained from human fetal livers or human cord blood units were magnetically isolated with anti-CD34 microbeads (Miltenyi Biotech) according to manufacturer's protocol.

OP9M2 Stromal Co-Culture for HSPC Expansion

OP9M2 cells were irradiated (20 Gy) and pre-plated (50,000 cells/cm$^2$) onto tissue culture-treated wells 24 hours before start of co-culture in OP9-medium (α-MEM (Invitrogen), 20% FBS (Hyclone), P/S/G). Hematopoietic cells derived from hematopoietic tissues were plated on stromal layer in OP9-medium supplemented with SCF (25 ng/ml, Peprotech), Flt-3 (25 ng/ml, Peprotech) and TPO (25 ng/ml, Peprotech) (HSC-medium). Cells were co-cultured at 37° C. and 5% $CO_2$ and re-plated or analyzed/sorted by flow cytometry every 7-14 days. Half of the HSC-medium was replaced every other day.

Serum Free Expansion Medium Culture for HSPC Expansion

HSPC were plated in Stem Span SFEM II (SCT) supplemented with human SCF (100 ng/ml, Peprotech), human FLT3-1 (100 ng/ml, Peprotech), human TPO (50 ng/ml, Peprotech), human low-density lipoprotein (hLDL, 10 µg/ml, SCT) P/S/G). For expansions aimed for mouse engraftment 500 nM StemRegenerin1 and 35 nM UM171 were added to the medium for the time of culture. Cells were cultured at 37° C. and 5% $CO_2$ and re-plated or analyzed/sorted by flow cytometry every 7-14 days. Half of the HSC-medium was replaced every other day.

Flow Cytometry and Cell Sorting

FACS analysis was performed using single cell suspensions prepared as described. Cells were stained with mouse anti-human monoclonal antibodies against human-CD45-PE cl.J.33 (IM2078U; Beckman coulter) -APC, -APC-H7 cl.2D1 (368512, 368516; Biolegend), -BV711 cl.HI30 (304050; Biolegend), mouse-CD45-APC-H7 cl. 30-F11 (557659; BD) (all diluted 1:100), CD34-APC cl. 581 (555824; BD, 1:20), CD90-FITC cl. 5E10 (555595; BD, 1:100), CD38-PE-Cy7 cl. HIT2 (560677; BD, 1:100), CD19-PE cl. 1D3 or HIB19 (12-0193, 12-0199; eBiosciences, 1:50), GPI-80-PE cl. 3H9 (D087-5; MBL International Corporation, used at 1:50), CD3-PE-Cy7 cl. SK7 (557851, BD) (eBiosciences, 1:50), CD4 APC (MHCD0405; Invitrogen, 1:50), CD8-PE cl. HIT8A (555635; BD, 1:50), CD13-APC cl. WM15 (557454; BD, 1:500), and CD66b FITC cl. G10F5 (555724; BD, 1:50) CD33-PE cl. WM53 (561816; BD, 1:100).

Dead cells were excluded with 7-amino-actinomycin D (7AAD) (BD Biosciences, used at 1:50). Cells were assayed on a BD-LSRII flow cytometer and data were analyzed with FlowJo software (Tree Star Inc.). Cell sorting was performed using a BD FACS Aria II.

Hematopoietic Differentiation Assays

For Myeloid assay, FL-derived HSPC or sorted HSPC expanded on OP9 were plated in StemSpan2 SFEM II (SCT) supplemented with GCSF (20 ng/ml, Peprotech), GMCSF (20 ng/ml, Peprotech), TPO (25 ng/ml, Peprotech), SCF (25 ng/ml, Peprotech), L-Glutamine (Thermo Fisher Scientific), and Antibiotic-Antimycotic (Thermo Fisher Scientific). For the Erythroid assay, HSPC were plated in Stem Span SFEM II supplemented with IL3 (20 ng/ml, Peprotech), EPO (2.5 IU, Thermo Fisher Scientific), SCF (25 ng/ml, Peprotech), L-Glutamine (Thermo Fisher Scientific), and Antibiotic-Antimycotic (Thermo Fisher Scientific). For T cell assay, HSPC were plated on non-irradiated OP9-DL1 stroma (25,000 cells/cm$^2$) in OP9-medium supplemented with SCF (25 ng/ml, Peprotech), FLT3-L (10 ng/ml, Peprotech) and IL-7 (20 ng/ml, Peprotech). For B cell assay, HSPC were seeded on irradiated (20Gy) OP9M2 (25,000 cells/cm$^2$) in MEM-alpha 5% FBS supplemented with SCF (25 ng/ml, Peprotech), FLT3-L (10 ng/ml, Peprotech) and IL-7 (20 ng/ml, Peprotech). In each assay, cells were cultured in 24 well plates with 1 ml of media. Half media changes were applied every 2-3 days. Cells were analyzed by flow cytometry after 2 weeks.

RNA Isolation, cDNA Synthesis and Quantitative Reverse Transcriptase PCR

RNA isolation was performed using the RNeasy Mini kit (Qiagen) with additional DNase (Qiagen) step using manufacturer's protocol. cDNAs were prepared using Quantitech reverse transcription kit (Qiagen), and quantitative polymerase chain reaction (qPCR) for GAPDH, and MLLT3 was performed with the LightCycler 480 SYBR Green I Master Mix (Roche) on the Lightcycler 480 (Roche).

RNA-Sequencing Analysis

Total RNA from 50000 sorted cells was extracted using the RNeasy Mini kit (Qiagen) and library was constructed using KAPA RNA HyperPrep Kit with RiboErase (HMR). Libraries were sequenced using HIseq-4000 (Illumina) to obtain paired end 50 bp long reads. Demultiplexing of the reads based on the barcoding was performed using in house Unix shell script. Mapping to the human genome (hg19) was performed using TopHat v2.0.9 or v2.0.14[23] with the parameters—no-coverage-search -M -T -x 1. Coverage files were created with the Genomecov tool from Bedtools[24] with the parameters -bg -split -ibam. For abundance estimations (FPKMs) the aligned read files were further processed with HOMER coupled to edgeR on the hg19 annotation and heatmaps generated with Morpheus.

ChIP-Sequencing Analysis

Cells (50000 to 100000 per IP) were crosslinked in 1% formaldehyde for 10 minutes, quenched with glycine 0.025M and snap-frozen as a dry pellet. The pellet was resuspended in lysis buffer (50 mM Tris 8.2, 10 mM EDTA, 1% Triton X 100, 0.1% NaDeoxycholate, 0.5% Sarkosyl) and sonicated 12 min at a 5% intensity. Chromatin was incubated overnight with the selected antibody, preloaded onto ProteinG Dynabeads and washed twice with each of the solutions (low salt wash, high salt wash, LiCl wash and TE). Libraries were prepared with the Nugen Ovation Ultralow kit v2 following manufacturer instructions and sequenced using HIseq-4000 (Illumina) to obtain single end 50 bp long reads. Demultiplexing of the reads based on the barcoding was performed using in house Unix shell script. Mapping to the human genome (hg19) was performed using bowtie2. Samtools v1.3.1 package was uses to create a .bam file, remove duplicates, blacklisted region and ChrM regions, sort and index. Coverage files, average profiles and heatmaps were created with the deeptools packages.

Production of Lentiviral shRNA and Overexpression Vectors shRNA experiments were performed with pLKO lentiviral vectors from the TRC library containing puromycin resistance gene. Human MLLT3 was cloned from human FL full-length cDNA, into the constitutive pFUGW lentiviral vector, (Addgene plasmid #14883, from David Baltimore), downstream and in frame with the GFP sequence with the synthetic addition a P2A sequence between the 2 ORFs. For lentiviral vectors production, 20 million 293T cells were transfected with 12.5 ug deltaR8.2, 5 μg VSV-G, and 12.5 μg DNA/shRNA and 90 μL of lipofectamine-2000 (Invitrogen) in OPTI-MEM and incubated for 5-6 hours at 37° C. After incubation for 48 hours in complete medium, supernatant was filtered and concentrated using an ultracentrifuge (Beckman Coulter) at 20,200 rpm for 1.5 hours at 4° C. Following centrifugation, pelleted viruses were resuspended in 125 μL of SFEM and stored at −80° C.

Lentiviral Transduction of CD34$^+$ Cells

FL and CB-HSPC sorted for the indicated phenotype were prestimulated 24 h in fresh SFEM2 culture medium supplemented with 100 ng/mL SCF, 100 ng/mL TPO and 100 ng/mL FLT3-L. Wells were treated with 40 μg/mL RetroNectin (Takara) and seeded with pre-stimulated FL-HSPC in 300 μL SFEM culture medium. Lentivirus was added in during 24 hours incubation. Transduced cells were washed and seeded on OP9M2 with HSC-medium. For shRNA-lentiviral vectors, puromycin (1.0 μg/ml) treatment was used for selection of transduced HSPC and maintained throughout culture.

Transplantation into NOD-Scid IL2Rγ-Null Mice

Female NOD-scid IL2Rγ-null (NSG, Jackson Laboratories) mice, 8-12 weeks old, were sublethally irradiated (325 rads) and intra-tibially injected with FL or hESC CD34+ cells in a volume of 35 μL. Mice were transplanted with either 5000 cells or their cultured progeny.

For Overexpression Experiments

For shRNA treated FL cells, 50,000 cells were infected with shRNA lentivirus and expanded on OP9M2 for 9 days under puromycin selection. Transduced hematopoietic cells were retro-orbitally injected in sublethally irradiated NSG mice.

Mice were bone marrow aspirated from one femur under general anesthesia induced with isoflurane/O2 vaporizer, and sacrificed at 24 weeks to harvest bone marrow blood and spleen. Collected cells were FACS-analyzed to evaluate human engraftment (human CD45 and mouse CD45), differentiation into myelo-lymphoid lineages (CD13, CD14, CD66, CD3 or CD19) and preservation of the HSPC compartment (CD34+, CD38-, CD90+, GPI80+). All studies and procedures involving mice were approved by the UCLA Animal Research Committee (Protocol 2005-109).

Statistics and Reproducibility

Graphs were generated and statistical significance was calculated with GraphPad PRISM software. R version.3.2.3. Statistical significance was assessed using the Student's paired t-test for paired data sets or unpaired for the rest. The null hypothesis of the medians/means being equal was rejected at $\alpha=0.05$ and significant p-values are shown in each graph.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

1. Swiers, G., Rode, C., Azzoni, E. & de Bruijn, M. F. T. R. A short history of hemogenic endothelium. *Blood cells, molecules& diseases* 51, 206-212 (2013).
2. Gritz, E. & Hirschi, K. K. Specification and function of hemogenic endothelium during embryogenesis. *Cell Mol Life Sci* (2016).
3. Prashad, S. L. et al. GPI-80 Defines Self-Renewal Ability in Hematopoietic Stem Cells during Human Development. *Cell Stem Cell* (2014).
4. Magnusson, M. et al. Expansion on stromal cells preserves the undifferentiated state of human hematopoietic stem cells despite compromised reconstitution ability. *PloS one* 8, e53912 (2013).
5. Dou, D. R. et al. Medial HOXA genes demarcate haematopoietic stem cell fate during human development. *Nat Cell Biol* 18, 595-606 (2016).
6. He, N. et al. Human Polymerase-Associated Factor complex (PAFc) connects the Super Elongation Complex (SEC) to RNA polymerase II on chromatin. *Proceedings of the National Academy of Sciences of the United States of America* 108, E636-645 (2011).
7. Lin, C. et al. AFF4, a component of the ELL/P-TEFb elongation complex and a shared subunit of MLL chimeras, can link transcription elongation to leukemia. *Mol Cell* 37, 429-437 (2010).
8. Mohan, M. et al. Linking H3K79 trimethylation to Wnt signaling through a novel Dot1-containing complex (DotCom). *Genes Dev* 24, 574-589 (2010).
9. Li, Y. et al. AF9 YEATS domain links histone acetylation to DOT1L-mediated H3K79 methylation. *Cell* 159, 558-571 (2014).
10. Bitoun, E., Oliver, P. L. & Davies, K. E. The mixed-lineage leukemia fusion partner AF4 stimulates RNA polymerase II transcriptional elongation and mediates coordinated chromatin remodeling. *Hum Mol Genet* 16, 92-106 (2007).
11. Fares, I. et al. Cord blood expansion. Pyrimidoindole derivatives are agonists of human hematopoietic stem cell self-renewal. *Science* 345, 1509-1512 (2014).
12. Pina, C., May, G., Soneji, S., Hong, D. & Enver, T. MLLT3 regulates early human erythroid and megakaryocytic cell fate. *Cell stem cell* 2, 264-273 (2008).
13. Peterlin, B. M. & Price, D. H. Controlling the elongation phase of transcription with P-TEFb. *Mol Cell* 23, 297-305 (2006).
14. Kim, J., Guermah, M. & Roeder, R. G. The human PAF1 complex acts in chromatin transcription elongation both independently and cooperatively with SII/TFIIS. *Cell* 140, 491-503 (2010).
15. Nagaike, T. et al. Transcriptional activators enhance polyadenylation of mRNA precursors. *Mol Cell* 41, 409-418 (2011).
16. Luo, Z., Lin, C. & Shilatifard, A. The super elongation complex (SEC) family in transcriptional control. *Nat Rev Mol Cell Biol* 13, 543-547 (2012).
17. Lin, C. et al. Dynamic transcriptional events in embryonic stem cells mediated by the super elongation complex (SEC). *Genes & Development* 25, 1486-1498 (2011).
18. Chen, F. X. et al. PAF1, a Molecular Regulator of Promoter-Proximal Pausing by RNA Polymerase II. *Cell* 162, 1003-1015 (2015).
19. Adelman, K. & Lis, J. T. Promoter-proximal pausing of RNA polymerase II: emerging roles in metazoans. *Nat Rev Genet* 13, 720-731 (2012).
20. Gilchrist, D. A. et al. NELF-mediated stalling of Pol II can enhance gene expression by blocking promoter-proximal nucleosome assembly. *Genes Dev* 22, 1921-1933 (2008).
21. Core, L. J. et al. Defining the status of RNA polymerase at promoters. *Cell reports* 2, 1025-1035 (2012).
22. Yang, Q. et al. RNA polymerase II pausing modulates hematopoietic stem cell emergence in zebrafish. *Blood* 128, 1701-1710 (2016).
23. Trapnell, C., Pachter, L. & Salzberg, S. L. TopHat: discovering splice junctions with RNA-Seq. *Bioinformatics* 25, 1105-1111 (2009).
24. Quinlan, A. R. & Hall, I. M. BEDTools: a flexible suite of utilities for comparing genomic features. *Bioinformatics* 26, 841-842 (2010).
25. Casero, D. et al. Long non-coding RNA profiling of human lymphoid progenitor cells reveals transcriptional divergence of B cell and T cell lineages. *Nat Immunol* 16, 1282-1291 (2015).

What is claimed is:

1. A method for promoting human hematopoietic stem cell self-renewal in vitro and engraftment in vivo comprising:
   a) introducing MLLT3 into a hematopoietic stem cell to generate an MLLT3-introduced hematopoietic stem cell; and,
   b) maintaining the MLLT3-introduced hematopoietic stem cell in culture for at least one week.

2. The method of claim 1, wherein b) comprises co-culturing with mesenchymal stem cell stromal cells.

3. The method of claim 2, wherein the mesenchymal stem cell stromal cells are OP9-M2 cells.

4. The method of claim 1, wherein the MLLT3 integrates into the genome of the hematopoietic stem cell.

5. The method of claim 1, wherein the MLLT3 does not integrate into the hematopoietic stem cell.

6. The method of claim 1, wherein MLLT3 is introduced into the hematopoietic stem cell by infection with a viral vector.

7. The method of claim 1, wherein MLLT3 is introduced into the hematopoietic stem cell by transfection with a nucleic acid.

8. The method of claim 7, wherein the nucleic acid is an expression construct.

9. The method of claim 1, further comprising introducing the MLLT3-introduced hematopoietic stem cell into a subject.

10. The method of claim 9, wherein the hematopoietic stem cell was obtained from a subject prior to introducing MLLT3.

11. The method of claim 1, further comprising generating the hematopoietic stem cell prior to step a) from an induced pluripotent stem cell.

12. The method of claim 1, further comprising generating the hematopoietic stem cell prior to step a) from an embryonic stem cell.

13. The method of claim 1, wherein, in b), the MLLT3-introduced hematopoietic stem cell undergoes cell division without differentiation.

14. The method of claim 1, wherein the MLLT3-introduced hematopoietic stem cell is CD34 positive and CD38 negative.

15. The method of claim 14, wherein the MLLT3-introduced hematopoietic stem cell is CD90 positive.

16. The method of claim 9, wherein the MLLT3-introduced hematopoietic stem cell engrafts into the subject's bone marrow.

17. The method of claim 1, wherein b) comprises maintaining the MLLT3-introduced hematopoietic stem cell in culture for at least four weeks.

18. The method of claim 1, wherein the hematopoietic stem cell is a human hematopoietic stem cell.

19. The method of claim 1, wherein the hematopoietic stem cell is a cord blood hematopoietic stem cell.

20. A method for promoting human hematopoietic stem cell self-renewal in vitro and engraftment in vivo comprising:
   a) introducing MLLT3 into a hematopoietic stem cell to generate an MLLT3-introduced hematopoietic stem cell;
   b) maintaining the MLLT3-introduced hematopoietic stem cell in culture with mesenchymal stem cell stromal cells for at least one week, wherein the MLLT3-introduced hematopoietic stem cell undergoes cell division without differentiation.

* * * * *

SEQUENCE LISTING

<160> NUMBER OF SEQ ID NOS: 6

<210> SEQ ID NO 1
<211> LENGTH: 1707
<212> TYPE: DNA
<213> ORGANISM: Homo sapiens

<400> SEQUENCE: 1

| | | | | | | |
|---|---|---|---|---|---|---|
| atggctagct | cgtgtgccgt | gcaggtgaag | ctggagctgg | ggcaccgcgc | ccaggtgagg | 60 |
| aaaaaaccca | ccgtggaggg | cttcacccac | gactggatgg | tgttcgtacg | cggtccggag | 120 |
| cacagtaaca | tacagcactt | tgtggagaaa | gtcgtcttcc | acttgcacga | aagctttcct | 180 |
| aggccaaaaa | gagtgtgcaa | agatccacct | tacaaagtag | aagaatctgg | gtatgctggt | 240 |
| ttcattttgc | caattgaagt | ttattttaaa | aacaaggaag | aacctaggaa | agtccgcttt | 300 |
| gattatgact | tattcctgca | tcttgaaggc | catccaccag | tgaatcacct | ccgctgtgaa | 360 |
| aagctaactt | tcaacaaccc | cacagaggac | tttaggagaa | agttgctgaa | ggcaggaggg | 420 |
| gaccctaata | ggagtattca | taccagcagc | agcagcagca | gcagcagtag | cagcagcagc | 480 |
| agcagcagca | gcagcagcag | tagcagcagc | agcagcagca | gcagcagcag | cagtagcagc | 540 |
| agcagtagca | gcagcagcag | cagcagtagt | accagttttt | caaagcctca | caaattaatg | 600 |
| aaggagcaca | aggaaaaacc | ttctaaagac | tccagagaac | ataaaagtgc | cttcaaagaa | 660 |
| ccttccaggg | atcacaacaa | atcttccaaa | gaatcctcta | gaaacccaa | agaaaataaa | 720 |
| ccactgaaag | aagagaaaat | agttcctaag | atggccttca | aggaacctaa | acccatgtca | 780 |
| aaagagccaa | aaccagatag | taacttactc | accatcacca | gtggacaaga | taagaaggct | 840 |
| cctagtaaaa | ggccgcccat | ttcagattct | gaagaactct | cagccaaaaa | aaggaaaaag | 900 |
| agtagctcag | aggctttatt | taaaagtttt | tctagcgcac | caccactgat | actcacttgt | 960 |
| tctgctgaca | aaaacagat | aaaagataaa | tctcatgtca | agatgggaaa | ggtcaaaatt | 1020 |
| gaaagtgaga | catcagagaa | gaagaaatca | acgttaccgc | catttgatga | tattgtggat | 1080 |
| cccaatgatt | cagatgtgga | ggagaatata | tcctctaaat | ctgattctga | acaacccagt | 1140 |
| cctgccagct | ccagctccag | ctccagctcc | agcttcacac | catcccagac | caggcaacaa | 1200 |
| ggtcctttga | ggtctataat | gaaagatctg | cattctgatg | acaatgagga | ggaatcagat | 1260 |
| gaagtggagg | ataacgacaa | tgactctgaa | atggagaggc | ctgtaaatag | aggaggcagc | 1320 |
| cgaagtcgca | gagttagctt | aagtgatggc | agcgatagtg | aaagcagttc | tgcttcttca | 1380 |
| cccctacatc | acgaacctcc | accaccctta | ctaaaaacca | caacaacca | gattcttgaa | 1440 |
| gtgaaaagtc | caataaagca | aagcaaatca | gataagcaaa | taagaatgg | tgaatgtgac | 1500 |
| aaggcatacc | tagatgaact | ggtagagctt | cacagaaggt | taatgacatt | gagagaaaga | 1560 |
| cacattctgc | agcagatcgt | gaaccttata | gaagaaactg | gacactttca | tatcacaaac | 1620 |
| acaacatttg | attttgatct | ttgctcgctg | gacaaaacca | cagtccgtaa | actacagagt | 1680 |
| tacctggaaa | catctggaac | atcctga | | | | 1707 |

<210> SEQ ID NO 2
<211> LENGTH: 1698
<212> TYPE: DNA
<213> ORGANISM: Homo sapiens

<400> SEQUENCE: 2

| | | | | | | |
|---|---|---|---|---|---|---|
| atgtgtgccg | tgcaggtgaa | gctggagctg | gggcaccgcg | cccaggtgag | gaaaaaaccc | 60 |
| accgtggagg | gcttcaccca | cgactggatg | gtgttcgtac | gcggtccgga | gcacagtaac | 120 |

```
atacagcact tgtggagaaa agtcgtcttc cacttgcacg aaagctttcc taggccaaaa    180
agagtgtgca aagatccacc ttacaaagta gaagaatctg ggtatgctgg tttcattttg    240
ccaattgaag tttattttaa aaacaaggaa gaacctagga agtccgcctt tgattatgac    300
ttattcctgc atcttgaagg ccatccacca gtgaatcacc tccgctgtga aaagctaact    360
ttcaacaacc ccacagagga ctttaggaga agttgctga aggcaggagg ggaccctaat     420
aggagtattc ataccagcag cagcagcagc agcagcagta gcagcagcag cagcagcagc    480
agcagcagca gtagcagcag cagcagcagc agcagcagca gcagtagcag cagcagtagc    540
agcagcagca gcagcagtag taccagtttt tcaaagcctc acaaattaat gaaggagcac    600
aaggaaaaac cttctaaaga ctccagagaa cataaaagtg ccttcaaaga accttccagg    660
gatcacaaca aatcttccaa agaatcctct aagaaaccca agaaaataa accactgaaa     720 gaagagaaaa tagttcctaa gatggccttc aaggaaccta acccatgtc aaaagagcca     780 aaaccagata gtaacttact caccatcacc agtggacaag ataagaaggc tcctagtaaa    840
aggccgccca tttcagattc tgaagaactc tcagccaaaa aaggaaaaa gagtagctca    900 gaggctttat ttaaaagttt ttctagcgca ccaccactga tactcacttg ttctgctgac    960
aaaaaacaga taaaagataa atctcatgtc aagatgggaa aggtcaaaat tgaaagtgag    1020
acatcagaga gaagaaatc aacgttaccg ccatttgatg atattgtgga tcccaatgat   1080
tcagatgtgg aggagaatat atcctctaaa tctgattctg aacaacccag tcctgccagc   1140
tccagctcca gctccagctc cagcttcaca ccatcccaga ccaggcaaca aggtcctttg   1200
aggtctataa tgaaagatct gcattctgat gacaatgagg aggaatcaga tgaagtggag   1260
gataacgaca atgactctga aatggagagg cctgtaaata gaggaggcag ccgaagtcgc   1320
agagttagct taagtgatgg cagcgatagt gaaagcagtt ctgcttcttc acccctacat   1380
cacgaacctc caccaccctt actaaaaaacc aacaacaacc agattcttga agtgaaaagt   1440
ccaataaagc aaagcaaatc agataagcaa ataaagaatg gtgaatgtga caaggcatac   1500
ctagatgaac tggtagagct tcacagaagg ttaatgacat tgagagaaag acacattctg   1560
cagcagatcg tgaaccttat agaagaaact ggacactttc atatcacaaa acaacatttt   1620
gattttgatc tttgctcgct ggacaaaaacc acagtccgta aactacagag ttacctggaa   1680
acatctggaa catcctga                                                 1698
```

<210> SEQ ID NO 3
<211> LENGTH: 568
<212> TYPE: PRT
<213> ORGANISM: Homo sapiens

<400> SEQUENCE: 3

Met Ala Ser Ser Cys Ala Val Gln Val Lys Leu Glu Leu Gly His Arg
1               5                   10                  15

Ala Gln Val Arg Lys Lys Pro Thr Val Glu Gly Phe Thr His Asp Trp
            20                  25                  30

Met Val Phe Val Arg Gly Pro Glu His Ser Asn Ile Gln His Phe Val
        35                  40                  45

Glu Lys Val Val Phe His Leu His Glu Ser Phe Pro Arg Pro Lys Arg
    50                  55                  60

Val Cys Lys Asp Pro Pro Tyr Lys Val Glu Glu Ser Gly Tyr Ala Gly
65                  70                  75                  80

Phe Ile Leu Pro Ile Glu Val Tyr Phe Lys Asn Lys Glu Glu Pro Arg

```
                     85                  90                  95
Lys Val Arg Phe Asp Tyr Asp Leu Phe Leu His Leu Glu Gly His Pro
                100                 105                 110

Pro Val Asn His Leu Arg Cys Glu Lys Leu Thr Phe Asn Asn Pro Thr
            115                 120                 125

Glu Asp Phe Arg Arg Lys Leu Leu Lys Ala Gly Gly Asp Pro Asn Arg
        130                 135                 140

Ser Ile His Thr Ser Ser Ser Ser Ser Ser Ser Ser Ser Ser Ser Ser
145                 150                 155                 160

Ser Ser Ser Ser Ser Ser Ser Ser Ser Ser Ser Ser Ser Ser Ser Ser
                165                 170                 175

Ser Ser Ser Ser Ser Ser Ser Ser Ser Ser Ser Ser Ser Ser Thr Ser
            180                 185                 190

Phe Ser Lys Pro His Lys Leu Met Lys Glu His Lys Glu Lys Pro Ser
        195                 200                 205

Lys Asp Ser Arg Glu His Lys Ser Ala Phe Lys Glu Pro Ser Arg Asp
    210                 215                 220

His Asn Lys Ser Ser Lys Glu Ser Ser Lys Lys Pro Lys Glu Asn Lys
225                 230                 235                 240

Pro Leu Lys Glu Glu Lys Ile Val Pro Lys Met Ala Phe Lys Glu Pro
                245                 250                 255

Lys Pro Met Ser Lys Glu Pro Lys Pro Asp Ser Asn Leu Leu Thr Ile
            260                 265                 270

Thr Ser Gly Gln Asp Lys Lys Ala Pro Ser Lys Arg Pro Pro Ile Ser
        275                 280                 285

Asp Ser Glu Glu Leu Ser Ala Lys Lys Arg Lys Lys Ser Ser Ser Glu
    290                 295                 300

Ala Leu Phe Lys Ser Phe Ser Ser Ala Pro Pro Leu Ile Leu Thr Cys
305                 310                 315                 320

Ser Ala Asp Lys Lys Gln Ile Lys Asp Lys Ser His Val Lys Met Gly
                325                 330                 335

Lys Val Lys Ile Glu Ser Glu Thr Ser Glu Lys Lys Ser Thr Leu
            340                 345                 350

Pro Pro Phe Asp Asp Ile Val Asp Pro Asn Asp Ser Asp Val Glu Glu
        355                 360                 365

Asn Ile Ser Ser Lys Ser Asp Ser Glu Gln Pro Ser Pro Ala Ser Ser
    370                 375                 380

Ser Ser Ser Ser Ser Ser Ser Phe Thr Pro Ser Gln Thr Arg Gln Gln
385                 390                 395                 400

Gly Pro Leu Arg Ser Ile Met Lys Asp Leu His Ser Asp Asp Asn Glu
                405                 410                 415

Glu Glu Ser Asp Glu Val Glu Asp Asn Asp Asn Asp Ser Glu Met Glu
            420                 425                 430

Arg Pro Val Asn Arg Gly Gly Ser Arg Ser Arg Arg Val Ser Leu Ser
        435                 440                 445

Asp Gly Ser Asp Ser Glu Ser Ser Ala Ser Ser Pro Leu His His
    450                 455                 460

Glu Pro Pro Pro Leu Leu Lys Thr Asn Asn Asn Gln Ile Leu Glu
465                 470                 475                 480

Val Lys Ser Pro Ile Lys Gln Ser Lys Ser Lys Gln Ile Lys Asn
                485                 490                 495

Gly Glu Cys Asp Lys Ala Tyr Leu Asp Glu Leu Val Glu Leu His Arg
            500                 505                 510
```

-continued

```
Arg Leu Met Thr Leu Arg Glu Arg His Ile Leu Gln Gln Ile Val Asn
            515                 520                 525

Leu Ile Glu Glu Thr Gly His Phe His Ile Thr Asn Thr Thr Phe Asp
        530                 535                 540

Phe Asp Leu Cys Ser Leu Asp Lys Thr Thr Val Arg Lys Leu Gln Ser
545                 550                 555                 560

Tyr Leu Glu Thr Ser Gly Thr Ser
                565

<210> SEQ ID NO 4
<211> LENGTH: 565
<212> TYPE: PRT
<213> ORGANISM: Homo sapiens

<400> SEQUENCE: 4

Met Cys Ala Val Gln Val Lys Leu Glu Leu Gly His Arg Ala Gln Val
1               5                   10                  15

Arg Lys Lys Pro Thr Val Glu Gly Phe Thr His Asp Trp Met Val Phe
            20                  25                  30

Val Arg Gly Pro Glu His Ser Asn Ile Gln His Phe Val Glu Lys Val
        35                  40                  45

Val Phe His Leu His Glu Ser Phe Pro Arg Pro Lys Arg Val Cys Lys
    50                  55                  60

Asp Pro Pro Tyr Lys Val Glu Glu Ser Gly Tyr Ala Gly Phe Ile Leu
65                  70                  75                  80

Pro Ile Glu Val Tyr Phe Lys Asn Lys Glu Glu Pro Arg Lys Val Arg
                85                  90                  95

Phe Asp Tyr Asp Leu Phe Leu His Leu Glu Gly His Pro Pro Val Asn
            100                 105                 110

His Leu Arg Cys Glu Lys Leu Thr Phe Asn Asn Pro Thr Glu Asp Phe
        115                 120                 125

Arg Arg Lys Leu Leu Lys Ala Gly Gly Asp Pro Asn Arg Ser Ile His
    130                 135                 140

Thr Ser Ser Ser Ser Ser Ser Ser Ser Ser Ser Ser Ser Ser Ser Ser
145                 150                 155                 160

Ser Ser Ser Ser Ser Ser Ser Ser Ser Ser Ser Ser Ser Ser Ser Ser
                165                 170                 175

Ser Ser Ser Ser Ser Ser Ser Ser Ser Ser Thr Ser Phe Ser Lys
            180                 185                 190

Pro His Lys Leu Met Lys Glu His Lys Glu Lys Pro Ser Lys Asp Ser
        195                 200                 205

Arg Glu His Lys Ser Ala Phe Lys Glu Pro Ser Arg Asp His Asn Lys
    210                 215                 220

Ser Ser Lys Glu Ser Ser Lys Lys Pro Lys Glu Asn Lys Pro Leu Lys
225                 230                 235                 240

Glu Glu Lys Ile Val Pro Lys Met Ala Phe Lys Glu Pro Lys Pro Met
                245                 250                 255

Ser Lys Glu Pro Lys Pro Asp Ser Asn Leu Leu Thr Ile Thr Ser Gly
            260                 265                 270

Gln Asp Lys Lys Ala Pro Ser Lys Arg Pro Pro Ile Ser Asp Ser Glu
        275                 280                 285

Glu Leu Ser Ala Lys Lys Arg Lys Lys Ser Ser Glu Ala Leu Phe
    290                 295                 300

Lys Ser Phe Ser Ser Ala Pro Pro Leu Ile Leu Thr Cys Ser Ala Asp
```

```
              305                 310                 315                 320
      Lys Lys Gln Ile Lys Asp Lys Ser His Val Lys Met Gly Lys Val Lys
                          325                 330                 335

Ile Glu Ser Glu Thr Ser Glu Lys Lys Lys Ser Thr Leu Pro Pro Phe
                          340                 345                 350

Asp Asp Ile Val Asp Pro Asn Asp Ser Asp Val Glu Glu Asn Ile Ser
                          355                 360                 365

Ser Lys Ser Asp Ser Glu Gln Pro Ser Pro Ala Ser Ser Ser Ser Ser
                      370                 375                 380

Ser Ser Ser Ser Phe Thr Pro Ser Gln Thr Arg Gln Gln Gly Pro Leu
      385                 390                 395                 400

Arg Ser Ile Met Lys Asp Leu His Ser Asp Asp Asn Glu Glu Glu Ser
                              405                 410                 415

Asp Glu Val Glu Asp Asn Asp Asn Asp Ser Glu Met Glu Arg Pro Val
                      420                 425                 430

Asn Arg Gly Gly Ser Arg Ser Arg Arg Val Ser Leu Ser Asp Gly Ser
                      435                 440                 445

Asp Ser Glu Ser Ser Ser Ala Ser Ser Pro Leu His His Glu Pro Pro
                  450                 455                 460

Pro Pro Leu Leu Lys Thr Asn Asn Asn Gln Ile Leu Glu Val Lys Ser
      465                 470                 475                 480

Pro Ile Lys Gln Ser Lys Ser Asp Lys Gln Ile Lys Asn Gly Glu Cys
                              485                 490                 495

Asp Lys Ala Tyr Leu Asp Glu Leu Val Glu Leu His Arg Arg Leu Met
                      500                 505                 510

Thr Leu Arg Glu Arg His Ile Leu Gln Gln Ile Val Asn Leu Ile Glu
                  515                 520                 525

Glu Thr Gly His Phe His Ile Thr Asn Thr Thr Phe Asp Phe Asp Leu
                      530                 535                 540

Cys Ser Leu Asp Lys Thr Thr Val Arg Lys Leu Gln Ser Tyr Leu Glu
      545                 550                 555                 560

Thr Ser Gly Thr Ser
                      565

<210> SEQ ID NO 5
<211> LENGTH: 489
<212> TYPE: DNA
<213> ORGANISM: Homo sapiens

<400> SEQUENCE: 5
atgaaagatc tgcattctga tgacaatgag gaggaatcag atgaagtgga ggataacgac       60
aatgactctg aaatggagag gcctgtaaat agaggaggca gccgaagtcg cagagttagc      120
ttaagtgatg gcagcgatag tgaaagcagt tctgcttctt caccccctaca tcacgaacct     180 ccaccaccct tactaaaaac caacaacaac cagattcttg aagtgaaaag tccaataaag      240
caaagcaaat cagataagca ataaagaat ggtgaatgtg acaaggcata cctagatgaa        300
ctggtagagc ttcacagaag gttaatgaca ttgagagaaa gacacattct gcagcagatc      360
gtgaacctta tagaagaaac tggacacttt catatcacaa acacaacatt tgattttgat      420
ctttgctcgc tggacaaaac cacagtccgt aaactacaga gttacctgga aacatctgga      480
acatcctga                                                              489

<210> SEQ ID NO 6
<211> LENGTH: 162
```

```
<212> TYPE: PRT
<213> ORGANISM: Homo sapiens

<400> SEQUENCE: 6

Met Lys Asp Leu His Ser Asp Asn Glu Glu Ser Asp Glu Val
1               5                   10                  15

Glu Asp Asn Asp Asn Asp Ser Glu Met Glu Arg Pro Val Asn Arg Gly
            20                  25                  30

Gly Ser Arg Ser Arg Arg Val Ser Leu Ser Asp Gly Ser Asp Ser Glu
            35                  40                  45

Ser Ser Ser Ala Ser Ser Pro Leu His His Glu Pro Pro Pro Pro Leu
    50                  55                  60

Leu Lys Thr Asn Asn Asn Gln Ile Leu Glu Val Lys Ser Pro Ile Lys
65                  70                  75                  80

Gln Ser Lys Ser Asp Lys Gln Ile Lys Asn Gly Glu Cys Asp Lys Ala
                85                  90                  95

Tyr Leu Asp Glu Leu Val Glu Leu His Arg Arg Leu Met Thr Leu Arg
                100                 105                 110

Glu Arg His Ile Leu Gln Gln Ile Val Asn Leu Ile Glu Glu Thr Gly
            115                 120                 125

His Phe His Ile Thr Asn Thr Thr Phe Asp Phe Asp Leu Cys Ser Leu
    130                 135                 140

Asp Lys Thr Thr Val Arg Lys Leu Gln Ser Tyr Leu Glu Thr Ser Gly
145                 150                 155                 160

Thr Ser
```